(12) United States Patent
Korennykh et al.

(10) Patent No.: US 11,859,234 B2
(45) Date of Patent: Jan. 2, 2024

(54) METHOD OF MONITORING RNASE L ACTIVITY

(71) Applicant: THE TRUSTEES OF PRINCETON UNIVERSITY, Princeton, NJ (US)

(72) Inventors: Alexei Korennykh, Princeton, NJ (US); Jesse Donovan, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 315 days.

(21) Appl. No.: 16/099,237

(22) PCT Filed: May 5, 2017

(86) PCT No.: PCT/US2017/031379
§ 371 (c)(1),
(2) Date: Nov. 6, 2018

(87) PCT Pub. No.: WO2017/193051
PCT Pub. Date: Nov. 9, 2017

(65) Prior Publication Data
US 2019/0203259 A1    Jul. 4, 2019

Related U.S. Application Data

(60) Provisional application No. 62/344,104, filed on Jun. 1, 2016, provisional application No. 62/332,729, filed on May 6, 2016.

(51) Int. Cl.
| | |
|---|---|
| *C12Q 1/44* | (2006.01) |
| *C12Q 1/6883* | (2018.01) |
| *C12N 9/22* | (2006.01) |
| *G01N 33/68* | (2006.01) |
| *A61P 11/06* | (2006.01) |

(Continued)

(52) U.S. Cl.
CPC .............. *C12Q 1/44* (2013.01); *A61P 11/06* (2018.01); *A61P 25/00* (2018.01); *A61P 35/00* (2018.01); *A61P 37/06* (2018.01); *C12N 9/22* (2013.01); *C12Q 1/6851* (2013.01);
(Continued)

(58) Field of Classification Search
CPC ... C12Q 1/44; C12Q 1/6883; C12Q 2600/106
See application file for complete search history.

(56) References Cited

U.S. PATENT DOCUMENTS

| 10,160,968 B2 * | 12/2018 | Wickens ............... C07H 21/02 |
| 2012/0208707 A1 | 8/2012 | Zeiner et al. |
| 2012/0251571 A1 | 10/2012 | Silverman et al. |

FOREIGN PATENT DOCUMENTS

| EP | 0285263 A2 | 10/1988 |
| WO | WO-2015/055857 A1 | 4/2015 |

OTHER PUBLICATIONS

Peach, S.E. et al. Nucleic Acids Research 43(17):e108 (May 22, 2015). (Year: 2015).*

(Continued)

*Primary Examiner* — Diana B Johannsen
(74) *Attorney, Agent, or Firm* — MARSHALL, GERSTEIN & BORUN LLP

(57) ABSTRACT

The present disclosure relates, in general, to a method for generating chimeric DNA derived from RNase L cleavage products in a sample, and detection of such RNase L cleavage products for diagnosis and treatment of inflammation and infection in a subject.

17 Claims, 19 Drawing Sheets

Specification includes a Sequence Listing.

(51) Int. Cl.
  *A61P 37/06* (2006.01)
  *A61P 25/00* (2006.01)
  *A61P 35/00* (2006.01)
  *C12Q 1/6851* (2018.01)

(52) U.S. Cl.
  CPC ....... *C12Q 1/6883* (2013.01); *G01N 33/6893* (2013.01); *C12Q 2600/106* (2013.01)

(56) References Cited

OTHER PUBLICATIONS

Cooper, D.A. et al. Journal of Virology 89(5):2764 (Mar. 2015; online Dec. 24, 2014). (Year: 2014).*
Al-Ahmadi et al., RNase L downmodulation of the RNA-binding protein, HuR, and cellular growth, Oncogene, 28(15):1782-91 (Apr. 2009).
Altschul et al., Gapped BLAST and PSI-BLAST: a new generation of protein database search programs, Nucleic Acids Res. 25:3389-402 (1997).
Andersen et al., Ribosomal protein mRNAs are primary targets of regulation in RNase-L-induced senescence, RNA Biol., 6(3):305-15 (Jul.-Aug. 2009).
Aragón et al., Messenger RNA targeting to endoplasmic reticulum stress signalling sites, Nature, 457(7230):736-40 (Feb. 2009).
Bisbal et al., The 2'-5' oligoadenylate/RNase L/RNase L inhibitor pathway regulates both MyoD mRNA stability and muscle cell differentiation, Mol. Cell Biol., 20(14):4959-69 (Jul. 2000).
Braun et al., Immunogenic duplex nucleic acids are nuclease resistant, J. Immunol., 141(6):2084-9 (Sep. 1988).
Brennan-Laun et al., RNase L attenuates mitogen-stimulated gene expression via transcriptional and post-transcriptional mechanisms to limit the proliferative response, J. Biol. Chem., 289(49):33629-43 (Nov. 2014).
Chakrabarti et al., RNase L activates the NLRP3 inflammasome during viral infections, Cell Host Microbe, 17(4):466-77 (Apr. 2015).
Chandrasekaran et al., RNase-L regulates the stability of mitochondrial DNA-encoded mRNAs in mouse embryo fibroblasts, Biochem. Biophys. Res. Commun., 325(1):18-23 (Dec. 2004).
Chaturvedi et al., Stabilization of triple-stranded oligonucleotide complexes: use of probes containing alternating phosphodiester and stereo-uniform cationic phosphoramidate linkages, Nucleic Acids Res., 24(12):2318-23 (Jun. 1996).
Cooper et al., Ribonuclease L and metal-ion-independent endoribonuclease cleavage sites in host and viral RNAs, Nucleic Acids Res., 42(8):5202-16 (Apr. 2014).
Fabre et al., RNase L controls terminal adipocyte differentiation, lipids storage and insulin sensitivity via CHOP10 mRNA regulation, Cell Death Differ., 19(9):1470-81 (Sep. 2012).
Feng et al., Progressive sequence alignment as a prerequisite to correct phylogenetic trees, *J. Mol. Evol.* 25:351-60 (1987).
Han et al., Structure of human RNase L reveals the basis for regulated RNA decay in the IFN response, Science, 343(6176):1244--8 (Mar. 2014).
Higgins et al., Fast and sensitive multiple sequence alignments on a microcomputer, Comput. Appl. Biosci., 5(2):151-3 (1989).
International Application No. PCT/US2017/031379, International Preliminary Report on Patentability, dated Nov. 6, 2018.

International Application No. PCT/US2017/031379, International Search Report and Written Opinion, dated Aug. 17, 2017.
Khabar et al., RNase L mediates transient control of the interferon response through modulation of the double-stranded RNA-dependent protein kinase PKR, J. Biol. Chem., 278(22):20124-32 (May 2003).
Kimmig et al., The unfolded protein response in fission yeast modulates stability of select mRNAs to maintain protein homeostasis, Elife, 1:e00048 (Oct. 2012).
Latimer et al., Specificity of monoclonal antibodies produced against phosphorothioate and ribo modified DNAs, Mol. Immunol., 32(14-15):1057-64 (Oct. 1995).
Le Roy et al., The 2-5A/RNase L/RNase L inhibitor (RLI) [correction of (RNI)] pathway regulates mitochondrial mRNAs stability in interferon alpha-treated H9 cells, J. Biol. Chem., 276(51):48473-82 (Dec. 2001).
Li et al., An essential role for the antiviral endoribonuclease, RNase-L, in antibacterial immunity, Proc. Natl. Acad. Sci. USA, 105(52):20816-21 (Dec. 2008).
Li et al., Extensive terminal and asymmetric processing of small RNAs from rRNAs, snoRNAs, snRNAs, and tRNAs, Nucleic Acids Res., 40(14):6787-99 (Aug. 2012).
Li et al., RNase-L-dependent destabilization of interferon-induced mRNAs. A role for the 2-5A system in attenuation of the interferon response, J. Biol. Chem., 275(12):8880-8 (Mar. 2000).
Malathi et al., A transcriptional signaling pathway in the IFN system mediated by 2'-5'—oligoadenylate activation of RNase L, Proc. Natl. Acad. Sci. USA, 102(41)14533-8 (Oct. 2005).
Malathi et al., Small self-RNA generated by RNase L amplifies antiviral innate immunity, Nature, 448(7155):816-9 (Aug. 2007).
Needleman et al., A general method applicable to the search for similarities in the amino acid sequence of two proteins, J. Mol. Biol., 48(3):443-53 (1970).
Pearson et al., Improved tools for biological sequence comparison, Proc. Natl. Acad. Sci., 85:2444-8 (1988).
Peyrottes et al., Oligodeoxynucleoside phosphoramidates (P-NH2): synthesis and thermal stability of duplexes with DNA and RNA targets, Nucleic Acids Res., 24(10):1841-8 (May 1996).
Schultz et al., Oligo-2'-fluoro-2'-deoxynucleotide N3'-->P5' phosphoramidates: synthesis and properties, Nucleic Acids Res., 24(15):2966-73 (Aug. 1996).
Silverman, Viral encounters with 2',5'-oligoadenylate synthetase and RNase L during the interferon antiviral response, J. Virol., 81(23):12720-9 (Dec. 2007).
Smith et al., Comparison of biosequences, Advances in Applied Mathematics, 2(4):482-9 (1981).
Suhadolnik et al., Upregulation of the 2-5A synthetase/RNase L antiviral pathway associated with chronic fatigue syndrome, Clin. Infect. Dis., 18 Suppl 1:S96-104 (Jan. 1994).
Thompson et al., Clustal W: improving the sensitivity of progressive multiple sequence alignment through sequence weighting, position-specific gap penalties and weight matrix choice, Nucleic Acids Res., 22: 4673-80 (1994).
Washenberger et al., Hepatitis C virus RNA: dinucleotide frequencies and cleavage by RNase L, Virus Res., 130(1-2):85-95 (Dec. 2007).
Wreschner et al., Interferon action—sequence specificity of the ppp(A2'p)nA-dependent ribonuclease, Nature, 289(5796):414-7 (Jan. 1981).
Zhou et al., Interferon action and apoptosis are defective in mice devoid of 2',5'-oligoadenylate-dependent RNase L, EMBO J., 16(21):6355-63 (Nov. 1997).

* cited by examiner

Figure 7

|  |  | SEQ ID NO: |
|---|---|---|
| ATCGTATAGTGGTTAGTACTCTGCGTTGTG | NR_TRNA-HIS-GTG-1-9 | 43 |
| ATCGTATAGTGGTGAGTACTCTGCGTTGTG | NR_TRNA-HIS-GTG-1-9 | 44 |
| TGGCTGGTCCGATGGTAGTGGGTTATCA | NR_004393.1 | 45 |
| GTCTAGGGGTATGATTCTCGCTTTG | NR_TRNA-PRO-TGG-3-5 | 46 |
| TGGCCGTGATCGTATAGTGGTTAGTACTCTGCGTTGTG | NR_TRNA-HIS-GTG-1-9 | 47 |
| TAGTTGGTCCGAGTGTTGTGGGTTA | NR_001571.2 | 48 |
| GCTGGTCCGATGGTAGTGGGTTATCA | NR_004393.1 | 49 |
| GTATAGTGGTGAGTATCCCCGCCTGTCTT | NR_TRNA-ASP-GTC-2-9 | 50 |
| TCGATGGTAGTGGGTTATCA | NR_004393.1 | 51 |
| GTCTAGGGGTATGATTCTCGGTTTG | NR_TRNA-PRO-TGG-2-1 | 52 |
| GGCTGGTCCGATGGTAGTGGGTTATCA | NR_004393.1 | 53 |
| TCGCGAAGGCCCGCGGCGGGTGTTGACGCGATGTGATTTCTGCCCAGTGCTCTGAATGTCAAAGTG | NR_003287.2 | 54 |
| TAGAGTGTTCAAAGCAGGCCCGAGCCGCCTGGATACCGCAGCTAGGAATAATGGAATA | NR_003286.2 | 55 |
| ATCGTATAGTGGTTAGTACTCTGCGCTGTG | NR_TRNA-HIS-GTG-2-1 | 56 |
| AGTACTCTGCGTTGTG | NR_TRNA-HIS-GTG-1-9 | 57 |
| TTGGTCTAGGGGTATGATTCTCGCTTTG | NR_TRNA-PRO-TGG-3-5 | 58 |
| GGGCCGTGATCGTATAGTGGTTAGTACTCTGCGTTGTG | NR_TRNA-HIS-GTG-1-9 | 59 |
| TTGGTCTAGGGGTATGATTCTCGGTTTG | NR_TRNA-PRO-TGG-2-1 | 60 |
| TTGATCGTATAGTGGTTAGTACTCTGCGTTGTG | NR_TRNA-HIS-GTG-1-9 | 61 |
| AAGCGTTTACTTTGAAAAAATTAGAGTGTTCAAAGCAGGCCCGA | NR_003286.2 | 62 |
| CCGATGGTAGTGGGTTATCA | NR_004393.1 | 63 |
| TGGCTGGTCCGATGGTAGTGGGTTA | NR_004393.1 | 64 |
| TCGTATAGTGGTTAGTACTCTGCGTTGTG | NR_TRNA-HIS-GTG-1-9 | 65 |
| TCGGGGCCACGCGCGCGTCCCCGAA | NR_003287.2 | 66 |
| GCCGTGATCGTATAGTGGTTAGTACTCTGCGTTGTG | NR_TRNA-HIS-GTG-1-9 | 67 |
| ACTCTGCGTTGTG | NR_TRNA-HIS-GTG-1-9 | 68 |
| AGGCTGGTCCGATGGTAGTGGGTTATCA | NR_004393.1 | 69 |
| ATATAGCTGCTAAGTGCTGTGTTGTCGTTCCCCCTGCTTAAAATAAAGTTGTTTCTTA | NR_002586.1 | 70 |
| GCGTTTACTTTGAAAAAATTAGAGTGTTCAAAGCAGGCCCGAGCCGCCTGGATACCG | NR_003286.2 | 71 |
| GGGCACTGTTGATCATGGTGTCCAAAAATAGTTAATGTGGCTAAATTGAGACAGGTTA | NR_003026.1 | 72 |
| TGATGGTAGTGGGTTATCA | NM_001190329.1 | 73 |
| TTAGTACTCTGCGTTGTG | NR_TRNA-HIS-GTG-1-9 | 74 |
| AGTGTTGTGGGTTATTGTTA | NR_001571.2 | 75 |
| TGATCGTATAGTGGTTAGTACTCTGCGTTGTG | NR_TRNA-HIS-GTG-1-9 | 76 |
| GGGTAAACGGCGGGAGTAACTATGACTCTCTTAAGGTAGCCAAATGCCTCGTCATCTA | NR_003287.2 | 77 |
| AGTTGGTCCGAGTGTTGTGGGTTATT | NR_001571.2 | 78 |
| GTCTAGTGGTATGATTCTCGCTTTG | NR_TRNA-PRO-TGG-1-1 | 79 |
| AGTGTTGTGGGTTATT | NR_001571.2 | 80 |
| ATACTCTGGTTTCTCTTCAAATCGTA | NR_002757.3 | 81 |
| AGTTGGTCCGAGTGTTGTGGGTTATTGTTA | NR_001571.2 | 82 |
| ATAGTGGTTAGTACTCTGCGTTGTG | NR_TRNA-HIS-GTG-1-9 | 83 |
| TTGCAATGATGTCGTAATTTGCGTCTTACTCTGTTCTCAGCGACAGTTGCCTGCTGTCAGTA | NR_002440.1 | 84 |

Figure 7 (cont'd)

| | | SEQ ID NO: |
|---|---|---|
| AGCAGGACGGTGGCCATGGAAGTCGGAATCCGCTAAGGAGTGTGTAACA ACTCACCTGCCGAATCAACTA | NR_003287.2 | 85 |
| AGAGCATCAGACTTTT | NR_TRNA-LYS-TTT-10-1 | 86 |
| GGCCGTGATCGTATAGTGGTTAGTACTCTGCGTTGTG | NR_TRNA-HIS-GTG-1-9 | 87 |
| TATAGTGGTTAGTACTCTGCGTTGTG | NR_TRNA-HIS-GTG-1-9 | 88 |
| AAAGCGCCTGTTTG | NM_007292.5 | 89 |
| AAGTTGGTCCGAGTGTTGTGGGTTATT | NR_001571.2 | 90 |
| GCGGGCCGCCGGTGAAATACCACTACTCTGATCGTTTTTTCACTGACCC GGTGAGGCGGGG | NR_003287.2 | 91 |
| TAGTACTCTGCGTTGTG | NR_TRNA-HIS-GTG-1-9 | 92 |
| GCCCGGCTAGCTCAGTCGGTAGAGCATGGGACTCTT | NR_TRNA-LYS-CTT-1-2 | 93 |
| GTGTAATGGTTAGCACTCTGGACTCTGCA | NR_TRNA-GLN-CTG-1-5 | 94 |
| TGGTCCGATGGTAGTGGGTTATCA | NR_004393.1 | 95 |
| TCTGTGGCAGATGATCAAAACTGTCTGACACAATTTGAGCTTGCTATAG CAAGAAAGTCTAACCTA | NR_002964.1 | 96 |
| CGATGGTAGTGGGTTATCA | NR_004393.1 | 97 |
| AAGTTGGTCCGAGTGTTGTGGGTTATTGTTA | NR_001571.2 | 98 |
| GTTGGTCCGAGTGTTGTGGGTTATT | NR_001571.2 | 99 |
| AGTACTCTGCGCTGTG | NR_TRNA-HIS-GTG-2-1 | 100 |
| GAGTTGGTCCGAGTGTTGTGGGTTATTGTT | NR_001571.2 | 101 |
| AGAGCACTGGTCTT | NR_TRNA-THR-TGT-2-1 | 102 |
| GGGCTGGTCCGATGGTAGTGGGTTATCA | NR_004393.1 | 103 |
| GTGTAATGGTTAGCACTCTGGACTCTGTA | NR_TRNA-GLN-CTG-1-5 | 104 |
| GGCCGTGATCGTATAGTGGTGAGTACTCTGCGTTGTG | NR_TRNA-HIS-GTG-1-9 | 105 |
| GTAATGGTTAGCACTCTGGACTCTG | NR_TRNA-GLN-CTG-1-5 | 106 |
| ATTAACATTAGTGTCACTAAAGTTGGTA | NR_004393.1 | 107 |
| GTTGGTCCGAGTGTTGTGGGTTATTGTT | NR_001571.2 | 108 |
| TCGCGAAGGCCCGCGGCGGGTGTTGACGCGATGTG | NR_003287.2 | 109 |
| AGAGCACTGGTCTTG | NR_TRNA-THR-TGT-2-1 | 110 |
| ATAACTCAGTCGGTAGAGCATCAGACTTTT | NR_TRNA-LYS-TTT-3-5 | 111 |
| GAAGTCGGAATCCGCTAAGGAGTGTGTAACAACTCACCTGCCGAATCAA CTAGCCCTG | NR_003287.2 | 112 |
| ATCGTATAGTGGTTAGGACTCTGCGTTGTG | NR_TRNA-HIS-GTG-1-9 | 113 |
| GCGGGCCGCCGGTGAAATACCACTACTCTGATC | NR_003287.2 | 114 |
| TTGCACTGCATGGTA | NR_002920.1 | 115 |
| GAGTTGGTCCGAGTGTTGTGGGTTATTGTTA | NR_001571.2 | 116 |
| TAGTTGGTCCGAGGGTTGTGGGTTATTGTT | NR_001571.2 | 117 |
| GGACGGTGGCCATGGAAGTCGGAATCCGCTAAGGAGTGTGTAACAACTC ACCTGCCGAATCAACTA | NR_003287.2 | 118 |
| ATCACGTCTGCTTTA | NR_TRNA-VAL-TAC-1-2 | 119 |
| AAGAAATTCAATGAAGCGCGGGTAAACGGCGGGAGTAACTATGACTCTCTTA | NR_003287.2 | 120 |
| ATCGTATAGTGGTTAGTACTCTGCGTTGTT | NR_TRNA-HIS-GTG-1-9 | 121 |
| CTGGTCCGATGGTAGTGGGTTATCA | NR_004393.1 | 122 |
| ATATACTCTGGTTTCTCTTCAAATCGTA | NR_002754.2 | 123 |
| GCGTTGGTGGTATAGTGGTA | NR_TRNA-GLY-TCC-3-1 | 124 |
| CGGGCCGCCGGTGAAATACCACTACTCTGATCGTTTTTCACTGACCCG GTGAGGCGGGG | NR_003287.2 | 125 |
| GTTGGTCCGAGTGTTGTGGGTTATTGTTA | NR_001571.2 | 126 |
| ATGGTTAGCACTCTGGACTCTG | NR_TRNA-GLN-CTG-1-5 | 127 |
| TAATGGTTAGCACTCTGGACTCTG | NR_TRNA-GLN-CTG-1-5 | 128 |
| TCTAGGGGTATGATTCTCGCTTTG | NR_TRNA-PRO-TGG-3-5 | 129 |

Figure 7 (cont'd)

|  |  | SEQ ID NO: |
|---|---|---|
| ATACTTACCTGGCAGGGGAGATACCATGATTA | NR_004430.2 | 130 |
| GTATAGTGGTTAGTACTCTGCGTTGTG | NR_TRNA-HIS-GTG-1-9 | 131 |
| TAGTTGGATCTTGGGAGCGGGCGGGCGGTCCGCCGCGAGGCGAGCCACCGCCCGTCCCCGCCCCTT | NR_003286.2 | 132 |
| AGCGTTTACTTTGAAAAAATTAGAGTGTTCAAAGCAGGCCCGA | NR_003286.2 | 133 |
| AAGCGTTTACTTTGAAAAAATTAGAGTGTTCAAAGCAGGCCCG | NR_003286.2 | 134 |
| TAGTTGGTCCGAGTGTTGTGGGTTATT | NR_001571.2 | 135 |
| GGTCCGATGGTAGTGGGTTATCA | NR_004393.1 | 136 |
| ATAAGTGGGAGGCCCCCGGCGCCCCCCCGGTGTCCCCGCGAGGGGCCCGGGGCGGGGTCCGCCGGCCCTG | NR_003287.2 | 137 |
| AAGCGTTTACTTTGAAAAAATTAGAGTGTTCAAAGCAGGCCCGAGCCGCCTGGATACC | NR_003286.2 | 138 |
| CGTATAGTGGTTAGTACTCTGCGTTGTG | NR_TRNA-HIS-GTG-1-9 | 139 |
| GTATAGTGGTGAGTATCCCCGCCTGTT | NR_TRNA-ASP-GTC-2-9 | 140 |
| TCGGGCCGCCGGTGAAATACCACTACTCTGATC | NR_003287.2 | 141 |
| TAGTTGGTCCGAGTGTTGTGGGTTATTGTTA | NR_001571.2 | 142 |
| TAGTTGGTCCGAGTGTTGTGGGTTATTG | NR_001571.2 | 143 |
| AGCAGGACGGTGGCCATGGAAGTCGGAATCCGCTAAGGAGTGTGTAACAACTCACCTGCCGA | NR_003287.2 | 144 |
| TTGGACTTAAGATCCAATGGACATA | NR_TRNA-LEU-TAA-1-1 | 145 |
| AGCACTCTGGACTTTG | NR_TRNA-GLN-TTG-1-1 | 146 |
| GTGTAATGGTTAGCACTCTGGACTCTGGA | NR_TRNA-GLN-CTG-1-5 | 147 |
| TCGGGCCGCCGGTGAAATACCACTACTCTGATCGTTTTTTCACTGACCCGGT | NR_003287.2 | 148 |
| GAAGCGTTTACTTTGAAAAAATTAGAGTGTTCAAAGCAGGCCCG | NR_003286.2 | 149 |
| TAGTTGGTCCGAGTGTTGTGGGTTATTGTT | NR_001571.2 | 150 |
| AATCGTATAGTGGTTAGTACTCTGCGTTGTG | NR_TRNA-HIS-GTG-1-9 | 151 |
| ATCCAATGGATTCATA | NR_TRNA-LEU-TAA-3-1 | 152 |
| TTTGGTCTAGGGGTATGATTCTCGGTTTG | NR_TRNA-PRO-TGG-2-1 | 153 |
| GTTAGCACTCTGGACTCTG | NR_TRNA-GLN-CTG-1-5 | 154 |
| AAGCGTTTACTTTGAAAAAATTAGAGTGTTCAAAGCAGGCCCGAGCCGCCTGGATACCG | NR_003286.2 | 155 |
| AGTTGGTCCGAGGGTTGTGGGTTATT | NR_001571.2 | 156 |
| GTGTAATGGTTAGCACTCTGGACTCTGTG | NR_TRNA-GLN-CTG-1-5 | 157 |
| TTTGGTCTAGGGGTATGATTCTCGCTTTG | NR_TRNA-PRO-TGG-3-5 | 158 |
| AGATCTGGTTTCTCTTCATA | NR_002753.5 | 159 |
| CGGCTGGTCCGATGGTAGTGGGTTATCA | NR_004393.1 | 160 |
| TAGTTGGTCCGAGTGTTGTGGGTTATTGTTAAGTTG | NR_001571.2 | 161 |
| TAGTTGGTCCGAGTGTTGTGGGTTATTGTTAAGTTGATTTAACATT | NR_001571.2 | 162 |
| GGCTGGTCCGAAGGTAGTGAGTTATCTCAATT | NR_004391.1 | 163 |
| AGCGCATTCGGCTGTT | NR_TRNA-ASN-GTT-3-2 | 164 |
| TCGAGGCCCTGTAATTGGAATGAGTCCACTTTAAATCCTTTAACGAGGATCCATTGGAGGGCAAGT | NR_003286.2 | 165 |
| TCGCGAAGGCCCGCGGCGGGTGTTGACGCGATG | NR_003287.2 | 166 |
| TTATAGTGGTTAGTACTCTGCGTTGTG | NR_TRNA-HIS-GTG-1-9 | 167 |
| GTGTAATGGTAAGCACTCTGGACTCTG | NR_TRNA-GLN-CTG-4-2 | 168 |
| CGTGCTTGGGTCTGCGGTGACCCTATGCATTCCTTCAGTGCTTGCTAGAACAGTTTTGAAACGGTT | NR_002952.1 | 169 |
| GGTAACGCAGGTGTCCTA | NR_003287.2 | 170 |
| ATTAAAACAAAGCATCGCGAAGGCCCGCGGCGGGTGTTGACGCGATGTGATT | NR_003287.2 | 171 |
| GTGTAATGGTTAGCACTCTGGACTCTG | NR_TRNA-GLN-CTG-1-5 | 172 |

Figure 7 (cont'd)

|  |  | SEQ ID NO: |
|---|---|---|
| TGGTCCGAGTGTTGTGGGTTATT | NR_001571.2 | 173 |
| GTGTAATGGTTAGCACTCTGGACTTTG | NR_TRNA-GLN-TTG-1-1 | 174 |
| AGTTGGTCCGAGTGTTG | NR_001571.2 | 175 |
| TGTAATGGTTAGCACTCTGGACTTTG | NR_TRNA-GLN-TTG-1-1 | 176 |
| ATAGCTCAGTCGGTAGAGCATCAGACTTTT | NR_TRNA-LYS-TTT-3-5 | 177 |
| CGGGCCGCCGGTGAAATACCACTACTCTGATC | NR_003287.2 | 178 |
| AGTTGGTCCGAGTGTTGTGGGTTA | NR_001571.2 | 179 |
| TGGGTATCGGCTATTGCCTGAGTGTGCTAGAGTCCTCGAAGAGTAACTGCTGACCTTA | NR_002580.1 | 180 |
| TCCCTGGTGGTCTAGTGGCTAGGATTCGGCGCTT | NR_TRNA-GLU-TTC-4-2 | 181 |
| GTATAAACTAATACACCAGTC | NR_MT_tRNA threonine | 182 |
| TAGAGCATCAGACTTTT | NR_TRNA-LYS-TTT-10-1 | 183 |
| GTCCCGCGGGGCCCGAAGCGTTTACTTTGAAAAAATTAGAGTGTTCAAAGCAGGCCCG | NR_003286.2 | 184 |
| TGCTAATGTGAGACGAATTTTTGAGCGGGTAAAGGTCGCCCTCAAGGTGACCCGCCTA | NR_029422.1 | 185 |
| TGGCAGGGGAGATACCATGATCACGAAGGTGGTTTTCTCAGGGCGAGGCTTATCCATT | NR_004430.2 | 186 |
| AGTTGGTCCGAGTGT | NR_001571.2 | 187 |
| TGGTTAGTACTCTGCGTTGTG | NR_TRNA-HIS-GTG-1-9 | 188 |
| TCCGATGGTAGTGGGTTATCA | NR_004393.1 | 189 |
| GCTGAGTGTCCCGCGGGGCCCGAAGCGTTTACTTTGAAAAAATTAGAGTGTTCAAAGCAGGCCCGA | NR_003286.2 | 190 |
| TGGTCCGAGTGTTGTGGGTTATTGTT | NR_001571.2 | 191 |
| TGGTCCGAGTGTTGTGGGTTATTGTTA | NR_001571.2 | 192 |
| TTGGTCCGATGGTAGTGGGTTATCA | NR_004393.1 | 193 |
| AAGAAATTCAATGAAGCGCGGGTAAACGGCGGGAGTAACTATGACTCTCTT | NR_003287.2 | 194 |
| AGTGTTGTGGGTTATTGTT | NR_001571.2 | 195 |
| AGTTGGTCCGAGTGTGGTGGGTTATTGTT | NR_001571.2 | 196 |
| AGTTGGTCCGAGTGTTGTGGGTATTA | NR_001571.2 | 197 |
| ATTGAAACAAGCAACCTGTCTGGGTTGTTCGAGACCCGCGGGCGCTCTCCAGTCCTT | NR_026703.1 | 198 |
| GAGTTGGTCCGAGTGTTGTGGGTTA | NR_001571.2 | 199 |
| TAATGTGAGACGAATTTTTGAGCGGGTAAAGGTCGCCCTCAAGGTGACCCGCCTACTT | NR_029422.1 | 200 |
| ATTGAAACAAGCAACCTGTCTGGGTTGTTCGAGACCCGCGGGCGCTCTCCAGTCCTTT | NR_026703.1 | 201 |
| CGAGTGTTGTGGGTTATTGTTA | NR_001571.2 | 202 |
| AAGAAATTCAATGAAGCGCGGGTAAACGGCGGGAGTAACTA | NR_003287.2 | 203 |
| ATAGAAGCCGGCGTAAAGA | NR_MT_12S | 204 |
| TGGCTGGTCCGAAGGTAGTGAGTTATCTCAATTG | NR_004391.1 | 205 |
| TTAGCACTCTGGACTTTG | NR_TRNA-GLN-TTG-1-1 | 206 |
| AATGGTTAGCACTCTGGACTCTG | NR_TRNA-GLN-CTG-1-5 | 207 |
| GCTGAGTGTCCCGCGGGGCCCGAAGCGTTTACTTTGAAA | NR_003286.2 | 208 |
| CAGTTGGTCCGAGTGTTGTGGGTTATT | NR_001571.2 | 209 |
| TGGCTGGTCCGAAGGTAGTGAGTTA | NR_004391.1 | 210 |
| AAGGTAGCCAAATGCCTCGTCATCTA | NR_003287.2 | 211 |
| AGGTAGCCAAATGCCTCGTCATCTA | NR_003287.2 | 212 |
| ATACATGCCGACGGGCGCTGACCCCCTTCGCGGGGGGATGCGTGCATTT | NR_003286.2 | 213 |
| ATGGCTGGTCCGATGGTAGTGGGTTATCA | NR_004393.1 | 214 |

Figure 7 (cont'd)

|  |  | SEQ ID NO: |
|---|---|---|
| GGTTAGCACTCTGGACTTTG | NR_TRNA-GLN-TTG-1-1 | 215 |
| TACTCTGCGTTGTG | NR_TRNA-HIS-GTG-1-9 | 216 |
| GTGTTGTATGAAAGGAGAGAAGGTTA | NR_023344.1 | 217 |
| TCACATCCTGACACAACTCTTGTCCTGGTGTGCTAGAGTACTCGAAGAGAATCTACTGGTCTTG | NR_002977.1 | 218 |
| AGCTGCTAAGTGCTGTGTTGTCGTTCCCCCTGCTTAAAATAAAGTTGTTTCTTAACTA | NR_002586.1 | 219 |
| GCCTCGTTAGCGCAGTA | NR_TRNA-MET-CAT-1-1 | 220 |
| GGTTAGCACTCTGGACTCTG | NR_TRNA-GLN-CTG-1-5 | 221 |
| GTCTAGGGGTAGGATTCTCGCTTTG | NR_TRNA-PRO-TGG-3-5 | 222 |
| TGAAGCGTTTACTTTGAAAAAATTAGAGTGTTCAAAGCAGGCCCG | NR_003286.2 | 223 |
| TGGCTGGTCCGAAGGTAGTGAGTTATCTCAATT | NR_004391.1 | 224 |
| TTAGAGCATCAGACTTTT | NR_TRNA-LYS-TTT-10-1 | 225 |
| AGAGCACTGGTATTG | NR_TRNA-THR-TGT-2-1 | 226 |
| ATAAGTGGGAGGCCCCCGGCGCCCCCCCGGTGTCCCCGCGAGGGGCCCGGGGCGGGGT | NR_003287.2 | 227 |
| CTGAGTGTCCCGCGGGGCCCGAAGCGTTTACTTTGAAA | NR_003286.2 | 228 |
| GCGATGGTAGTGGGTTATCA | NR_004393.1 | 229 |
| GTGTAATGGTTAGCACTCTGGACTCTGCG | NR_TRNA-GLN-CTG-1-5 | 230 |
| TGCCGTGATCGTATAGTGGTTAGTACTCTGCGTTGTG | NR_TRNA-HIS-GTG-1-9 | 231 |
| AGTTGGTCCGAGTGTTGTGGGTTATTGTT | NR_001571.2 | 232 |
| AAGCGTTTACTTTGAAA | NR_003286.2 | 233 |
| GTGTAATGGTTAGCACTCTGGACTCTGTT | NR_TRNA-GLN-CTG-1-5 | 234 |
| TAGAGCACTGGTTTTG | NR_TRNA-THR-TGT-2-1 | 235 |
| AAGCGTTTACTTTGAAAAAATTAGAGTGTTC | NR_003286.2 | 236 |
| CTTTGAAAAAATTAGAGTGTTCAAAGCAGGCCCGAGCCGCCTGGATACCGCAGCTAGGAATAATGG | NR_003286.2 | 237 |
| GGTCCGAGTGTTGTGGGTTATTGTTA | NR_001571.2 | 238 |
| GTATAAACTAATACACCAGTA | NR_MT_tRNA threonine | 239 |
| ATCGTATAGTGGTGAGTACTCTGCGCTGTG | NR_TRNA-HIS-GTG-2-1 | 240 |
| GCACTCCGGATGTGCTGACCCCTGCGATTTCCCCAAATGTGGGAAACTCGACTGCATT | NR_004430.2 | 241 |
| AGTGTAATGGTTAGCACTCTGGACTTTG | NR_TRNA-GLN-TTG-1-1 | 242 |
| CGAGTGTTGTGGGTTATT | NR_001571.2 | 243 |
| GGCTGGTCCGAAGGTAGTGAGTTATCTCAATTGATTGTTCACAGTCAGTT | NR_004391.1 | 244 |
| TCACGTCTGCTTTA | NR_TRNA-VAL-TAC-1-2 | 245 |
| TTGGTCCGAGTGTTGTGGGTTATTG | NR_001571.2 | 246 |
| CAGTTGGTCCGAGTGTTGTGGGTTATTGTTA | NR_001571.2 | 247 |
| TTAGACCGTCGTGAGACAGGTTAGTT | NR_003287.2 | 248 |
| GGCTGGTCCGAAGGTAGTGAGTTA | NR_004391.1 | 249 |
| ATAGGGAACGTGAGCTGGGTTTAGACCGTCGTGAGACAGGTTAGTT | NR_003287.2 | 250 |
| GAGCTTCCTCGTGGCGCCGGGGGTCAATCTGCAGCGCTAGAGCATGTGCTTGCGCATA | NR_002995.1 | 251 |
| GTATAAACTAATACACCAGTTA | NR_MT_tRNA threonine | 252 |
| TAGGGGTATGATTCTCGCTTTG | NR_TRNA-PRO-TGG-3-5 | 253 |
| TGAAGCGTTTACTTTGAAAAAATTAGAGTGTTCAAAGCAGGCCC | NR_003286.2 | 254 |
| GAGTTGGTCCGAGTGTTGTGGGTTATT | NR_001571.2 | 255 |
| GAGTGTTGTGGGTTATTGTTA | NR_001571.2 | 256 |
| TCGATGGTAGTGGGTTATC | NR_004393.1 | 257 |
| AAGGTAGTGAGTTATCTCAATT | NR_004391.1 | 258 |

Figure 7 (cont'd)

| | | SEQ ID NO: |
|---|---|---|
| AGCAGGAGGTGTCAGAAAAGTT | NR_003287.2 | 259 |
| CCGAGTGTTGTGGGTTATT | NR_001571.2 | 260 |
| CCGTGATCGTATAGTGGTTAGTACTCTGCGTTGTG | NR_TRNA-HIS-GTG-1-9 | 261 |
| GCCATGGAAGTCGGAATCCGCTAAGGAGTGTGTAACAACTCACCTGCCGAATCAACTAGCCCTGTT | NR_003287.2 | 262 |
| TTGGTCCGAGTGTTGTGGGTTATT | NR_001571.2 | 263 |
| CGGGCCGCCGGTGAAATACCACTACTCTGATCGTTTTTTCACTGACCCGGT | NR_003287.2 | 264 |
| TAAGGTAGTGAGTTATCTCAATT | NR_004391.1 | 265 |
| TATCAGTGATGTTGTAAAAATAAATGTCTGAACATA | NR_002583.1 | 266 |
| AGTTGGTCCGAGGGTTGTGGGTTATTGTT | NR_001571.2 | 267 |
| ACAATACAGGACTCTTTCGAGGCCCTGTAATTGGAATGAGTCCACTTTA | NR_003286.2 | 268 |
| ACGAACGAGACTCTGGCATGCTAACTA | NR_003286.2 | 269 |
| ATCGAGGCCCAGCCCGTGGACGGTGTGAGGCCGGTA | NR_003287.2 | 270 |
| GTATAAACTAATACACCAGTCT | NR_MT_tRNA threonine | 271 |
| GTTGGTCCGAGTGTTGTGGGTTATTG | NR_001571.2 | 272 |
| AGTTGGTCCGAGTGTTGTGGGTTATTGTTAAGTTGATTTAACATT | NR_001571.2 | 273 |
| AGTGTAATGGTTAGCACTCTGGACTCTG | NR_TRNA-GLN-CTG-1-5 | 274 |
| AAATATGATGAGTGTACAAAATCTTGATTT | NR_003687.1 | 275 |
| AAGTTGGTCCGAGTGTTGTGGGTTATTG | NR_001571.2 | 276 |
| AGGGGTATGATTCTCGGTTTG | NR_TRNA-PRO-TGG-2-1 | 277 |
| GCGTTTACTTTGAAAAAATTAGAGTGTTCAAAGCAGGCCCGAGCCGCCTGGATACCGC | NR_003286.2 | 278 |
| TGATTCTCGCTTTG | NR_TRNA-PRO-TGG-1-1 | 279 |
| AAAGCACCTGTTTG | NM_001120.4 | 280 |
| ATACTCGGGTTTCTCTTCAAAACGCATAAATCT | NM_001166292.1 | 281 |
| ATCGTATAGTGGTTAGTACTCTGCGTTGTGTA | NR_TRNA-HIS-GTG-1-9 | 282 |
| ATCGTATAGTGGTTAGTACTCTGCGTTGTT | NR_TRNA-HIS-GTG-1-9 | 283 |
| ATTAAAACAAAGCATCGCGAAGGCCCGCGGCGGGTGTT | NR_003287.2 | 284 |
| GTGGGAGGCCCCCGGCGCCCCCCCGGTGTCCCCGCGAGGGGCCCGGGGCGGGGTCCGCCGGCCCTG | NR_003287.2 | 285 |
| ACAGATCGAACTCCTTGTTCTACTCTT | NR_004391.1 | 286 |
| ACGAACGAGACTCTGGCATGCTA | NR_003286.2 | 287 |
| GAGTGTTGTGGGTTATT | NR_001571.2 | 288 |
| GAGTTGGTCCGAGTGTTGTGGGTTATTGTTAA | NR_001571.2 | 289 |
| TAGTGGTTAGTACTCTGCGTTGTG | NR_TRNA-HIS-GTG-1-9 | 290 |
| TCGGGCCGCCGGTGAAATACCACTACTCTGATCGTTTTTTCACTGACCCGGTGAGGCGGGGG | NR_003287.2 | 291 |
| TGCACCTGACCAGGTCTCTGTTGGCTGGTGCAATCCAGTGGTGAGCTGATAGTAAACCCCAGCTTA | NR_002449.2 | 292 |
| TGCCGTGATCGTATAGTGGTTA | NR_TRNA-HIS-GTG-1-9 | 293 |
| TTTGGTGGTTCAGTGGTAGAA | NR_TRNA-GLY-CCC-1-2 | 294 |
| ATGATTCTCGCTTTG | NR_TRNA-PRO-TGG-1-1 | 295 |
| ACGGGTGACGGGGAA | NR_003286.2 | 296 |
| ATACCGCAGCTAGGAATAATGGAATA | NR_003286.2 | 297 |
| CACGCGCGCGTCCCCCGAAGAGGGGGACGGCGGAGCGAGCGCACGGGTCGGCGGCGA | NR_003287.2 | 298 |
| GGTTCCATAGTGTAGCGGTTATCACGTCTGCTTTA | NR_TRNA-VAL-TAC-2-1 | 299 |
| GTGTAATGGTTAGCACTCTGGACTTTGTA | NR_TRNA-GLN-TTG-1-1 | 300 |
| TAGTTGGTCCGAGTGTTGTGGGTTATTGTTAAGTTGATT | NR_001571.2 | 301 |

Figure 7 (cont'd)

| | | SEQ ID NO: |
|---|---|---|
| TTTGAAAAAATTAGAGTGTTCAAAGCAGGCCCGAGCCGCCTGGATACCGCAGCTAGGAATAATGGA | NR_003286.2 | 302 |
| AGTTGGTCCGAGTGTTGTGGGTTATTG | NR_001571.2 | 303 |
| ACAAAGCATCGCGAAGGCCCGCGGCGGGTGTTGACGCGATGTGATT | NR_003287.2 | 304 |
| AGTTGGTCCGAGTGTTGTGGGTTATTGTTAAGTTGATTTAACAT | NR_001571.2 | 305 |
| GGGCTGGCTTTAGCTCAGCGGTTACTTCGAGTA | NR_026704.1 | 306 |
| GGGCTGGTCCGATGGTAGTGGGTTA | NR_004393.1 | 307 |
| GTCTTGTTTGTAGCTTCACGGGCCAAGCAACAGTGCTAGAGCATAACGACTTGTTATA | NR_002980.1 | 308 |
| TATGATTCTCGCTTTG | NR_TRNA-PRO-TGG-1-1 | 309 |
| AAAACAAAGCATCGCGAAGGCCCGCGGCGGGTGTTGACGCGATGTGATT | NR_003287.2 | 310 |
| AAGCGTTTACTTTGAAAAAATTAGAGTGTTCAAAGCA | NR_003286.2 | 311 |
| AGCAGGAGGTGTCAGAAAAGTTACCACAGGGATA | NR_003287.2 | 312 |
| AGTTGGTCCGAGTGTTGTGGGTTATTT | NR_001571.2 | 313 |
| ATAGTTGGTCCGAGTGTTGTGGGTTATTGTTA | NR_001571.2 | 314 |
| ATTGTGAAGCAGAATTCACCAAGCGTTGGATTGTTCACCCACTA | NR_003287.2 | 315 |
| GAGTTGGTCCGAGTGTTGTGGGTTATTG | NR_001571.2 | 316 |
| TGGATGTGAGGGCGATCTGGCTGCGACATCTGTCACCCCATTGATCGCCAGGGTTG | NR_001445.2 | 317 |
| CCGAGTGTTGTGGGTTATTGTT | NR_001571.2 | 318 |
| CTAGGGGTATGATTCTCGGTTTG | NR_TRNA-PRO-TGG-2-1 | 319 |
| GAAGCGTTTACTTTGAAAAAATTAGAGTGTTCAAAGCAGGCCCGA | NR_003286.2 | 320 |
| TTAGCACTCTGGACTCTG | NR_TRNA-GLN-CTG-1-5 | 321 |
| CAGTTGGTCCGAGTGTTGTGGGTTATTGTT | NR_001571.2 | 322 |
| AGTTGGTCCGAGTGTTGTGGGTTATTGTTAAGTTGATTTAACATTG | NR_001571.2 | 323 |
| AATAAGTGGGAGGCCCCCGGCGCCCCCCGGTGTCCCCGCGAGGGGCCCGGGGCGGGGTCCGCCGGCCCT | NR_003287.2 | 324 |
| AGTTGGTCCGAGTGTTGTGGGTTATTGTTAAGTTGATT | NR_001571.2 | 325 |
| CTAGGGGTATGATTCTCGCTTTG | NR_TRNA-PRO-TGG-3-5 | 326 |
| GCTTTCTTTTATGTGAGTAGTGTTATTTCTTATGTGCTATACAAATAATTGAAGGCTA | NR_002917.1 | 327 |
| GTTAGTACTCTGCGTTGTG | NR_TRNA-HIS-GTG-1-9 | 328 |
| TAGCAGGACGGTGGCCATGGAAGTCGGAATCCGCTAAGGAGTGTGTAACAACTCACCTGCCGA | NR_003287.2 | 329 |
| AAGAAATTCAATGAAGCGCGGGTA | NR_003287.2 | 330 |
| ACGTGCGCGAGTCGGGGGCTCGCACGAAAGCCGCCGTGGCGCAATG | NR_003287.2 | 331 |
| GTATAGTGGTGAGTATCCCCGCCTGTCTA | NR_TRNA-ASP-GTC-2-9 | 332 |
| GTCCGATGGTAGTGGGTTATCA | NR_004393.1 | 333 |
| TAGCCAAATGCCTCGTCATCTA | NR_003287.2 | 334 |
| TCAGATCAAAACCAACCCGGTCAGCCCCTCTCCGGCCCCGGCCGGGGGCGGGCGCCGGCGGCTTT | NR_003286.2 | 335 |
| TCATTGTGAAGCAGAATTCACCAAGCGTTGGATTGTTCACCCACTA | NR_003287.2 | 336 |
| TGGCTGGTCCGAAGGTAGTGAGTT | NR_004391.1 | 337 |
| GTTAGCACTCTGGACTTTG | NR_TRNA-GLN-TTG-1-1 | 338 |
| AAGCGTTTACTTTGAAAAAATTAGAG | NR_003286.2 | 339 |
| ACGAGACTCTGGCATGCTA | SNR_003286.2 | 340 |
| AGTGCGGTAACGCGACCGATCCCGGAGAAGCCGGCGGGAGCCCCGGGGAGAGTTCTCTTTTCTT | NR_003287.2 | 341 |

Figure 8

28S rRNA (4032) SEQ ID NO:342

CGCGACCTCAGATCAGACGTGGCGACCCGCTGAATTTAAGCATATTAGTCAGCGGAGGAGAAGAAACTAA
CCAGGATTCCCTCAGTAACGGCGAGTGAACAGGGAAGAGCCCAGCGCCGAATCCCCGCCCCGCGGCGGGG
CGCGGGACATGTGGCGTACGGAAGACCCGCTCCCCGGCGCCGCTCGTGGGGGGCCCAAGTCCTTCTGATC
GAGGCCCAGCCCGTGGACGGTGTGAGGCCGGTAGCGGCCCCGGCGCGCCGGGCCCGGGTCTTCCCGGAG
TCGGGTTGCTTGGGAATGCAGCCCAAAGCGGGTGGTAAACTCCATCTAAGGCTAAATACCGGCACGAGAC
CGATAGTCAACAAGTACCGTAAGGGAAAGTTGAAAAGAACTTTGAAGAGAGAGTTCAAGAGGGCGTGAAA
CCGTTAAGAGGTAAACGGGTGGGTCCGCGCAGTCCGCCCGGAGGATTCAACCCGGCGGCGGGTCCGGCC
GTGTCGGCGGCCCGGCGGATCTTTCCCGCCCCCGTTCCTCCCGACCCCTCCACCCGCCCTCCCTTCCCC
CGCCGCCCCTCCTCCTCCTCCCCGGAGGGGCGGGCTCCGGCGGGTGCGGGGGTGGGCGGGCGGGCCGG
GGGTGGGGTCGGCGGGGGACCGTCCCCCGACCGGCGACCGGCCGCCGCCGGGCGCATTTCCACCGCGGCG
GTGCGCCGCGACCGGCTCCGGGACGGCTGGGAAGGCCCGGCGGGGAAGGTGGCTCGGGGGGCCCCGTCCG
TCCGTCCGTCCGTCCTCCTCCTCCCCCGTCTCCGCCCCCGGCCCCGCGTCCTCCCTCGGGAGGGCGCGC
GGGTCGGGGCGGCGGCGGCGGCGGCGGTGGCGGCGGCGGCGGCGGCGGGACCGAAACCCCCCCCCGAG
TGTTACAGCCCCCCCGGCAGCAGCACTCGCCGAATCCCGGGGCCGAGGGAGCGAGACCCGTCGCCGCGCT
CTCCCCCCTCCCGGCGCCCACCCCCGCGGGGAATCCCCCGCGAGGGGGGTCTCCCCCGCGGGGCGCGCC
GGCGTCTCCTCGTGGGGGGGCCGGGCCACCCCTCCCACGGCGCGACCGCTCTCCCACCCCTCCTCCCCGC
GCCCCCGCCCCGGCGACGGGGGGGGTGCCGCGCGCGGGTCGGGGGCGGGGCGGACTGTCCCCAGTGCGC
CCCGGGCGGGTCGCGCCGTCGGGCCCGGGGGAGGTTCTCTCGGGGCCACGCGCGCGTCCCCCGAAGAGGG
GGACGGCGGAGCGAGCGCACGGGTCGGCGGCGACGTCGGCTACCCACCCGACCCGTCTTGAAACACGGA
CCAAGGAGTCTAACACGTGCGCGAGTCGGGGGCTCGCACGAAAGCCGCCGTGGCGCAATGAAGGTGAAGG
CCGGCGCGCTCGCCGGCCGAGGTGGGATCCCGAGGCCTCTCCAGTCCGCCGAGGGCGCACCACCGGCCCG
TCTCGCCCGCCGCGCCGGGGAGGTGGAGCACGAGCGCACGTGTTAGGACCCGAAAGATGGTGAACTATGC
CTGGGCAGGGCGAAGCCAGAGGAAACTCTGGTGGAGGTCCGTAGCGGTCCTGACGTGCAAATCGGTCGTC
CGACCTGGGTATAGGGGCGAAAGACTAATCGAACCATCTAGTAGCTGGTTCCCTCCGAAGTTTCCCTCAG
GATAGCTGGCGCTCTCGCAGACCCGACGCACCCCGCCACGCAGTTTTATCCGGTAAAGCGAATGATTAG
AGGTCTTGGGGCCGAAACGATCTCAACCTATTCTCAAACTTTAAATGGGTAAGAAGCCCGGCTCGCTGGC
GTGGAGCCGGGCGTGGAATGCGAGTGCCTAGTGGGCACTTTTGGTAAGCAGAACTGGCGCTGCGGGATG
AACCGAACGCCGGGTTAAGGCGCCCGATGCCGACGCTCATCAGACCCCAGAAAAGGTGTTGGTTGATATA
GACAGCAGGACGGTGGCCATGGAAGTCGGAATCCGCTAAGGAGTGTGTAACAACTCACCTGCCGAATCAA
CTAGCCCTGAAAATGGATGGCGCTGGAGCGTCGGGCCCATACCCGGCCGTCGCCGGCAGTCGAGAGTGGA
CGGGAGCGGCGGGGCGGCGCGCGCGCGCGCGTGTGGTGTGCGTCGGAGGGCGGCGGCGGCGGCGGCG
GCGGGGGTGTGGGGTCCTTCCCCGCCCCCCCCCACGCCTCCTCCCCTCCTCCCGCCCACGCCCCGCT
CCCCGCCCCGGAGCCCCGCGGACGCTACGCCGCGACGAGTAGGAGGGCCGCTGCGGTGAGCCTTGAAGC
CTAGGGCGCGGGCCCGGGTGGAGCCGCCGCAGGTGCAGATCTTGGTGGTAGTAGCAAATATTCAAACGAG
AACTTTGAAGGCCGAAGTGGAGAAGGGTTCCATGTGAACAGCAGTTGAACATGGGTCAGTCGGTCCTGAG
AGATGGGCGAGCGCCGTTCCGAAGGGACGGGCGATGGCCTCCGTTGCCCTCGGCCGATCGAAAGGGAGTC
GGGTTCAGATCCCCGAATCCGGAGTGGCGGAGATGGGCGCCGCGAGGCGTCCAGTGCGGTAACGCGACCG
ATCCCGGAGAAGCCGGCGGGAGCCCCGGGGAGAGTTCTCTTTTCTTTGTGAAGGGCAGGGCGCCCTGGAA
TGGGTTCGCCCCGAGAGAGGGGCCCGTGCCTTGGAAAGCGTCGCGGTTCCGGCGGCGTCCGGTGAGCTCT
CGCTGGCCCTTGAAAATCCGGGGAGAGGGTGTAAATCTCGCGCCGGGCCGTACCCATATCCGCAGCAGG
TCTCCAAGGTGAACAGCCTCTGGCATGTTGGAACAATGTAGGTAAGGGAAGTCGGCAAGCCGGATCCGTA
ACTTCGGGATAAGGATTGGCTCTAAGGGCTGGGTCGGTCGGGCTGGGGCGCGAAGCGGGGCTGGGCGCGC
GCCGCGGCTGGACGAGGCGCCGCCGCCCCCCCACGCCCGGGGCACCCCCTCGCGGCCCTCCCCCGCCC
CACCCCGCGCGCCGCTCGCTCCCTCCCCGCCCGCGCCCTCTCTCTCTCTCTCCCCGCTCCCCGT
CCTCCCCCCTCCCCGGGGGAGCGCCGCGTGGGGCGGCGGCGGGGGAGAAGGGTCGGGCGGCAGGGC
CGGCGGCGGCCCGCCGCGGGGCCCCGGCGGCGGGGCACGGTCCCCGCGAGGGGGCCCGGGCACCCGG
GGGGCCGGCGGCGGCGGCGACTCTGGACGCGAGCCGGGCCCTTCCCGTGGATCGCCCCAGCTGCGGCGGG
CGTCGCGGCCGCCCCGGGGAGCCCGGCGGGCGCCGGCGCGCCCCCCCCCCACCCCACGTCTCGTCGCG
CGCGCGTCCGCTGGGGCGGGAGCGGTCGGGCGGCGGCGGTCGGCGGGCGGCGGGCGGGGCGGTTCGT
CCCCCCGCCCTACCCCCCGGCCCCGTCCGCCCCCGTTCCCCCCTCCTCCTCGGCGCGCGGCGGCGGCG
GCGGCAGGCGGCGGAGGGGCCGCGGGCCGGTCCCCCCGCCGGGTCCGCCCCGGGGCCGCGGTTCCGCG

Figure 8 (cont'd)

```
CGGCGCCTCGCCTCGGCCGGCGCCTAGCAGCCGACTTAGAACTGGTGCGGACCAGGGGAATCCGACTGTT
TAATTAAAACAAAGCATCGCGAAGGCCCGCGGCGGGTGTTGACGCGATGTGATTTCTGCCCAGTGCTCTG
AATGTCAAAGTGAAGAAATTCAATGAAGCGCGGGTAAACGGCGGGAGTAACTATGACTCTCTTAAGGTAG
CCAAATGCCTCGTCATCTAATTAGTGACGCGCATGAATGGATGAACGAGATTCCCACTGTCCCTACCTAC
TATCCAGCGAAACCACAGCCAAGGGAACGGGCTTGGCGGAATCAGCGGGGAAAGAAGACCCTGTTGAGCT
TGACTCTAGTCTGGCACGGTGAAGAGACATGAGAGGTGTAGAATAAGTGGGAGGCCCCCGGCGCCCCCC
GGTGTCCCCGCGAGGGGCCCGGGCGGGGTCCGCCGGCCCTGCGGGCCGCCGGTGAAATACCACTACTCT
GATCGTTTTTTCACTGACCCGGTGAGGCGGGGGGGCGAGCCCCGAGGGGCTCTCGCTTCTGGCGCCAAGC
GCCCGGCCGCGCGCCGGCCGGGCGCGACCCGCTCCGGGGACAGTGCCAGGTGGGGAGTTTGACTGGGGCG
GTACACCTGTCAAACGGTAACGCAGGTGTCCTAAGGCGAGCTCAGGGAGGACAGAAACCTCCCGTGGAGC
AGAAGGGCAAAAGCTCGCTTGATCTTGATTTTCAGTACGAATACAGACCGTGAAAGCGGGGCCTCACGAT
CCTTCTGACCTTTTGGGTTTTAAGCAGGAGGTGTCAGAAAAGTTACCACAGGGATAACTGGCTTGTGGCG
GCCAAGCGTTCATAGCGACGTCGCTTTTTGATCCTTCGATGTCGGCTCTTCCTATCATTGTGAAGCAGAA
TTCACCAAGCGTTGGATTGTTCACCCACTAATAGGGAACGTGAGCTGGGTTTAGACCGTCGTGAGACAGG
TTAGTTTTACCCTACTGATGATGTGTTGTTGCCATGGTAATCCTGCTCAGTACGAGAGGAACCGCAGGTT
CAGACATTTGGTGTATGTGCTTGGCTGAGGAGCCAATGGGGCGAAGCTACCATCTGTGGGATTATGACTG
AACGCCTCTAAGTCAGAATCCCGCCCAGGCGGAACGATACGGCAGCGCCGCGGAGCCTCGGTTGGCCTCG
GATAGCCGGTCCCCCGCCTGTCCCCGCCGGCGGGCCGCCCCCCCCTCCACGCGCCCCGCGCGCGGGA
GGGCGCGTGCCCCGCCGCGCGCCGGGACCGGGGTCCGGTGCGGAGTGCCCTTCGTCCTGGGAAACGGGGC
GCGGCCGGAGAGGCGGCCGCCCCCTCGCCCGTCACGCACCGCACGTTCGTGGGGAACCTGGCGCTAAACC
ATTCGTAGACGACCTGCTTCTGGGTCGGGGTTTCGTACGTAGCAGAGCAGCTCCCTCGCTGCGATCTATT
GAAAGTCAGCCCTCGACACAAGGGTTTGTC
```

METHOD OF MONITORING RNASE L ACTIVITY

This application is a National Stage application of International Application No. PCT/US2017/031379, filed May 5, 2017, which claims the benefit of U.S. patent application Ser. No. 62/332,729, filed May 6, 2016, and U.S. patent application Ser. No. 62/344,104, filed Jun 1, 2016.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "50691_Seqlisting.txt", which was created on Oct. 30, 2018 and is 78,644 bytes in size. The subject matter of the Sequence Listing is incorporated herein in its entirety by reference.

FIELD OF THE DISCLOSURE

The present disclosure relates, in general, to a method for generating chimeric DNA derived from RNase L cleavage products in a sample, and detection of such RNase L cleavage products for diagnosis and treatment of inflammation and infection in a subject.

BACKGROUND

RNase L is a mammalian endoribonuclease regulated by the action of double stranded DNA (dsRNA) and interferons (IFNs) α/β/λ, which induce the intracellular synthesis of a specific RNase L activator, 2-5A (Silverman R H., J Virol 81(23):12720-12729, 2007). RNA cleavage is thought to account for all biological functions of the RNase L•2-5A complex, including innate immunity during the IFN response (Malathi et al., Nature 448(7155):816-819, 2007; Li et al., Proc Natl Acad Sci USA 105(52):20816-821, 2008), and regulation of cell cycle (Al-Ahmadi et al., Oncogene 28(15):1782-1791, 2009), proliferation (Brennan-Laun et al., J Biol Chem 289(48):33629-33643, 2014), adipocyte differentiation (Fabre 0, et al., Cell Death Differ 19(9): 1470-1481, 2012), and apoptosis (Zhou et al., EMBO J 16(21):6355-6363, 1997). RNase L inhibits translation by site-specific cleavage of 18S and 28SrRNA (Cooper et al., Nucleic Acids Res 42(8):5202-5216, 2014) and activates transcription and the NLRP3 inflammasome by releasing signaling RNA fragments (Malathi, 2007, supra; Chakrabarti A, et al. Cell Host Microbe 17(4):466-477, 2015; Malathi et al. Proc Natl Acad Sci USA 102(41): 14533-14538, 2005). These mechanisms complement or operate in parallel with posttranscriptional gene control via regulated decay of some mRNAs, including myogenic regulatory factor MyoD (Bisbal et al., Mol Cell Biol 20(14): 4959-4969, 2000), components of IFN signaling ISG43 and ISG15 (Li et al; J Biol Chem 275(12):8880-8888, 2000), translation-inhibiting kinase PKR (Khabar et al., J Biol Chem 278(22):20124-20132, 2003), cathepsin E gastric protease (Li, 2008, supra), 3'-UTR-binding protein HuR (Al-Ahmadi, supra), as well as ribosomal and mitochondrial protein-encoding mRNAs (Andersen et al., RNA Biol 6(3): 305-315, 2009; Le Roy et al., J Biol Chem 276(51):48473-48482, 2001; Chandrasekaran et al., Biochem Biophys Res Commun 325(1):18-23, 2004).

A recent RNA-sequencing (RNA-seq) study described some of the direct targets of RNase L (Cooper, supra). Cleavages were reported for 18S rRNA and U6 snRNA, however, the experiment was designed to detect predominantly ribosomal reads and the direct impact of RNase L on mRNAs was not defined. Structural and biochemical studies found that RNase L cleaves RNA at the consensus sequence UN^N (N=A, U, G, or C; ^ is the cleavage location) (Washenberger et al., Virus Res 130(1-2):85-95, 2007; Han et al., Science 343(6176):1244-1248, 2014; Wreschner et al., Nature 289(5796):414-417, 1981). The UN^N motifs are abundant in all mammalian RNAs, suggesting that RNase L may degrade every mRNA it encounters, which would surprisingly contrast regulation of RNase L by the highly specific stimuli dsRNA, IFNs, and 2-5A.

One of the programs responsible for sensing dsRNA in mammalian cells is the 2',5'-oligoadenylate (2-5A) pathway. The production and effects of 2-5A were first documented in interferon (IFN)-treated and virus-infected cells, so a large body of research focused initially on its antiviral effects. Studies that followed found that 2-5A is also important for antibacterial innate immune defense, as well as more broadly, for cell growth and homeostasis. The mechanisms responsible for these phenomena remain fundamentally unclear.

Mammalian cells contain a transmembrane RNase L homolog, a kinase/RNase Ire1, which drives the unfolded protein response and regulated Ire1-dependent decay (RIDD) (Han, supra; Kimmig P, et al., eLife 1:e00048, 2012). The cleavage consensus sequence of Ire1 (UG^C) is similarly relaxed, however Ire1 targets only specific mRNAs. The specificity is achieved by colocalization with cognate mRNAs at the ER membrane (Aragón et al., Nature 457(7230):736-740, 2009). For the cytosolic enzyme RNase L, such a specificity mechanism is not documented. To understand mammalian gene regulation by RNase L, the inventors mapped RNase L-cleavage products in human cells. It is shown here that RNase L does not cleave all cellular transcripts and the results identify biologically related groups of Rnase L targets.

RNase L is a key immune protein, which is linked to many diseases. However, there are no assays for convenient detection of RNase L activity in clinic, which is a major and heretofore unsolved problem. The only existing method uses a large amount of material analyzed by an RNA-gel or a BioAnalyzer chip. In these previous methods, the readout is based on analyzing cleavage of 28S rRNA, which may result from RNase L or other enzymes, and occurs only upon prolonged RNase L activation. Detection of RNase L gene expression level is also not suitable for measuring RNase L activity because RNase L is a regulated enzyme and its levels do not report on activity. Therefore, existing methods are not only insensitive and thus incompatible with standard clinical samples, but also unreliable.

SUMMARY OF THE DISCLOSURE

The present disclosure describes the first method that enables qPCR detection of RNase L activity in human cells. The high amplification of PCR enables accuracy and excellent sensitivity for use in conventional patient samples, such as blood, as well as possibly in saliva and other biological fluids or solid samples.

In various embodiments, the disclosure provides a method for detecting an RNase L cleavage product comprising, a) isolating total RNA or small RNAs from a sample; b) ligating an adapter to the RNAs from the sample, wherein the adapter ligates to RNAs that have been cleaved by RNase L; c) generating cDNA by reverse-transcription of the RNA-adapter ligation product using a reverse transcription primer that is complementary to at least a portion of the ligated adapter polynucleotide; d) contacting the cDNA with a first primer comprising nucleotides identical to at least a portion of the sequence of RNase L-cleaved RNA and having one or more bases identical to the adapter but not to the isolated RNA, and a second primer that is identical to at least a portion of the reverse transcription primer; e) amplifying the cDNA encoding the RNA-adapter product; and f) detecting the amplified product of (e) to detect an RNase L cleaved RNA product. Optionally, the method comprises a step of isolating the amplified product prior to the detecting step. Additionally, in various embodiments, the ligation step (b) can be carried out prior to the isolation step (a).

In various embodiments, the detecting is performed by a method selected from the group consisting of PCR, qPCR, sequencing and DNA gel electrophoresis. In some embodiments, the detecting is by qPCR.

In various embodiments, the small RNAs are less than 200 nucleotides.

In various embodiments, the first primer has no nucleotides/bases identical to the adapter. In some embodiments, the first primer has from 1 to 10 bases identical to the adapter, but not to the RNA cleaved by RNase L. In other embodiments, the first primer comprises 1, 2 or 3 nucleotides that are complementary to the adapter sequence.

In various embodiments, the first and second primers are between 15 and 30 nucleotides, e.g., 15, 16, 17, 18, 19, 20, 21, 22, 23, 24, 25, 26, 27, 28, 29 or 30 nucleotides. In various embodiments, the first and second primers comprise between 17 and 24 nucleotides each, optionally between 19 and 22 nucleotides each.

In various embodiments, the adapter has a 2',3' cyclic phosphate or 3'-phosphate and is ligated to the 5'-OH-end of RNA cleaved by RNase L. In various embodiments, the adapter is ligated to the isolated RNA with RtcB RNA ligase. In other embodiments, the adapter is ligated to the RNA after removal of the 2'-3' cyclic phosphate, e.g., with T4 RNA ligase or T4 RNA ligase 2. In other embodiments, the ligase is a 2',3'-cyclic phosphate compatible polynucleotide ligase. In other embodiments, the ligase is a 3'-phosphate compatible polynucleotide ligase.

In various embodiments, the RNA cleaved by RNase L is labeled with a detectable label. In various embodiments, the detectable label is a radionuclide, a fluorophore or enzyme. In one embodiment, the detectable label is biotin. In some embodiments, the detectable label is horseradish peroxidase or alkaline phosphatase.

In various embodiments, the product is detected using fluorophore- or enzyme-conjugated biotin binding proteins.

In various embodiments, the ligation adapter has at its 5' end at least 1 nucleotide that is identical to the 3' end of the first primer, optionally wherein the nucleotides are RNA. In various embodiments, the ligation adapter has the polynucleotide sequence 5'-GAUCGUCGGACTG-TAGAACTCTGAAC-3' (SEQ ID NO: 1), wherein the first 6 nucleotides are RNA and the remainder of the nucleotides are DNA.

In various embodiments, the amplification is by PCR or by qPCR.

In various embodiments, the RNase L cleavage product results from cleavage of RNA by RNase L between two nucleotides that follow a U or a C RNA base, optionally wherein the sequence is UN^N or CN^N.

In various embodiments, the subject is a mammal, including humans, other primates, cows, horses, sheep, pigs, cats, dogs, hamsters, mice and rats and non-mammals, such as fowl and other birds. In various embodiments, the subject is a human.

In various embodiments, the sample is isolated from a subject. In various embodiments, the sample is any bodily fluid, blood, plasma, cerebrospinal fluid, urine, saliva, cells or tissue. In various embodiments, the sample is blood or plasma.

In various embodiments, the subject is suspected of suffering from or is suffering from inflammation or an ongoing immune response or an interferon response. In various embodiments, the inflammation is a result of an infection, an autoimmune disease, asthma or cancer. In various embodiments, the infection is a bacterial infection or a viral infection. In some embodiments, the subject is suspected of suffering from a disorder with cell loss, such as a neurodegenerative disorder or diabetes.

In various embodiments, the RNase L cleavage product is a tRNA, rRNA, Y-RNA, snoRNA, vtRNA or U-RNA. In various embodiments, the RNase L cleavage product is tRNA-His, tRNA-Gln, tRNA-Glu, tRNA-Lys or tRNA-Pro. In various embodiments, the RNase L cleavage product is RNY1, RNY3, RNY4 or RNY5. In some embodiments, the RNase L cleavage product is VTRNA1 or VTRNA2. In some embodiments, the RNase L cleavage product is RNU1, SNORA1 or SNORD16. In some embodiments, the RNase L cleavage product is 28S rRNA or 18S rRNA.

Also contemplated herein is a chimeric polynucleotide comprising an RNase L cleavage product and an adapter polynucleotide sequence. In various embodiments, the RNA portion of the chimeric polynucleotide is the RNA product of the RNase L cleavage that is 5' of the cleavage nucleotide. In various embodiments, the RNA portion of the chimeric polynucleotide is the RNA product of the RNase L cleavage that is 3' of the cleavage nucleotide.

In various embodiments of the chimeric polynucleotide, the RNase L cleavage product is a tRNA, rRNA, Y-RNA, snoRNA, vtRNA or U-RNA. In some embodiments, the RNase L cleavage product in the chimeric polynucleotide is tRNA-His, tRNA-Gln, tRNA-Glu, tRNA-Lys, tRNA-Pro, RNY1, RNY3, RNY4, RNY5, VTRNA1, VTRNA2, RNU1, SNORA1, SNORD16, 28S rRNA or 18S rRNA.

In various embodiments of the chimeric polynucleotide, the adapter is from 15 to 40 nucleotides. In various embodiments of the chimeric polynucleotide, the adapter polynucleotide is RNA or an RNA/DNA composite or mixed polynucleotide. In various embodiments of the chimeric polynucleotide, the adapter has the polynucleotide sequence 5'-GAUCGUCGGACTGTAGAACTCTGAAC-3'(SEQ ID NO: 1), wherein the first 6 nucleotides (underlined) are RNA and the remainder of the nucleotides are DNA.

In various embodiments, the RNase L cleavage product ligated to an adapter polynucleotide to form a chimeric polynucleotide, and for use in the method is a His-tRNA-GUG-1-9 cleaved at residue 36, i.e., His-tRNA-GUG-1-9 (36); His-tRNA-GUG-1-9 variant sequence (37), Pro-tRNA-UGG-3-5 (34); Pro-tRNA-UGG-2-1 (34); Pro-tRNA-UGG-1-1 (34); His-tRNA-GUG-2-1 (36); Pro-tRNA-UGG-1-1 (34); His-tRNA-GUG-2-1 (36); His-tRNA-GUG-2-1 (37); Lys-tRNA-UUU-10-1 (36); Lys-tRNA-UUU-3-5 (36); Glu-tRNA-CUC-2-1 (36); Glu-tRNA-UUC-4-2 (36); Leu-tRNA-UAA-1-1 (50 or 51); Gln-UUG-1-1 (36); Thr-tRNA-UGU-2-1 (34); Val-tRNA-UAC-1-2 Gln-tRNA-UUG-1-1 (36); Gln-tRNA-CUG-4-2 (36); Gln-tRNA-CUG-1-5 (36); RNY4 (27); RNY5 (26 or 29 or 30 or 31); RNY1 (32); RNY3 (32); vtRNA1-2 (36); SNORA45A also known as SNORA3A (78); 28S rRNA (4032), 18S rRNA or RNU6-1.

In various embodiments, the RNase L cleavage product contemplated starts at a nucleotide 5' to the cleavage site and ends at the cleavage nucleotide, i.e., including the cleavage nucleotide.

Provided in the disclosure is a method for detecting inflammation in a subject comprising detecting RNase L cleavage products according to the methods herein, wherein an increase in overall RNase L cleavage products or in one or more RNase L cleavage products indicates the subject is suffering from inflammation.

Also provided in the disclosure is a method for detecting an interferon response or immune response in a subject comprising detecting RNase L cleavage products according to the methods herein, wherein an increase in overall RNase L cleavage products or in one or more RNase L cleavage products indicates the subject is suffering from an interferon response or an immune response.

Also contemplated is a method for treating inflammation in a subject comprising detecting RNase L cleavage products in a subject according to the methods herein, wherein an increase in overall RNase L cleavage products or in one or more RNase L cleavage products indicates the subject is suffering from inflammation, and administering an anti-inflammatory agent to the subject.

In various embodiments, the disclosure provides a method for treating an interferon response or an immune response in a subject comprising detecting RNase L cleavage products in a subject according to the methods herein, wherein an increase in overall RNase L cleavage products or in one or more RNase L cleavage products indicates the subject is suffering from an interferon response or an immune response, and administering a therapeutic agent to the subject.

The disclosure contemplates a method for determining efficacy of an anti-inflammatory treatment in a subject suffering from inflammation comprising detecting RNase L cleavage products in a subject according to the methods herein before and after administration of an anti-inflammatory agent, wherein a decrease in overall RNase L cleavage products or in one or more RNase L cleavage products after administration indicates the anti-inflammatory agent is reducing inflammation in the subject.

The disclosure further contemplates a method for determining efficacy of an anti-immune response or anti-interferon treatment in a subject suffering from an immune response or interferon response comprising detecting RNase L cleavage products in a subject according to the methods herein before and after administration of a therapeutic agent, wherein a decrease in overall RNase L cleavage products or in one or more RNase L cleavage products after administration indicates the therapeutic agent is reducing the immune response or interferon response in the subject.

In various embodiments, the therapeutic agent is an anti-inflammatory agent, a cytoprotective agent, a cytotoxic agent, or an agent that induces inflammation. Other anti-inflammatory and therapeutic agents contemplated herein are discussed in more detail in the Detailed Description.

In various embodiments, the inflammation, immune response or interferon response is a result of an infection, an autoimmune disease, asthma or cancer. In various embodiments, an increase in RNase L cleavage products is indicative of aberrant signaling in the immune response pathway. Exemplary infections, autoimmune diseases, and cancers contemplated herein are discussed further in the Detailed Description.

In various embodiments of the methods, the RNase L cleavage product is a tRNA, rRNA, Y-RNA, snoRNA or vtRNA.

In various embodiments of the methods, the RNase L cleavage product is tRNA-His, tRNA-Gln, tRNA-Glu, tRNA-Lys tRNA-Pro, RNY1, RNY3, RNY4, RNY5, VTRNA1, VTRNA2, RNU1, SNORA1, SNORD16, 28S rRNA or 18S rRNA.

It is understood that each feature or embodiment, or combination, described herein is a non-limiting, illustrative example of any of the aspects of the invention and, as such, is meant to be combinable with any other feature or embodiment, or combination, described herein. For example, where features are described with language such as "one embodiment", "some embodiments", "certain embodiments", "further embodiment", "specific exemplary embodiments", and/or "another embodiment", each of these types of embodiments is a non-limiting example of a feature that is intended to be combined with any other feature, or combination of features, described herein without having to list every possible combination. Such features or combinations of features apply to any of the aspects of the invention. Where examples of values falling within ranges are disclosed, any of these examples are contemplated as possible endpoints of a range, any and all numeric values between such endpoints are contemplated, and any and all combinations of upper and lower endpoints are envisioned.

Other features and advantages of the present disclosure will become apparent from the following detailed description. It should be understood, however, that the detailed description and the specific examples, while indicating preferred embodiments of the disclosure, are given by way of illustration only, because various changes and modifications within the spirit and scope of the disclosure will become apparent to those skilled in the art from this detailed description.

BRIEF DESCRIPTION OF THE FIGURES

FIG. 4A shows enrichment for tRNA-His GUG-1-9 cleavage, and shows the most common cleavage residue is at nucleotide 36 (SEQ ID NO: 343). FIG. 4B shows enrichment for RNY1 cleavage (SEQ ID NO: 344). FIG. 4C shows enrichment for RNY3 cleavage (SEQ ID NO: 345). FIG. 4D shows enrichment for RNY4 cleavage (SEQ ID NOs: 346 and 347). FIG. 4E shows enrichment for RNY5 cleavage (SEQ ID NO: 348). FIG. 4F represents a qPCR analysis showing that stimulation with PolyI:C significantly increased the number of tRNA His-GUG-36-2 cleavage products compared to non-stimulated cells. Relative amounts of the His-GUG-36 product were calculated using the ΔΔCt method.

Figure 5A:
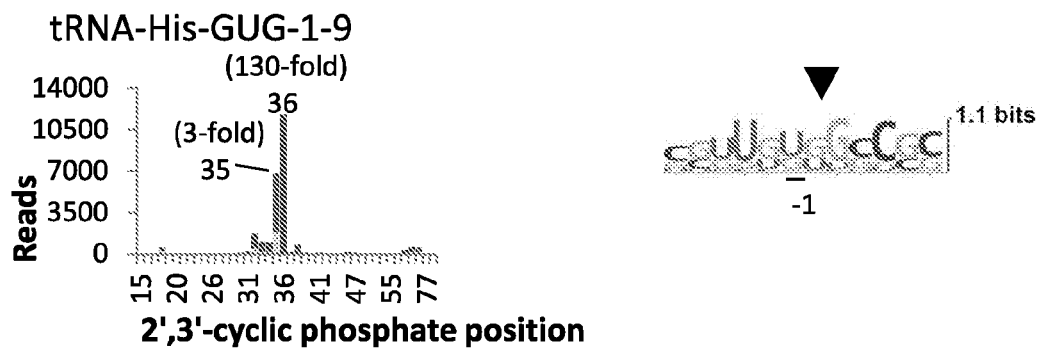
Figure 5B:
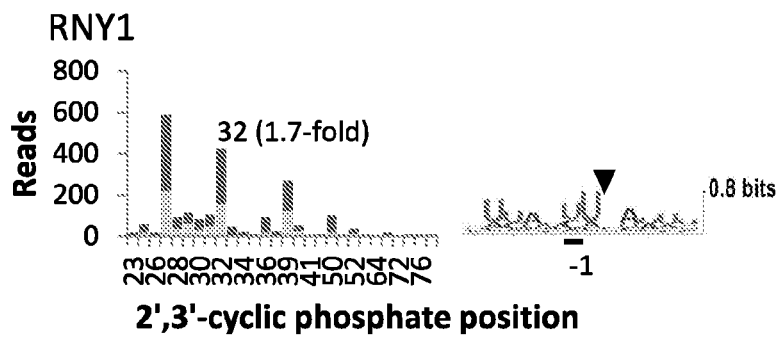
Figure 5C:
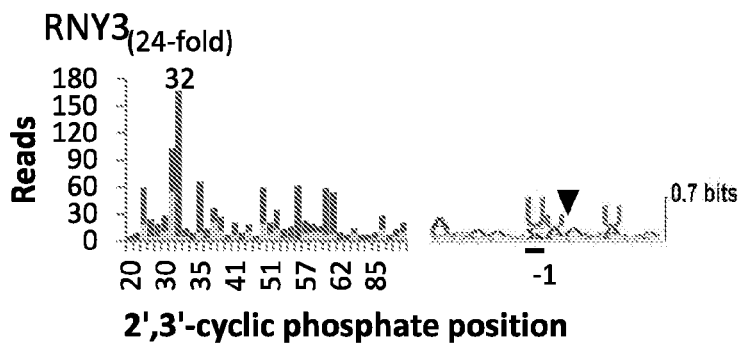
Figure 5D:
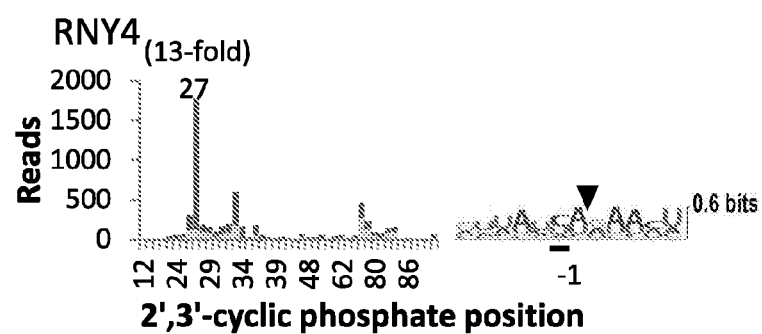
Figure 5E:
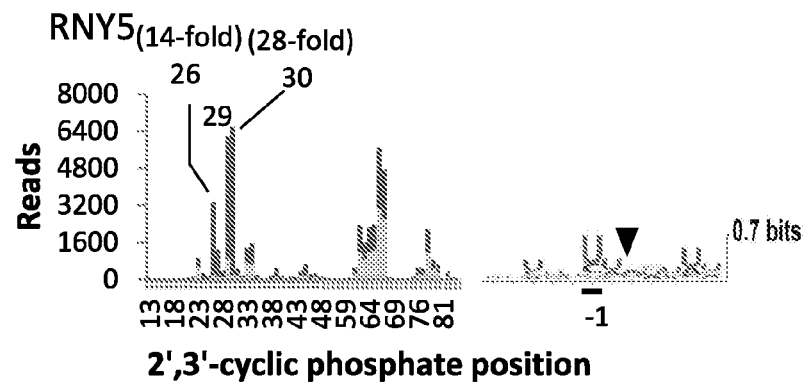

FIGS. 5A-5E show the cleavage nucleotide profile of RNLoe cells. FIG. 5A shows enrichment for tRNA-His GUG-1-9 cleavage (SEQ ID NO: 343). FIG. 5B shows enrichment for RNY1 cleavage (SEQ ID NO: 349). FIG. 5C shows enrichment for RNY3 cleavage(SEQ ID NO: 350). FIG. 5D shows enrichment for RNY4 cleavage(SEQ ID NO: 347). FIG. 5E shows enrichment for RNY5 cleavage(SEQ ID NO: 351) .

Figure 6A:
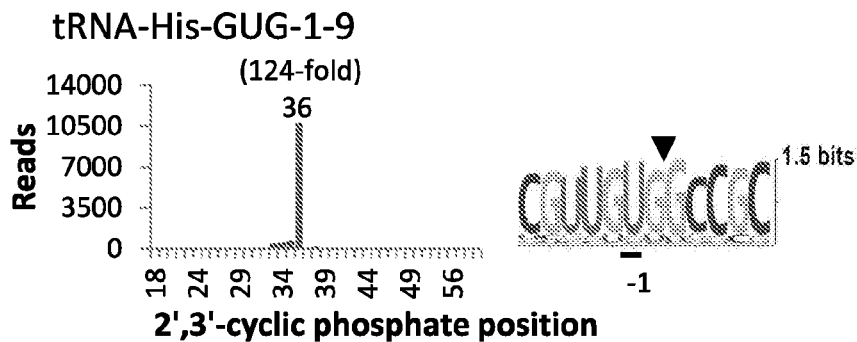
Figure 6B:
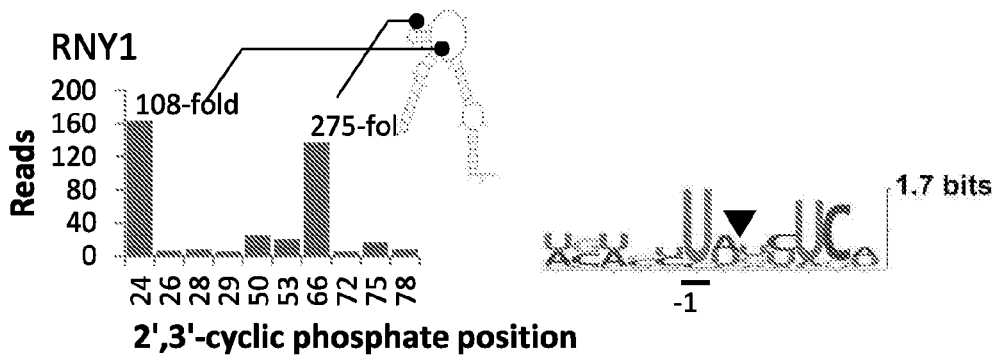
Figure 6C:
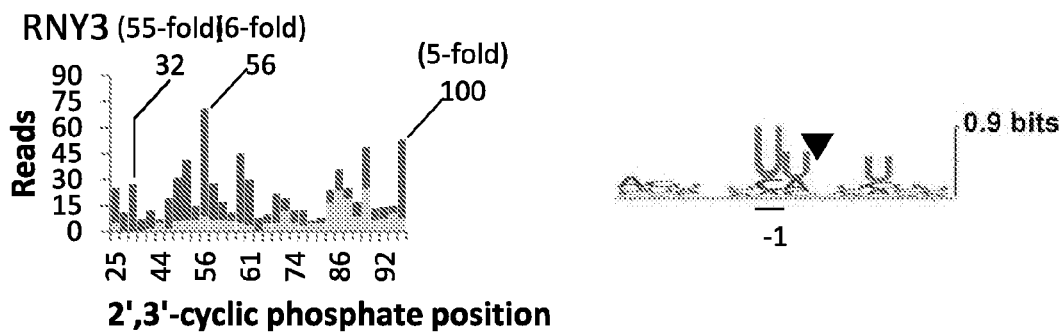
Figure 6D:
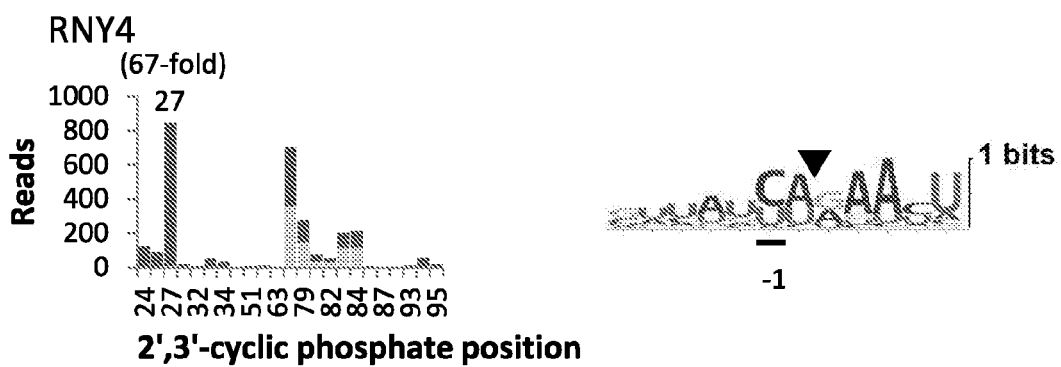
Figure 6E:
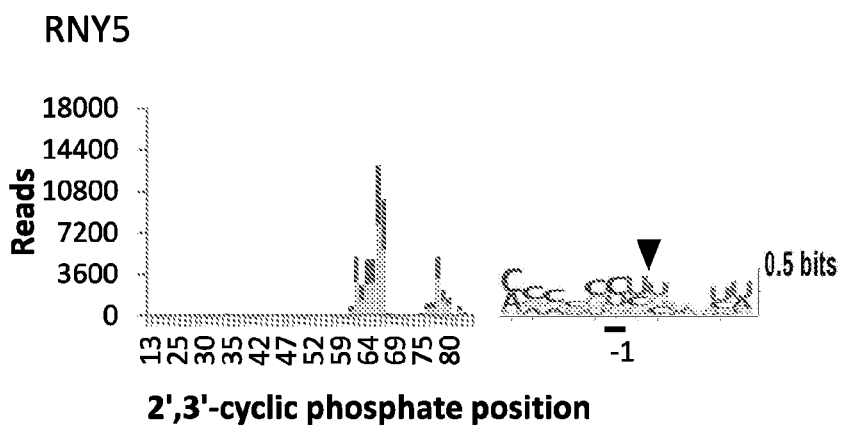

FIGS. 6A-6E show the cleavage nucleotide profile of the T47D cells stimulated with 1 µM 2-5A for 1 minute. FIG. 6A shows enrichment for tRNA-His GUG-1-9 cleavage (SEQ ID NO: 352). FIG. 6B shows enrichment for RNY1 cleavage (SEQ ID NO: 353). FIG. 6C shows enrichment for RNY3 cleavage (SEQ ID NO: 354). FIG. 6D shows enrichment for RNY4 cleavage (SEQ ID NO: 347). FIG. 6E shows enrichment for RNY5 cleavage (SEQ ID NO: 355).

FIG. 7 represents RNase L cleavage product sequences obtained by the sequencing methods herein and their identification by Genbank Accession No.

FIG. 8 represents RNase L 28S ribosomal RNA. RNase L cleavage site nucleotide 4032 is underlined and shaded.

Figure 9:
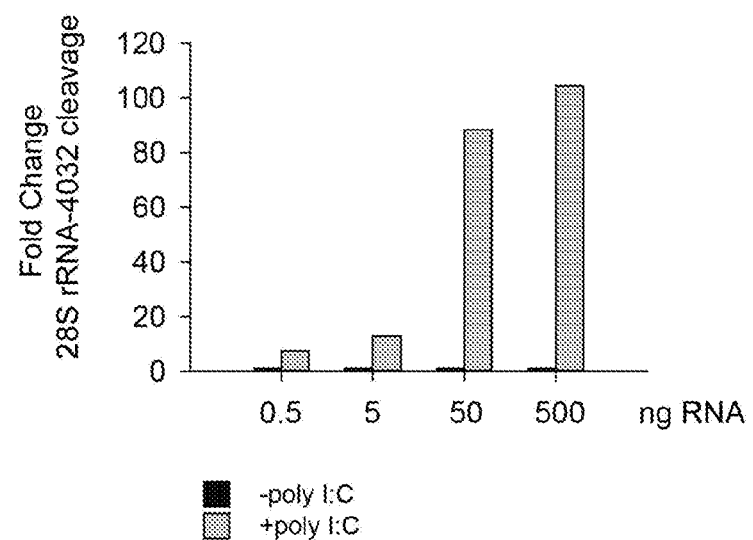

FIG. 9 shows that RNase L cleavage product 28S rRNA is detectable from purified total RNA from poly I:C treated or untreated HeLa cells.

DETAILED DESCRIPTION OF THE DISCLOSURE

The present disclosure is based on the discovery that RNase L cleavage products are useful for detection of inflammation, interferon response or cellular stress in a subject as the rate of production of RNase L cleavage products increases during an immune response and in response to inflammation. Described herein is an RNA-seq approach for transcriptome-wide profiling of human RNA decay by RNase L. This approach reveals direct mammalian targets of the dsRNA/OAS/2-5A/RNase L cascade.

Definitions

Unless otherwise stated, the following terms used in this application, including the specification and claims, have the definitions given below.

As used in the specification and the appended claims, the indefinite articles "a" and "an" and the definite article "the" include plural as well as singular referents unless the context clearly dictates otherwise.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, or 0.05% of a given value or range. Whenever the term "about" or "approximately" precedes the first numerical value in a series of two or more numerical values, it is understood that the term "about" or "approximately" applies to each one of the numerical values in that series.

Definition of standard chemistry terms may be found in reference works, including Carey and Sundberg, Advanced Organic Chemistry, 3$^{rd}$ Edition, Vols. A and B (Plenum Press, New York 1992). The practice of the present disclosure may employ, unless otherwise indicated, certain conventional methods of synthetic organic chemistry, mass spectrometry, preparative and analytical chromatography, protein chemistry, biochemistry, recombinant DNA technology and pharmacology, within the skill of the art. See, e.g., T. E. Creighton, Proteins: Structures and Molecular Properties (W.H. Freeman and Company, 1993); A. L. Lehninger, Biochemistry (Worth Publishers, Inc., 4$^{th}$ Edition, 2004); Sambrook, et al., Molecular Cloning: A Laboratory Manual (2$^{nd}$ Edition, 1989); Methods In Enzymology (S. Colowick and N. Kaplan eds., Academic Press, Inc.); Remington's Pharmaceutical Sciences, 18$^{th}$ Edition (Easton, Pa.: Mack Publishing Company, 1990).

All publications, patents and patent applications cited herein, whether supra or infra, are hereby incorporated by reference in their entirety.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

Conventional notation is used herein to portray polypeptide and peptide sequences: the left-hand end of a polypeptide or peptide sequence is the amino-terminus; the right-hand end of a polypeptide sequence is the carboxyl-terminus.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, genomic RNA, mRNA, non-coding RNAs, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P—NH2) or a mixed phosphoramidate-phosphodiester oligomer. Peyrottes et al. (1996) Nucleic Acids Res. 24: 1841-8; Chaturvedi et al. (1996) Nucleic Acids Res. 24: 2318-23; Schultz et al. (1996) Nucleic Acids Res. 24: 2966-73. A phosphorothioate linkage can be used in place of a phosphodiester linkage. Braun et al. (1988) J. Immunol. 141: 2084-9; Latimer et al. (1995) Molec. Immunol. 32: 1057-1064. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. Reference to a polynucleotide sequence (such as referring to a SEQ ID NO) also includes the complement sequence.

The following are non-limiting examples of polynucleotides: a gene or gene fragment, exons, introns, genomic RNA, mRNA, tRNA, rRNA, snoRNA, vtRNA, Y-RNA, microRNA, ribozymes, cDNA, U-RNA, snRNAs, exRNAs, piRNAs and scaRNAs, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracil, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support.

The term "small RNA" refers to small non-coding RNA molecules of approximately 20-250 nucleotides. Small RNAs include siRNA, microRNA, tRNA, rRNA, snoRNA, Y-RNA, U-RNA, snRNAs, exRNAs, piRNAs and scaRNAs.

In certain embodiments, rRNA cleavage products may not be small RNA, but may have a number of bases larger than that of a small RNA, e.g., the 28S rRNA cleavage product or 18S rRNA cleavage product.

The phrase "substantially homologous" or "substantially identical" in the context of two nucleic acids or polypeptides, generally refers to two or more sequences or subsequences that have at least 40%, 60%, 80%, 90%, 95%, 96%, 97%, 98% or 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of either or both comparison biopolymers. It is understood that RNA and DNA sequences can be considered identical, but have the RNA base substituted for the DNA base, or vice versa, in the sequence. For example, an RNA sequence is considered identical to a DNA sequence if it has a U in place of a T in the same position.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Natl. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by visual inspection. Alignment is also measured using such algorithms as PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Another algorithm that is useful for generating multiple alignments of sequences is Clustal W (Thompson et al., *Nucleic Acids Research* 22: 4673-4680, 1994). Another example of algorithm that is suitable for determining percent sequence identity and sequence similarity is the BLAST algorithm, which is described in Altschul et al., *J. Mol. Biol.* 215:403-410, 1990. Software for performing BLAST analyses is publicly available through the National Center for Biotechnology Information.

"Encoding" refers to the property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA, snoRNa, vtRNA, U-RNA, Y-RNA, snRNAs, exRNAs, piRNAs and scaRNAs and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Primer" as used herein refers to short fragments of single stranded DNA or RNA (15-30 nucleotides in length) that are complementary to polynucleotide sequences that flank the target region of interest. The purpose of PCR primers is to provide a "free" 3'-OH group to which the DNA polymerase can add dNTPs. It is contemplated that a primer used herein can be 15, 16, 17, 18, 19, 20, 21, 22, 3, 24, 25, 26, 27, 28, 29 or 30 nucleotides in length. In various embodiments the primers are from 17-24 nucleotides or from 19-22 nucleotides.

"Adapter" as used herein refers to a known or predetermined polynucleotide sequence linked to the polynucleotide (DNA or RNA) fragment to be amplified, and is often used either to extend the polynucleotide fragment or tag it in a certain way. Additional description of adapters contemplated herein is found below in the Detailed Description.

The term "chimeric polynucleotide" as used herein refers to an RNase L cleavage product that is ligated to an adapter polynucleotide. In various embodiments, the RNA portion of the chimeric polynucleotide is the RNA product of the RNase L cleavage that is 5' of the cleavage nucleotide. In various embodiments, the RNA portion of the chimeric polynucleotide is the RNA product of the RNase L cleavage that is 3' of the cleavage nucleotide. In various embodiments, the adapter is an RNA molecule, or an RNA/DNA composite molecule.

"Amplification" as used herein refers to DNA replication of one or more DNA or RNA templates during a PCR reaction to copy the polynucleotide sequences and exponentially increase the copy number of target polynucleotide sequences.

The term "domain" as used herein refers to a contiguous sequence on a polynucleotide primer of the disclosure. The term "region" as used herein refers to a contiguous or non-contiguous sequence on a target or non-target polynucleotide. The term "target polynucleotide" as used herein refers to a polynucleotide from which extension by a polymerase is desired, or to which a polynucleotide primer combination of the disclosure is intended to hybridize. Thus, a "non-target polynucleotide" is a polynucleotide from which extension by a polymerase is not desired, or is less desirable than that of a target polynucleotide, or to which a polynucleotide primer combination of the disclosure is intended to hybridize with less specificity than a target polynucleotide.

"Appropriate conditions" as used herein refers to those conditions that are determined by one of ordinary skill in the art, and generally refer to nucleic acid hybridization conditions. One of skill in the art will understand that "appropriate conditions" with respect to hybridization depend on factors including but not limited to length of a polynucleotide, relative G+C content, salt concentration and hybridization temperature. Additional hybridization conditions are discussed herein below.

"Specifically hybridize" as used herein means that a polynucleotide will hybridize substantially or only with a specific nucleotide sequence or a group of specific nucleotide sequences under stringent hybridization conditions when the sequence is present in a complex mixture of DNA or RNA. Stringent hybridization conditions are described herein below. One or more nucleic acids are said to be "sufficiently complementary" when, given a certain set of hybridizing conditions, the one or more nucleic acids hybridize to each other. Accordingly, one or more nucleic acids are said to be "not sufficiently complementary" when, given a certain set of hybridizing conditions, the one or more nucleic acids do not hybridize to each other. "Fully complementary" or "perfectly complementary" as used herein means that a polynucleotide is 100% complementary to another polynucleotide.

A "mutation" as used herein refers to one or more nucleotides in a polynucleotide that differ from one or more corresponding nucleotides in a wild-type polynucleotide. Examples of a mutation include but are not limited to an insertion, a deletion, a substitution and an inversion.

A polynucleotide is said to "overlap" with another polynucleotide when one or more bases of each polynucleotide can hybridize to the same one or more bases of a target or non-target polynucleotide. By way of example, where a first polynucleotide is complementary to a region in a target nucleic acid and a second polynucleotide is complementary to all or part of the same region in the target polynucleotide, the first polynucleotide and the second polynucleotide are said to overlap.

A "unique polynucleotide sequence" as used herein refers to a sequence in a polynucleotide primer that is not complementary to a sequence in either a polynucleotide primer, a target polynucleotide or a non-target polynucleotide.

"Percent complementarity" or "% complementary" as used herein refers to a relative number of bases in a polynucleotide that are complementary to a number of bases in another polynucleotide. Thus, in one non-limiting example, if 18 out of 20 nucleotides in a polynucleotide primer of the disclosure are perfectly complementary to a target polynucleotide, the polynucleotide primer is said to be 90% complementary to the target polynucleotide.

As used herein, "isolated" refers to a polynucleotide composition that is removed from its native environment. Thus, an isolated biological material is free of some or all cellular components, i.e., components of the cells in which the native material occurs naturally (e.g., cytoplasmic or membrane component). In one aspect, an RNase L cleavage product, RNA-adapter product or other polynucleotide is deemed isolated if it is present in a cell extract or supernatant. In the case of nucleic acid molecules, an isolated nucleic acid includes a PCR product, an isolated mRNA, a cDNA, or a restriction fragment.

"Purified" as used herein refers to an RNase L cleavage product or other polynucleotide that has been isolated under conditions that reduce or eliminate the presence of unrelated materials, i.e., contaminants, including endogenous materials from which the composition is obtained. By way of example, and without limitation, a purified polynucleotide is substantially free of host cell or culture components, including tissue culture or cell proteins and non-specific pathogens. In various embodiments, purified material substantially free of contaminants is at least 50% pure; at least 60%, at least 70%, at least 80%, at least 90%, at least 95%, at least 96%, at least 97%, at least 98% or even at least 99% pure. Purity can be evaluated by chromatography, gel electrophoresis, immunoassay, composition analysis, biological assay, and other methods known in the art.

"Inflammation," "immune response" or "inflammatory response" as used herein refers to any and all such inflammatory reactions including, but not limited to, immune-related responses and/or allergic reactions to a physical, chemical, or biological stimulus. An immune response may involve the humoral immune system as well as the innate and adaptive immune systems, including activation of B cells, T cells, other lymphocytes, monocytes, neutrophils, eosinophils and basophils, production of antibodies, cytokines and chemokines and other immunologic response mechanisms well-known to those of skill in the art. Diseases or disorders that result from or cause inflammation are readily known to a person of skill in the art, and are described in additional detail below.

RNase L Cleavage Products

It is disclosed herein that some of the primary targets for RNase L activity are small RNAs, including, but not limited to tRNAs, Y RNAs, rRNAs, snoRNAs, vtRNAs, snRNAs, U-RNAs, exRNAs, piRNAs and scaRNAs. Larger RNAs such as 28S rRNA or 18S rRNA are also contemplated. RNase L cleavage products refers to an RNA polynucleotide that has been cleaved by RNase L. For example, the characteristic RNase L cleavage product results from cleavage of RNA by RNase L between two nucleotides that follow a U or a C RNA base, optionally wherein the sequence is UN^N or CN^N. The RNase L cleavage product can be between 20-70 nucleotides in length. It is contemplated that two types of RNase L cleavage products can exist, e.g., those RNA that contain RNA polynucleotides that are 5' of the cleavage site or those that contain RNA that is 3' of the cleavage site.

Transfer RNA (tRNA) are specific types of RNA that deliver amino acids to the protein ribosome as indicated by the three-nucleotide sequence codon in the mRNA. tRNA names include the anti-codon sequence which may be written as DNA or RNA (example: His-tRNA-GUG-1-9 and His-tRNA-GTG-1-9 both indicate the same sequence). Exemplary tRNAs that are cleaved by RNase L are indicated below in the 5' to 3' direction. All tRNAs are post-transcriptionally modified with a short 3'-oligonucleotide tail with sequence 'CCA'. This tail is noted in the sequences below, but is not always found in public sequence databases. The positions of the main RNase L cleavage sites are parenthetically indicated and underlined in the sequence.

His-tRNA-GUG-1-9 (36)

(SEQ ID NO: 2)
GCCGUGAUCGUAUAGUGGUUAGUACUCUGCGUUGUGGCCGCAGCAACCUC
GGUUCGAAUCCGAGUCACGGCACCA

His-tRNA-GUG-1-9 variant sequence (37); A single 5'-G is post-transcriptionally added to His-tRNA in vivo and is italicized below. This residue is sometimes not annotated in public databases.

(SEQ ID NO: 3)
GGCCGUGAUCGUAUAGUGGUUAGUACUCUGCGUUGUGGCCGCAGCAACCU
CGGUUCGAAUCCGAGUCACGGCACCA

Pro-tRNA-UGG-3-5 (34):

(SEQ ID NO: 4)
GGCUCGUUGGUCUAGGGGUAUGAUUCUCGCUUUGGGUGCGAGAGGUCCCG
GGUUCAAAUCCCGGACGAGCCCCCA

Pro-tRNA-UGG-2-1 (34):

(SEQ ID NO: 5)
GGCUCGUUGGUCUAGGGGUAUGAUUCUCGGUUUGGGUCCGAGAGGUCCCG
GGUUCAAAUCCCGGACGAGCCCCCA

Pro-tRNA-UGG-1-1 (34):

(SEQ ID NO: 6)
GGCUCGUUGGUCUAGUGGUAUGAUUCUCGCUUUGGGUGCGAGAGGUCCCG
GGUUCAAAUCCCGGACGAGCCCCCA

His-tRNA-GUG-2-1 (36):

(SEQ ID NO: 7)
GCCAUGAUCGUAUAGUGGUUAGUACUCUGCGCUGUGGCCGCAGCAACCUC
GGUUCGAAUCCGAGUCACGGCACCA

His-tRNA-GUG-2-1 variant sequence (37); the 5'-G is added to this tRNA as with variant His-tRNA-GUG-1-9:

(SEQ ID NO: 8)
GGCCAUGAUCGUAUAGUGGUUAGUACUCUGCGCUGUGGCCGCAGCAACCU
CGGUUCGAAUCCGAGUCACGGCACCA

Lys-tRNA-UUU-10-1 (36):

(SEQ ID NO: 9)
GCCAGGAUAGUUCAGGUGGUAGAGCAUCAGACUUUUAACCUGAGGGUUCA
GGGUUCAAGUCUCUGUUUGGGCGCCA

Lys-tRNA-UUU-3-5 (36):

(SEQ ID NO: 10)
GCCCGGAUAGCUCAGUCGGUAGAGCAUCAGACUUUUAAUCUGAGGGUCCA
GGGUUCAAGUCCCUGUUCGGGCGCCA

Glu-tRNA-CUC-2-1 (36):

(SEQ ID NO: 11)
UCCCUGGUGGUCUAGUGGUUAGGAUUCGGCGCUCUCACCGCCGCGGCCCG
GGUUCGAUUCCCGGUCAGGAAACCA

Glu-tRNA-UUC-4-2 (36):

(SEQ ID NO: 12)
UCCCUGGUGGUCUAGUGGCUAGGAUUCGGCGCUUUCACCGCCGCGGCCCG
GGUUCGAUUCCCGGUCAGGGAACCA

Leu-tRNA-UAA-1-1 (50,51):

(SEQ ID NO: 13)
ACCAGGAUGGCCGAGUGGUUAAGGCGUUGGACUUAAGAUCCAAUGGACAU
AUGUCCGCGUGGGUUCGAACCCCACUCCUGGUACCA

Gln-UUG-1-1 (36):

(SEQ ID NO: 14)
GGUCCCAUGGUGUAAUGGUUAGCACUCUGGACUUUGAAUCCAGCGAUCCG
AGUUCAAAUCUCGGUGGGACCUCCA

Thr-tRNA-UGU-2-1 (34):

(SEQ ID NO: 15)
GGCUCCAUAGCUCAGUGGUUAGAGCACUGGUCUUGUAAACCAGGGGUCGC
GAGUUCGAUCCUCGCUGGGGCCUCCA

Val-tRNA-UAC-1-2 (35):

(SEQ ID NO: 16)
GGUUCCAUAGUGUAGUGGUUAUCACGUCUGCUUUACACGCAGAAGGUCCU
GGGUUCGAGCCCCAGUGGAACCA

Gln-tRNA-UUG-1-1 (36):

(SEQ ID NO: 17)
GGUCCCAUGGUGUAAUGGUUAGCACUCUGGACUUUGAAUCCAGCGAUCCG
AGUUCAAAUCUCGGUGGGACCUCCA

Gln-tRNA-CUG-4-2 (36):

(SEQ ID NO: 18)
GGUUCCAUGGUGUAAUGGUAAGCACUCUGGACUCUGAAUCCAGCGAUCCG
AGUUCGAGUCUCGGUGGAACCUCCA

Gln-tRNA-CUG-1-5 (36):

(SEQ ID NO: 19)
GGUUCCAUGGUGUAAUGGUUAGCACUCUGGACUCUGAAUCCAGCGAUCCG
AGUUCAAAUCUCGGUGGAACCUCCA

Other RNase L cleavage products include Y RNA and others, including those set out below, as indicated by the RNA type and in parentheses is the predicted RNase L cleavage site.

RNY4 (27):

(SEQ ID NO: 20)
GGCUGGUCCGAUGGUAGUGGGUUAUCAGAACUUAUUAACAUUAGUGUCAC

UAAAGUUGGUAUACAACCCCCACUGCUAAAUUUGACUGGCUUUUU

RNY5 (26,29,30,31):

(SEQ ID NO: 21)
AGUUGGUCCGAGUGUUGUGGGUUAUUGUUAAGUUGAUUUAACAUUGUCUC

CCCCCACAACCGCGCUUGACUAGCUUGCUGUUUU

RNY1 (32):

(SEQ ID NO: 22)
GGCUGGUCCGAAGGUAGUGAGUUAUCUCAAUUGAUUGUUCACAGUCAGUU

ACAGAUCGAACUCCUUGUUCUACUCUUUCCCCCCUUCUCACUACUGCACU

UGACUAGUCUUUU

RNY3 (32):

(SEQ ID NO: 23)
GGCUGGUCCGAGUGCAGUGGUGUUUACAACUAAUUGAUCACAACCAGUUA

CAGAUUUCUUUGUUCCUUCUCCACUCCCACUGCUUCACUUGACUAGCCUU

UU vtRNA1-2 (36):

(SEQ ID NO: 24)
GGGCUGGCUUUAGCUCAGCGGUUACUUCGAGUACAUUGUAACCACCUCUC

UGGGUGGUUCGAGACCCGCGGGUGCUUUCCAGCUCUUUU

SNORA45A; also known as SNORA3A (78):

(SEQ ID NO: 25)
ATCGAGGCTAGAGTCACGCTTGGGTATCGGCTATTGCCTGAGTGTGCTAG

AGTCCTCGAAGAGTAACTGCTGACCTTATTCACTGGCTGTGGGCCTTATG

GCACAGTCAGTCACCAGGTTAGAGACATGC 28S ribosomal RNA (4032): Sequence set out in FIG. 8.

In the assay, reference genes are used as control for the reaction for normalizing the qPCR data. Two reference genes contemplated include His-tRNA-GUG-1-9 and RNU6-1.

His-tRNA-GUG-1-9 exhibits low levels of a cyclic phosphate-bearing cleavage at position 18/19 that is independent of RNase L. Additionally, U6 RNA (RNU6-1) has a naturally occurring terminal 2'-3' cyclic phosphate that is captured by RtcB ligation. After reverse transcription it can be amplified using ligation specific primers or primers that anneal within the cDNA.

RNU6-1:

(SEQ ID NO: 26)
GTGCTCGCTTCGGCAGCACATATACTAAAATTGGAACGATACAGAGAAGA

TTAGCATGGCCCCTGCGCAAGGATGACACGCAAATTCGTGAAGCGTTCCA

TATTTT

There are many copies of RNU6 throughout the genome which may differ in sequence from that given above and may be used as reference genes. Similarly, other U-RNAs (U1, U4, U5) are detected in the RNA sequencing datasets and can be used as reference genes.

Contemplated herein is a chimeric polynucleotide comprising an RNase L cleavage product and an adapter sequence. In various embodiments, the RNase L cleavage product comprises an RNA polynucleotide that is cleaved by RNase L at any one of the following nucleotides.

Predicted cleavage sites for tRNA-His include, but are not limited to, nucleotides 31, 32, 33, 33, 34, 35 and 36.

Predicted cleavage sites for RNY1 include, but are not limited to, nucleotides 21, 22, 23, 24, 25, 26, 27, 28, 32, 33, 39, 50, 53, 66, 75, 77 and 78.

Predicted cleavage sites for RNY3 include, but are not limited to, nucleotides 25, 26, 31, 32, 35, 44, 49, 50, 52, 55, 56, 57, 60, 61, 86, 100

Predicted cleavage sites for RNY4 include, but are not limited to, nucleotides 26, 27, 33, Predicted cleavage sites for RNY5 include, but are not limited to, nucleotides 24, 26, 27, 29, 30, 31, 34, 35, 64, 65, 66, 67 and 68.

It is contemplated that the RNase L cleavage products produced by cleavage at any one of the sites above are useful in a chimeric polynucleotide as described herein.

In various embodiments, the RNase L cleavage product ligated to an adapter polynucleotide to form a chimeric polynucleotide, and for use in the methods herein is a His-tRNA-GUG-1-9 cleaved at residue 36, i.e., His-tRNA-GUG-1-9 (36); His-tRNA-GUG-1-9 variant sequence (37), Pro-tRNA-UGG-3-5 (34); Pro-tRNA-UGG-2-1 (34); Pro-tRNA-UGG-1-1 (34); His-tRNA-GUG-2-1 (36); Pro-tRNA-UGG-1-1 (34); His-tRNA-GUG-2-1 (36); His-tRNA-GUG-2-1 (37); Lys-tRNA-UUU-10-1 (36); Lys-tRNA-UUU-3-5 (36); Glu-tRNA-CUC-2-1 (36); Glu-tRNA-UUC-4-2 (36); Leu-tRNA-UAA-1-1 (50 or 51); Gln-UUG-1-1 (36); Thr-tRNA-UGU-2-1 (34); Val-tRNA-UAC-1-2; Gln-tRNA-UUG-1-1 (36); Gln-tRNA-CUG-4-2 (36); Gln-tRNA-CUG-1-5 (36); RNY4 (27); RNY5 (26 or 29 or 30 or 31); RNY1 (32); RNY3 (32); vtRNA1-2 (36); SNORA45A also known as SNORA3A (78); 28S rRNA or 18S rRNA or RNU6-1.

Primers

Detection of the RNA cleavage product is carried out, in various embodiments, by quantitative PCR using primers specific for the ligated RNA cleavage product and a standard primer specific for the adapter sequence that is ligated to the RNase L cleavage product, or for a sequence introduced during reverse transcription. It is contemplated that for the assay herein, primers, e.g., first primers, share at least 90% sequence identity to the RNase L cleavage product sequence are useful in the assay. It is contemplated that the first primer sequences shares at least 90%, 91%, 92%, 93%, 94%, 95%, 96%, 97%, 98% or 99% sequence identity to the RNase L cleavage product sequence.

It is contemplated herein that the second primer shares at least 90% sequence identity with the reverse transcription primer used in the assay, or to a sequence tag that is part of the reverse transcription primer, e.g., at least 90%, 91%, 92%, 93%, 94%, 95%, 96%, 97%, 98% or 99% sequence identity. In one embodiment, the second primer is identical to all or part of the sequence tag and has a portion of the polynucleotide that is complementary to the adapter.

It is contemplated that a primer used herein can be between 15-30 nucleotides, e.g., 15, 16, 17, 18, 19, 20, 21, 22, 3, 24, 25, 26, 27, 28, 29 or 30 nucleotides in length. In various embodiments the primers are from 17-24 nucleotides or from 19-22 nucleotides.

The following primers useful in the methods are named by RNA specificity, cleavage site, and the number of bases that are identical to bases in the 5' end of the adapter. These bases are underlined in the primer sequences. In some cases, the first and/or second bases that are identical to the adapter are also identical to the sequence of the uncleaved RNA and the second and/or third base that matches the adapter provides specificity.

Primers that have become standards by having low background in qPCR are marked with an asterisk.

Primers specific for RNY4 include: RNY4-27-3:

GATGGTAGTGGGTTATCAGAT*. (SEQ ID NO: 27)

Primers specific for RNY5 include: RNY5-30-1:

GTGTTGTGGGTTATTGTTAG; (SEQ ID NO: 28)

RNY5-30-2:

GTGTTGTGGGTTATTGTTAGA* (SEQ ID NO: 29)

and RNY5-30-4:

GTGTTGTGGGTTATTGTTAGATC. (SEQ ID NO: 30)

Primers for His-tRNA-GUG-1-9: His-GUG-36-3:

GTTAGTACTCTGCGTTGTGGAT (SEQ ID NO: 31)

and His-GUG-36-2:

GTTAGTACTCTGCGTTGTGA*. (SEQ ID NO: 32)

Primers for reference genes/cleavage sites include His-GUG-18-2:

GGCCGTGATCGTATAGTGGGAT (SEQ ID NO: 33)

or His-GUG-18-1:

GGCCGTGATCGTATAGTGGGA*. (SEQ ID NO: 34)

Primers for 28S rRNA include: 28S rRNA-4032-2:

CGGGGTCCGCCGGCCCTGGA. (SEQ ID NO: 35)

RNU6 primers: It has been reported in the literature (Tazi et al., Mol Cell Biol. March; 13(3):1641-1650, 1993) that U6 may have variable length U-tails with a 2'-3' cyclic phosphate. In light of this, it may be advantageous to use internal U6 primers for qPCR rather using a primer that amplifies RNU6 at the ligation site.

RNU6 Forward:

GCTTCGGCAGCACATATACTA; (SEQ ID NO: 36)

RNU6 Rev:

CGAATTTGCGTGTCATCCTTG; (SEQ ID NO: 37)

RNU6 Forward2 (if amplifying at the ligation site):

CGTGAAGCGTTCCATATTTTGA. (SEQ ID NO: 38)

Primers specific for other RNase L cleavage products can be developed based on the predicted cleavage site of a known polynucleotide sequence for an RNase L cleavage site, e.g., for snoRNAs, vtRNAs or other RNAs that can be cleaved by RNase L as described herein.

Amplification Reaction

In order to carry out the amplification/extension reaction of the method herein, certain adapters, transcriptases and polynucleotides are used. Below are exemplary sequences and methods for amplification and extension of the target RNA useful to detect RNase L cleavage products.

Ligating the RNA to an adapter creates a unique sequence that can be detected by hybridizing an oligonucleotide which base pairs at the junction of a specific RNA and the adapter. Such a system could be employed in microarray technology and detection achieved by using a fluorescently labeled oligonucleotide that specifically hybridizes to the RNA-adapter chimera. Using different colored fluorescent groups would allow comparison of multiple sample types on one chip (example: disease versus normal) and fluorescence intensity reports on abundance of the RNA fragments.

In various embodiments, the adapter is from about 15-40 nucleotides, from about 15-30 nucleotides, from about 20-40 nucleotides, from about 20-30 nucleotides, or from about 25-35 nucleotides. In various embodiments, the adapter is 15, 16, 17, 18, 19, 20, 21, 22, 23, 24, 25, 26, 27, 2, 29, 30, 31, 32, 33, 34, 35, 36, 37, 38, 39 or 40 nucleotides.

In various embodiments, the adapter polynucleotide is RNA or an RNA/DNA composite or mixed polynucleotide. In various embodiments, the adapter polynucleotide has a 5'-OH group and the underlined bases are RNA. The remaining bases are DNA. An exemplary ligation adapter has the following sequence: GAUCGUCGGACTGTAGAACTCT-GAAC (SEQ ID NO: 1).

When the adapter is ligated by RtcB RNA ligase, some of the bases at the 5' end have to be RNA. It is contemplated that 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 nucleotides on the 5' end are RNA. It is also possible for the entire adapter to be composed of RNA.

In one embodiment, the sequence of the ligation adapter is the reverse complement of Illumina's RA5 adapter from the Illumina small RNA TruSeq kit. The adapter sequence can changed if desired.

When RNase L cleaves an RNA at a single site it generates one RNA product with a 2'-3' cyclic phosphate and one RNA product with a 5'-OH. The 3'-side of the cleavage product has the 5'-OH and can be detected with RtcB ligation and qPCR. RtcB is an RNA ligase that ligates an RNA bearing a 2'-3' cyclic phosphate or 3'-phosphate to an RNA with a 5'-hydroxyl (5'-OH). The current protocol utilized *E. coli* RtcB, but RtcB from other organisms may be used. However, RtcB from some species, but not *E. coli*, requires an accessory protein called archease for efficient ligation. Other RNA ligases, such as *Arabidopsis* tRNA ligase (ATL), ligate RNA with 2'-3' cyclic phosphate to RNA with 5'-OH. In the case of ATL, an additional phosphatase treatment would be required to remove a 2'-phosphate on the ligated RNA. RtcB catalyzed ligation is dependent on $Mn^{2+}$ ions and GTP. It is contemplated that $Mn^{2+}$ salts could be used in the buffer.

Contemplated herein is use of other species RtcB in combination with an archease for ligation. In various embodiments, the ligation buffer for RtcB comprises $Mn^{2+}$ ions and GTP. It is contemplated that $Mn^{2+}$ salts could be used in the buffer.

Contemplated herein is the use of *Arabidopsis* tRNA ligase for ligation. The method requires a phosphatase treatment to remove 2' phosphate on the RNA after ligation to permit subsequent steps.

In a variation of the method, detecting the 3'-side of the cleavage site requires an adapter oligonucleotide with a 3'-phosphate. A key difference of this detection system is that it requires RNA-specific reverse transcription primers.

Cleavage site specificity during qPCR comes from a primer that matches the adapter and has 1-3 bases that match the RNase L-cleavage site of interest.

In various embodiments, the Reverse Transcriptase (RT) primer having the following sequence, (SEQ ID NO: 39)
TCCCTATCAGTGATAGAGAGTTCAGAGTTCTACAGTCCG, is composed entirely of DNA. The underlined region base pairs with part of the ligation adapter. The non-underlined region introduces sequence to 1) make a longer cDNA that brings the qPCR amplicon size closer to conventional qPCR amplicon lengths and 2) to introduce a binding site for the qPCR reverse primer. This non-underlined region is from the Tet-operator. The non-underlined portion of the sequence can be altered if desired.

In some embodiments, the qPCR reverse primer, TCCCTATCAGTGATAGAGAG (SEQ ID NO: 40), is a standard DNA oligo and is used in combination with primers for detecting specific cleavage sites during qPCR.

In one aspect, the method uses SYBR green detection of qPCR products. In another aspect, the method uses Taqman based qPCR detection. Taqman probes allow for the detection of multiple RNA fragments in a single qPCR reaction and increase the throughput of the assay. In such an assay, the forward PCR primer binds in the 5' region of the RNA sequence, the reverse primer binds to the adapter sequence and the Taqman probe hybridizes at the junction of the adapter and the RNA sequence.

With regard to the extension/amplification reaction mixture used in the methods provided herein, the polymerase is any enzyme whose central function is to catalyze the polymerization of a new polynucleotide, such as DNA or RNA, against an existing template. In exemplary aspects, the polymerase is a DNA polymerase (e.g., DNA polymerase I, DNA polymerase II, DNA polymerase III holoenzyme, DNA polymerase IV), an RNA polymerase (e.g., RNA polymerase I, RNA polymerase II, RNA polymerase III, T7 RNA polymerase), or a combination thereof. In some aspects, the polymerase is a strand displacement polymerase, e.g., a polymerase which exhibits strand displacement activity. In some aspects, the strand displacement activity is limited. In alternative aspects, the strand displacement activity is strong. In some aspects, the polymerase is a DNA polymerase with limited or strong strand displacement activity (e.g., Klenow fragment of DNA polymerase I, Klenow fragment of DNA polymerase I (exo-), Phi29 DNA polymerase, Sequenase™ II, Large fragment of Bst DNA polymerase, DisplaceAce™ DNA polymerase, MMLV reverse transcriptase, AMV reverse transcriptase, Taq DNA polymerase (5' exo-), Vent DNA polymerase, Ven(exo-) DNA polymerase, Deep Vent DNA polymerase, Deep Vent DNA polymerase (exo-), and the like. The polymerase in some aspects is any of those described further in the section entitled "Kits."

With regard to the amplification/extension reaction mixture used in the methods provided herein, the free nucleotides may be any free (e.g., unpolymerized) nucleotides known in the art, including, but not limited to any of the naturally-occurring nucleotides, dATP, dCTP, dTTP, dUTP, dGTP, and modified forms discussed herein, e.g., nucleotides comprising modified bases, nucleotides of any of the modified polynucleotides. The free nucleotides in some aspects is a combination of different types of nucleotides optionally in admixture. In exemplary aspects, the combination comprises dATP, dCTP, dTTP, dGTP, and optionally, dUTP. In some aspects, the combination comprises each type of free nucleotide in equal amounts, e.g., equimolar amounts. In some aspects, one or more free nucleotides is in limiting amounts, and in some aspects, the one or more free nucleotides present in the extension reaction mixture is the complementary nucleotide of internal replication blocking group R. By "limiting amounts" as used herein refers to an amount which is at least or about 2-fold, at least or about 3-fold, at least or about 5 fold, at least or about 10-fold, at least or about 20-fold, at least or about 30-fold, at least or about 50-fold, at least or about 100-fold less than the amount of another free nucleotide.

Detectable Labels

In various embodiments, the RNase L cleavage product is labeled with a detectable label. The detectable label may be any of those known in the art, including, but not limited to, a radioisotope (e.g., $^{133}$Barium, $^{109}$Cadmium, $^{57}$Co, $^{60}$Co, $^{152}$Europium, $^{54}$Mn, $^{22}$Na, $^{65}$Zn, $^{99m}$Technetium, $^{90}$Strontium, $^{204}$Thallium, $^{14}$C, $^{32}$P, $^{125}$I), a fluorophore (e.g., hydroxycoumarin, methoxycoumarin, aminocoumarin, FAM, 6-carboxyfluorescein, Alexa fluor 430, Alexa fluor 488, Alexa fluor 532, Alexa fluor 546, Alexa fluor 555, Alexa fluor 568, Alexa fluor 594, Alexa fluor 633, Alexa fluor 660, Alexa fluor 680, fluorescein, HEX, Cy3, TRITC, R-phycoerythrin, rhodamine red-X, tamara, Rox, texas red, allophycocyanin, TruRed, Cy2, Cy3, Cy3.5 581, Cy5, Cy5.5, Cy7) and an elemental particle (e.g., gold, copper, silver), and other molecules that are detectable when enzymatically activated or bound to another particle, e.g., biotin-streptavidin, alkaline phosphatase, horseradish peroxidase, and other chromogenic or chemiluminescent molecules.

In some aspects, the detectable label permits quantification of the amplification/extension reaction product. In exemplary aspects, the amount of radioactivity of a radioisotope or the amount of fluorescence of a fluorophore correlates with the amount of the reaction product or correlates with the length of the reaction product.

A detectable label or marker for compositions includes one which is detectable only when it binds to the product of an extension reaction. In one aspect, the label or marker produces a signal when bound to the extension product. In another aspect the probe or marker signal is quenched when the probe or marker is not bound to the extension product.

In some aspects, the label or marker is a molecular beacon comprises a quenching moiety, which prevents emission of a signal from the detectable label until the probe or molecular beacon is hybridized to its target, e.g., hybridized to the extension reaction product. Quenching moieties are known in the art. See, for example, Livak et al., Genome Res. 4: 357-362 (1995). Non-limiting examples of quenchers contemplated for use in practice of the methods of the invention include Black Hole Quencher 1, Black Hole Quencher-2, Iowa Black FQ, Iowa Black RQ, Zen quencher, and Dabcyl. G-base.

Quantitative PCR (qPCR) methods allow the estimation of the amount of a given sequence present in a sample. Quantitative PCR is an established tool for DNA quantification that measures the accumulation of DNA product after each round of PCR amplification.

Hybridization Conditions

In some embodiments, the primers, e.g., the reverse transcription primer, first (1) and second primer (2), hybridize to RNase L cleavage product or adapter or other polynucleotide sequence herein under stringent conditions in the absence of a template polynucleotide. "Stringent conditions" as used herein can be determined empirically by the worker of ordinary skill in the art and will vary based on, e.g., the length of the primer, complementarity of the primer, concentration of the primer, the salt concentration (i.e., ionic strength) in the hybridization buffer, the temperature at which the hybridization is carried out, length of time that hybridization is carried out, and presence of factors that affect surface charge of the polynucleotides. In general, stringent conditions are those in which the polynucleotide is able to bind to its complementary sequence preferentially and with higher affinity relative to any other region on the target. Exemplary stringent conditions for hybridization to its complement of a polynucleotide sequence having 20 bases include without limitation about 50% G+C content, 50 mM salt (Na$^+$), and an annealing temperature of 60° C. For a longer sequence, specific hybridization is achieved at higher temperature. In general, stringent conditions are such that annealing is carried out about 5° C. below the melting temperature of the polynucleotide. The "melting temperature" is the temperature at which 50% of polynucleotides that are complementary to a target polynucleotide in equilibrium at definite ion strength, pH and polynucleotide concentration.

Methods of Use

RNase L cleavage products are involved in the immune response pathway, with increased cleavage products detectable when the immune system is activated, for example, during infection or other instances when there is an ongoing immune response.

It is contemplated that the RNase L cleavage products are detected in a sample isolated from a subject. The sample includes, but is not limited to, any bodily fluid, blood, plasma, cerebrospinal fluid, urine, saliva, cells or tissue.

The subject can be a mammal, including humans, other primates, cows, horses, sheep, pigs, cats, dogs, hamsters, mice and rats, as well as non-mammal animals including fowl and other birds. In various embodiments, the subject is a human.

Provided in the disclosure is a method for detecting inflammation, an immune response or an interferon response in a subject comprising detecting RNase L cleavage products according to the methods herein, wherein an increase in overall RNase L cleavage products or in one or more RNase L cleavage products indicates the subject is suffering from inflammation, an immune response or an interferon response.

Also contemplated herein is a method for treating inflammation in a subject comprising detecting RNase L cleavage products in a subject according to the methods herein, wherein an increase in overall RNase L cleavage products or in one or more RNase L cleavage products indicates the subject is suffering from inflammation and, administering an anti-inflammatory agent to the subject.

The disclosure contemplates a method for determining efficacy of an anti-inflammatory treatment in a subject suffering from inflammation comprising detecting RNase L cleavage products in a subject according to the methods herein before and after administration of an anti-inflammatory agent, wherein a decrease in overall RNase L cleavage products or in one or more RNase L cleavage products after administration indicates the anti-inflammatory agent is reducing inflammation in the subject.

In various embodiments, the inflammation is a result of an infection, an autoimmune disease, asthma or cancer. In some embodiments, the subject is suspected of suffering from a disorder with cell loss, such as a neurodegenerative disorder or diabetes.

Exemplary infections include bacterial, viral, fungal or parasitic infections. Exemplary autoimmune diseases include, but are not limited to, systemic lupus erythematosus, multiple sclerosis, rheumatoid arthritis, connective tissue disease, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Exemplary allergic reactions and conditions include, but are not limited to, asthma (particularly allergic asthma) or other respiratory problems, anaphylaxis, serum sickness, drug reactions, food allergies, insect venom allergies, mastocytosis, allergic rhinitis, hypersensitivity pneumonitis, urticaria, angioedema, eczema, atopic dermatitis, allergic contact dermatitis, erythema multiforme, Stevens-Johnson syndrome, allergic conjunctivitis, atopic keratoconjunctivitis, venereal keratoconjunctivitis, giant papillary conjunctivitis and contact allergies.

Exemplary cancers include, but are not limited to, leukemias, brain tumors (including meningiomas, glioblastoma multiforme, anaplastic astrocytomas, cerebellar astrocytomas, other high-grade or low-grade astrocytomas, brain stem gliomas, oligodendrogliomas, mixed gliomas, other gliomas, cerebral neuroblastomas, craniopharyngiomas, diencephalic gliomas, germinomas, medulloblastomas, ependymomas, choroid plexus tumors, pineal parenchymal tumors, gangliogliomas, neuroepithelial tumors, neuronal or mixed neuronal glial tumors), lung tumors (including small cell carcinomas, epidermoid carcinomas, adenocarcinomas, large cell carcinomas, carcinoid tumors, bronchial gland tumors, mesotheliomas, sarcomas or mixed tumors), prostate cancers (including adenocarcinomas, squamous cell carcinoma, transitional cell carcinoma, carcinoma of the prostatic utricle, or carcinosarcomas), breast cancers (including adenocarcinomas or carcinoid tumors), or gastric, intestinal, or colon cancers (including adenocarcinomas, invasive ductal carcinoma, infiltrating or invasive lobular carcinoma, medullary carcinoma, ductal carcinoma in situ, lobular carcinoma in situ, colloid carcinoma or Paget's disease of the nipple), skin cancer (including melanoma, squamous cell carcinoma, tumor progression of human skin keratinocytes, basal cell carcinoma, hemangiopericytoma and Karposi's sarcoma), lymphoma (including Hogkin's disease and non-Hodgkin's lymphoma), and sarcomas (including osteosarcoma, chondrosarcoma and fibrosarcoma).

In various embodiments, an increase in RNase L cleavage products is indicative of aberrant signaling in the immune response pathway.

In various embodiments of the methods, the RNase L cleavage product is a tRNA, rRNA, Y-RNA, snoRNA or vtRNA.

In various embodiments of the methods, the RNase L cleavage product is tRNA-His, tRNA-Gln, tRNA-Glu, tRNA-Lys tRNA-Pro, RNY1, RNY3, RNY4, RNY5, VTRNA1, VTRNA2, RNU1, SNORA1, SNORD16, 28S rRNA or 18S rRNA.

Antibodies against certain small RNAs, such as RNY4 and RNY5, have been detected in patients that have systemic lupus erythematosus and may also be implicated in Sjogren syndrome. Contemplated herein is a method for diagnosing lupus or determining efficacy of therapy in a lupus patient comprising detecting RNase L cleavage products that are RNY1, RNY4 and/or RNY5 cleavage products. It is believed that the method herein is more sensitive than antibody tests currently used to diagnose lupus or other autoimmune diseases.

It is contemplated that the method is useful in a subject who is receiving treatment for an infection, autoimmune disease, asthma, cancer or a disease in which there is cell loss such as a neurodegenerative disease. The treatment is one that is appropriate for the disorder, e.g., chemo- or radio-therapeutic for cancer, a cancer-specific antibody or antibody drug conjugate, other anti-inflammatory agents, anti-infective agents such as antibiotics, anti-virals, anti-fungals, and specific treatments for autoimmune diseases.

Another potential use of a hybridization based system is assessing RNase L cleavage products in fixed tissue sections or biopsies for clinical samples (as a biomarker or for diagnostic/prognostic indications). Ligation of the adapter and cyclic phosphate RNA would be conducted in situ followed by hybridization of a modified oligonucleotide which base pairs to the RNA-adapter chimera of interest. The modification of the hybridization oligonucleotide is to facilitate detection. For example, this oligonucleotide could be biotinylated for recognition by streptavidin and subsequent probing with enzyme- or fluor-conjugated anti-streptavidin secondary antibodies. Alternatively the oligonucleotide could be fluorescent or directly conjugated to an enzyme such as horse radish peroxidase or alkaline phosphatase for detection with chromogenic substrates.

Example 1

Methods

The methods described below are exemplary methods for carrying out a qPCR-based detection and RNA sequencing-based detection of RNase L cleavage products. The method may be modified to use primers, adapters, transcriptase, ligase, dNTPs and reaction conditions as noted below, and as needed.

Ligation:

Reaction components useful in the ligation reaction include the following: 2-500 ng purified RNA, 30 µM RtcB ligase, 1 U/µL RNase inhibitor, 10 µM ligation adapter, 100 µM GTP, 20 mM HEPES pH 7.5, 2 mM $MnCl_2$, 110 mM NaCl, 4 mM DTT, 2.2% glycerol (carried into the reaction with RtcB and RNase inhibitor). The standard reaction volume is 10 µL with incubation for 1 hour at 37° C.

After incubation 1 µL of 33 mM EDTA is added followed by a brief room temperature incubation (usually 5-10 minutes) giving a final concentration of EDTA of 3 mM. EDTA is added to chelate $Mn^{2+}$ ions that might interfere in downstream steps as well as to stop the ligation reaction.

Generation of cDNA by Reverse Transcription (RT).

1 µL of EDTA quenched ligation reaction is mixed with dNTPs and 10 picomoles (pmol) of RT primer in 10 µL volume. The mixture is incubated at 65° C. for 5 minutes then placed on ice (optional). The remaining components are added for a 20 µL reverse transcription reaction: RT buffer, 0.2 U µL RNase inhibitor, Reverse transcriptase (added last), and $H_2O$ for 20 µL final volume and incubated according to the RT manufacturer's specifications. The protocol herein utilized Multiscribe Reverse Transcriptase (ThermoFisher) and incubated for 10 min at 25° C., 1 hour at 37° C., and 5 min at 95° C. Optionally, the completed RT reaction can be diluted with $H_2O$ and used for as a template for qPCR.

qPCR:

SYBR green based qPCR is carried out using an RNA-cleavage site specific forward primer and the qPCR reverse primer described herein. Forward and reverse primers are used each 400 nM in a 25 µL reaction. RNU6 forward and reverse may be used if assessing RNU6 as a reference gene. qPCR conditions are as follows: 50 cycles followed by a melt curve. In the present analysis, 62° C. annealing/extension temperature seems to provide optimal signal to noise ratio, 60° C. or lower results in higher background and 65° C. precludes robust detection. Annealing/extension at 63° C. may be compatible with robust detection of ligated RNA.

The RNA purification method (e.g., Trizol, miRvana, miRNeasy kits) should retain RNAs <200 nucleotides. It is contemplated that approximately 1 ng to 500 ng or 1000 ng RNA can be used in the assay.

The listed concentrations of reaction components are variable. dNTP concentrations are determined by the reverse transcription kit used.

The amount of RT primer (10 pmol=1 µL of 10 µM primer) is important. The ligation reaction contains 10 µM adapter which is then diluted to 9 µM upon addition of EDTA. The RT reaction as defined above uses 1 µL of the quenched ligation which carries 9 pmol of adapter. The slight molar excess of RT primer relative to adapter in the RT reaction herein was designed to ensure efficient reverse transcription. Substoichiometric amounts of RT primer may result in less efficient reverse transcription of ligated RNAs as the RT primer will more frequently hybridize with non-ligated adapter molecules. Broadly speaking, if more of the ligation reaction is used for reverse transcription, there needs to be a corresponding increase in the amount of RT primer used.

The optional dilution of the reaction with water allows the experimenter to perform multiple qPCR reactions on a single ligation sample. Not diluting the RT reaction may improve sensitivity when working with dilute samples. Primer concentrations may be varied to provide optimal signal.

Preparation of Library for Analysis:

Initially, approximately 500 ng-1 µg miRvana purified small RNAs is ligated to the ligation adapter (5'-GAUCGU-CGGACTGTAGAACTCTGAAC-3'(SEQ ID NO: 1), underlined portion is RNA) using RtcB. It is contemplated that the adaptor has a 3'-desthiobiotin modification. The ligated RNAs are separated from free adapter by resolving on 10% urea PAGE by staining gel and excising all RNA larger than the free adapter. RNA is eluted from gel slices overnight at 4° C. in TE buffer pH 7.5 supplemented with 0.05% Triton X-100. Glycogen is added to RNAs and precipitated with 3 volumes of 100% ethanol and 1/10 volume 3M sodium acetate pH 5.2. The sample is then incubated on dry ice for 30 minutes.

The precipitated RNA is pelleted by centrifugation (16,000×g, 4° C., 25 minutes), supernatant removed and the pellet washed with 1 mL 75% EtOH and centrifuged at 16,000×g, 4° C., 5 min. The supernatant is removed and the pellet air dried and RNA resuspended in 10 uL of $H_2O$. 80% of the recovered RNA is used in a 20 μL reverse transcription reaction containing 2 picomoles of variant RT primer (GTTCAGAGTTCTACAGTCCGACGATC) (SEQ ID NO: 41). The sample is incubated 25° C., 10 minutes at 37° C., 1 hour then a 4° C. hold can be used. It is advisable in the present method to not include a 95° C., 5 minute incubation at the end as the subsequent step requires an intact RNA/cDNA hybrid.

The entire RT reaction is added to 900 μL of 20 mM HEPES, 300 mM NaCl, 0.1% Triton X-100 and magnetic streptavidin beads are added after equilibration in the same buffer. The sample is then incubated 30 minutes at 4° C. with end-over-end rotation and then washed 3× in 1 mL wash buffer (20 mM HEPES, 300 mM NaCl, 0.1% Triton X-100), 10 minutes per wash, then washed 2×1 mL 20 mM HEPES pH 7.5, 100 mM NaCl (no incubation).

After removing all of the previous washes, 10 μL 10 mM biotin is added and incubated 15 minutes at room temperature to elute the RNA/cDNA hybrids. The eluted RNA/cDNA mix are removed from the beads and added to 1 volume (10 μL) 20 mM HEPES pH 7.5, 0.1% Triton X100.

An RA3-phos adapter [RA3-phos adapter (DNA oligo): 5'-phosphate-TGGAATTCTCGGGTGCCAAGG-3'-amino] (SEQ ID NO: 42) is ligated to the 3'-end of cDNA using CircLigase in a 15 μL reaction and incubated 65° C., 1 hour. 50% of the eluted cDNA is used in the reaction with 1 U/μL CircLigase, and 1 μM RA3-phos adapter.

The CircLigase reaction is quenched by adding 1 μL 128 mM EDTA. This step chelates $Mn^{2+}$ which would be mutagenic in subsequent PCR reactions. Phusion DNA polymerase and NEXTFlex Small RNA Barcode Primers are used to PCR amplify 5 μL of the quenched CircLigase reactions, using 15 cycles of PCR.

Libraries are assessed on an Agilent High Sensitivity DNA chip, and equimolar amounts of libraries pooled and resolved on 6% native PAGE and visualized by gel staining. Libraries are excised, eluted from the gel in TE buffer, ethanol precipitated, and resuspended in water or buffer of choice (TE, 20 mM HEPES pH 7.5, etc). Libraries are now ready for sequencing on the Illumina HiSeq 2000 platform.

Example 2

Detection of RNase L Cleavage Products in Activated Cells

Figure 1:
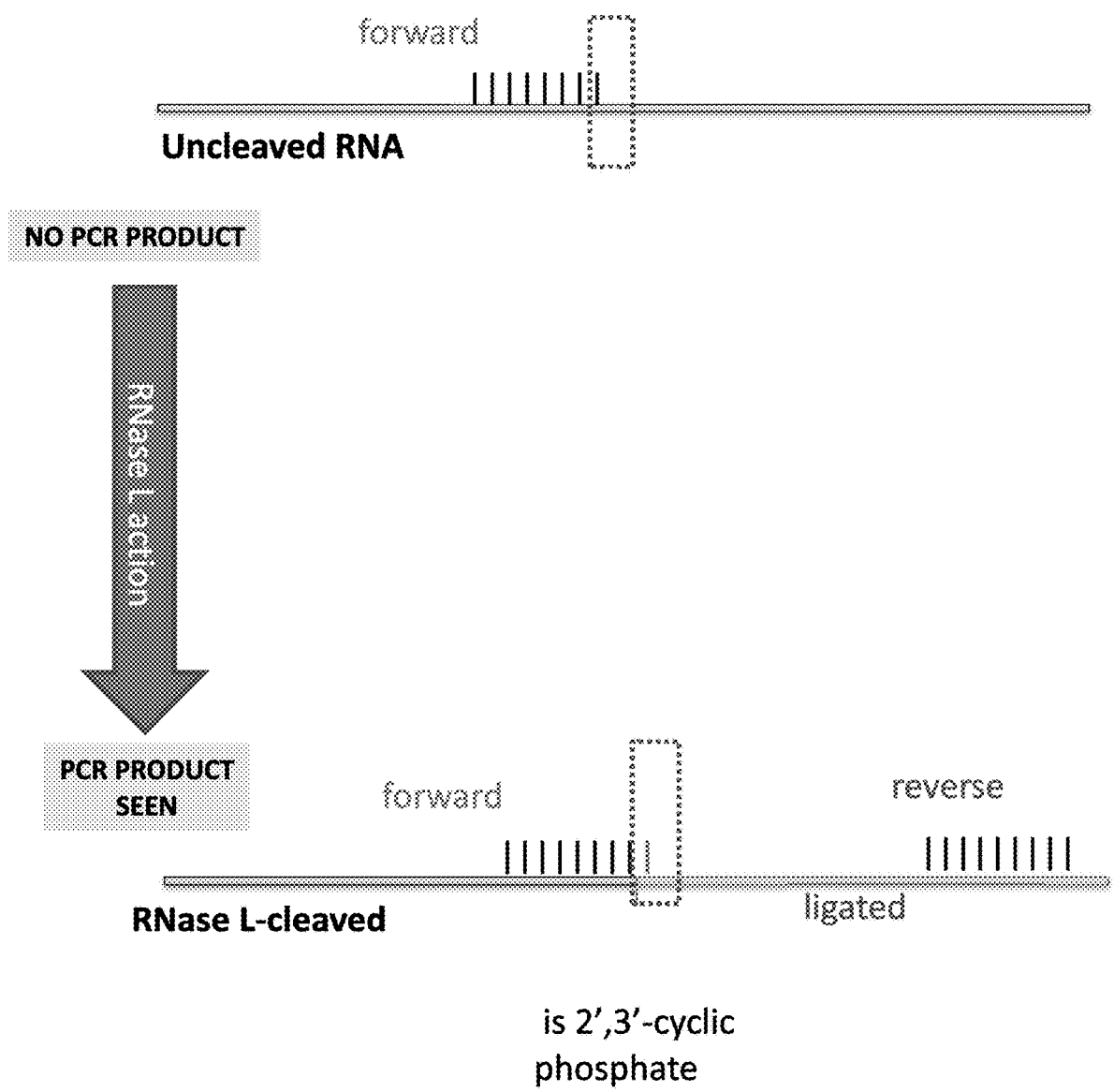
FIG. 1 is a schematic of a method of detecting RNase L cleavage products. The forward primer may have one or more bases designed to be complementary to the ligated adapter, but not to the intact sample RNA (shown as xx) to minimize amplification of forward primer hybridized to uncleaved RNA. The figure illustrates that that PCR product is observed once the RNase L has cleaved the RNA of interest.
Figure 2:
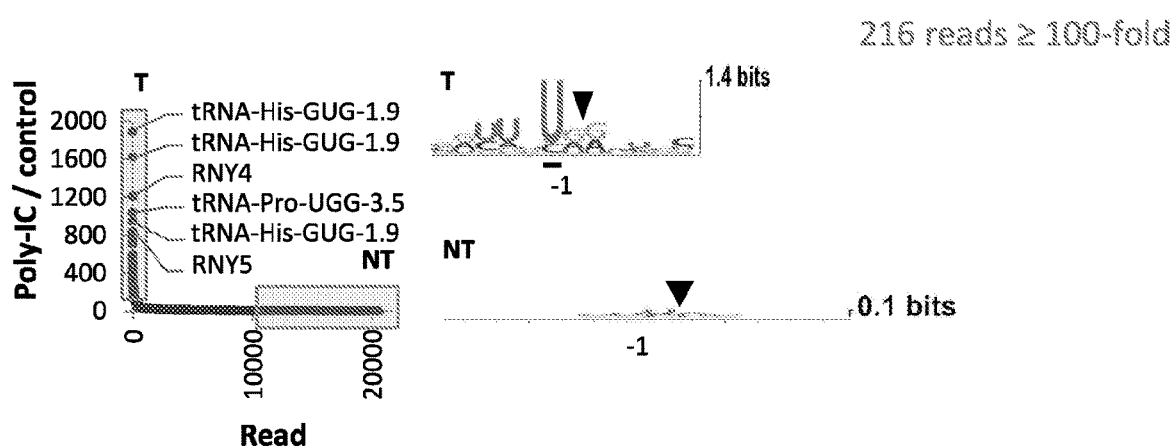
FIG. 2 highlights the most observed RNase L cleavage products in HeLa cells activated with poly I:C, and indicates that cleavage occurs most often after bases that follow a U nucleotide.
Figure 3:
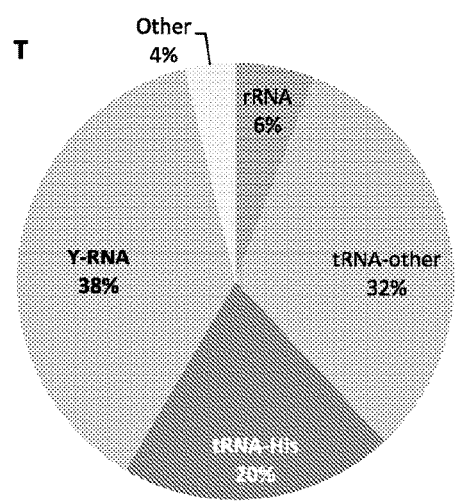
FIG. 3 is a graph that categorizes the major types of RNA cleaved by RNase L in activated HeLa cells. T=target RNAs of RNase L.

In order to determine if the present methods were useful to detect RNase L cleavage products in activated cells, HeLa cells were activated with polyinosinic-polycytidylic acid (polyI:C), which is a synthetic analog of double-stranded RNA (dsRNA) and stimulates cells in a manner similar to a viral infection. Small RNA was isolated and sequenced using the methods described in Example 1. FIG. 2 shows the most observed RNase L cleavage products in cells activated with polyI:C, and indicates that cleavage occurs most often after a U nucleotide. Analysis of the types of RNA cleaved by RNase L after cell activation shows that approximately 20% of the target RNA (T) products are tRNA-His related, approximately 32% is other tRNAs, approximately 38% is Y-RNA, approximately 6% is rRNA and 4% other types of products (FIG. 3).

FIGS. 4A-4E illustrate the most common cleavage sites for some of the RNase L cleavage products, e.g., for tRNA-His GUG-1-9 (also referred to as tRNA-His GUG-1.9) the most common cleavage residue is at nucleotide 36; for RNY1 nucleotides 23, 25, 26, 27, 28, 29 and 32, with the greatest cleavage at nucleotides 23 and 32; for RNY3 the most common cleavage residue is at nucleotide 32; for RNY4 at nucleotides 26 and 27; for RNY5 cleavage the most common cleavage residues are at nucleotides 26, 29, and 30. It is clear from the figures that other cleavage sites do occur within the RNA products and chimeric polynucleotides comprising these cleavage products is also contemplated.

Figure 4A:
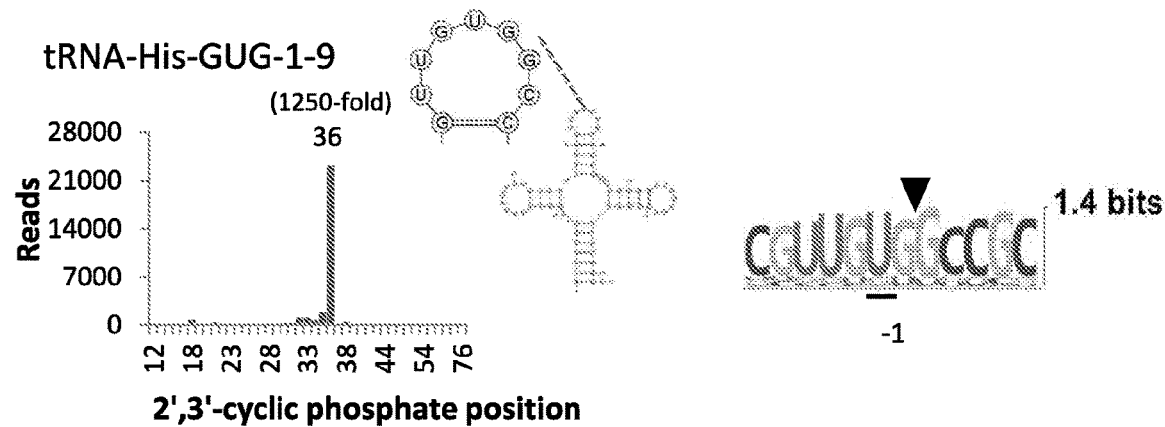
FIGS. 4A-4F illustrate the cleavage of different markers in activated HeLa cells.
Figure 4B:
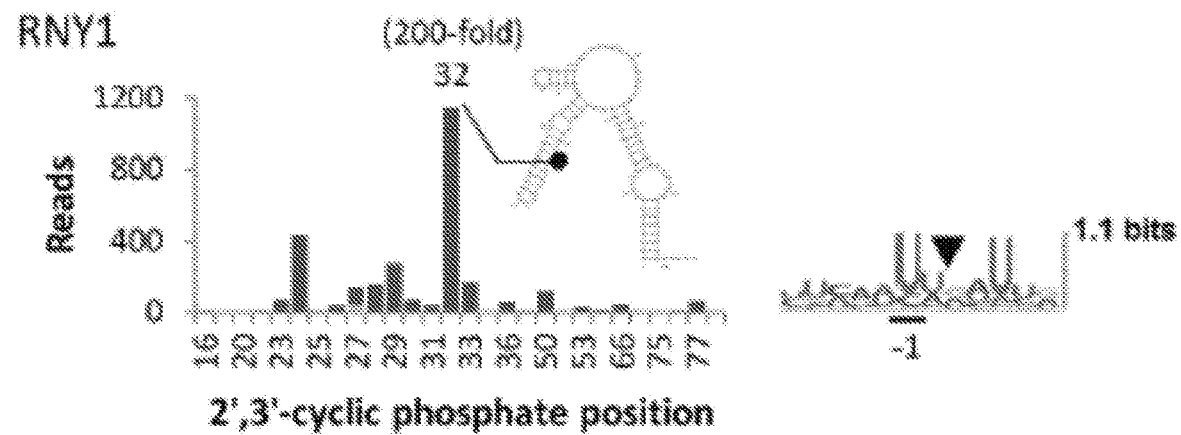
Figure 4C:
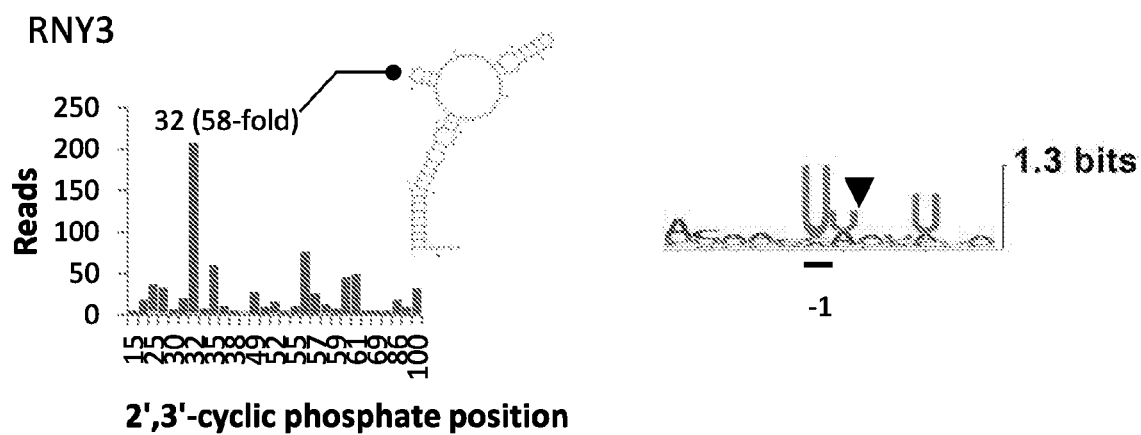
Figure 4D:
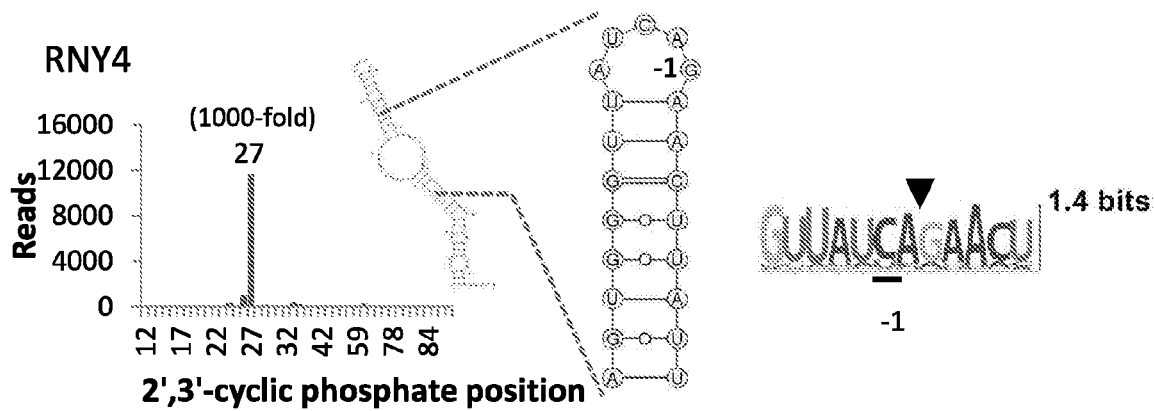
Figure 4E:
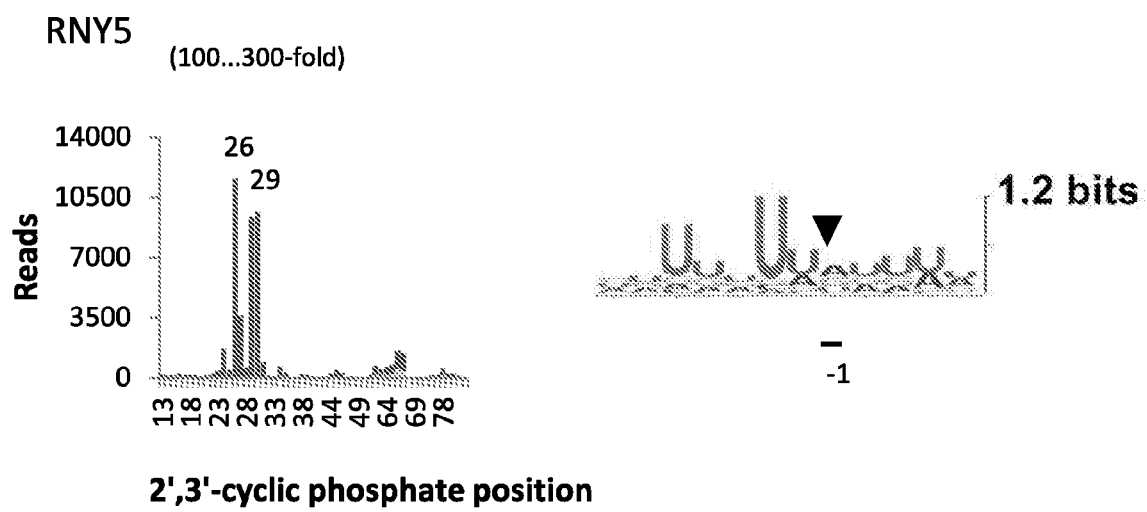
Figure 4F:
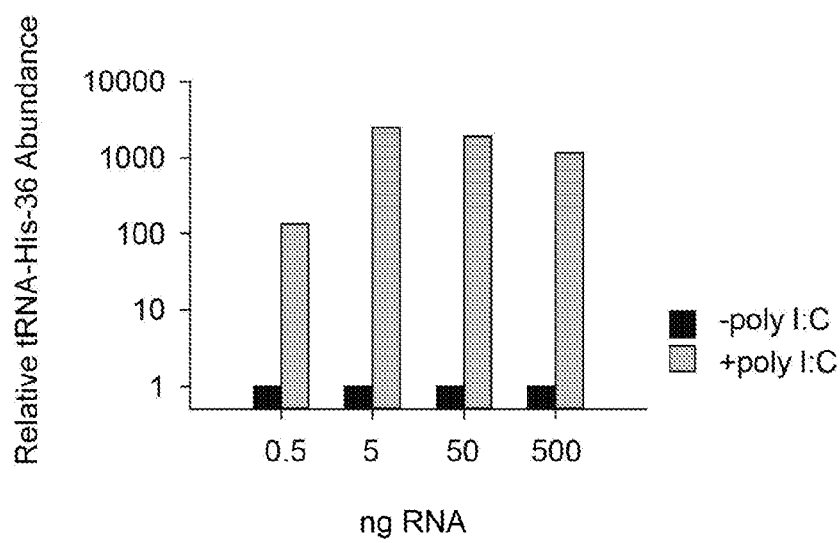

For the qPCR, total purified RNA from non-stimulated and poly I:C stimulated HeLa cells was serially diluted, ligated to the adapter with RtcB, reverse transcribed, and detected by qPCR using the His-GUG-36-2 primer and qPCR reverse primer. Results are shown in FIG. 4F. The results show that stimulation with polyI:C significantly increased the number of tRNA His-GUG-36-2 cleavage products compared to non-stimulated cells.

The cell samples were also analyzed for the presence of rRNA cleavage products. Purified total RNA from poly I:C treated or untreated HeLa cells were ligated, reverse transcribed, and amplified by qPCR. The results show that RNase L efficiently cleaves 28S rRNA, for example, at position 4032 of 28S rRNA (FIG. 9).

The RNA sequencing experiments were also carried out in HeLa cells that overexpress RNase L (RNLoe) and in T47D cells derived from human breast cancer and that have been permeablized and stimulated for 1 minute or 3 minutes with 1 μM 2-5A, which specifically activates RNase L but not other pathways. Results of the primary types of cleavage products detected, e.g., tRNA-His, tRNA-Pro, RNY1, RNY3, RNY4 and RNY5, were similar. However, different stimulus did produce some differences in RNase L cleavage nucleotides. FIGS. 5A-5E show the cleavage nucleotide profile of RNLoe cells. Analysis of the overall RNase L cleavage products from these cells indicated that for RNLoe cells, approximately 48% of the products are tRNA-His related, approximately 8% are other tRNAs, approximately 23% are Y-RNA, approximately 8% are rRNA and 11% other types of products.

FIGS. 6A-6E show the cleavage nucleotide profile of the T47D cells stimulated with 1 μM 2-5A for 1 minute. Profiles of the cells stimulated with 1 μM 2-5A for 3 minutes are similar, generally showing enhanced induction of RNA cleavage of the same products. Interestingly, 3 minute stimulation with 2-5A also produces cleavage at nucleotide 77 in RNY1. Analysis of the overall cleavage products in T47D cells stimulated 1 minute or 3 minutes with 1 μM 2-5A indicated that approximately 46-51% of the products are tRNA-His related, approximately 42-44% are other tRNAs, approximately 4-7% are Y-RNA, less than 1% are rRNA and approximately 3% are other types of products.

It is contemplated that a RNA sample is analyzed from a subject or patient using methods as outlined herein. For example, a sample can be obtained from blood, plasma, urine saliva, cerebrospinal fluid, or a cell or tissue sample and analyzed for the presence of an overall increased number of RNase L cleavage products and/or analyzed for certain RNase L cleavage product biomarkers, including, but not limited to, His-tRNA-GUG-1-9 (36); His-tRNA-GUG-1-9 variant sequence (37), Pro-tRNA-UGG-3-5 (34); Pro-tRNA-UGG-2-1 (34); Pro-tRNA-UGG-1-1 (34); His-tRNA-GUG-2-1 (36); Pro-tRNA-UGG-1-1 (34); His-tRNA-GUG-2-1 (36); His-tRNA-GUG-2-1 (37); Lys-tRNA-UUU-10-1 (36); Lys-tRNA-UUU-3-5 (36); Glu-tRNA-CUC-2-1 (36); Glu-tRNA-UUC-4-2 (36); Leu-tRNA-UAA-1-1 (50 or 51); Gln-UUG-1-1 (36); Thr-tRNA-UGU-2-1 (34); Val-tRNA- UAC-1-2 Gln-tRNA-UUG-1-1 (36); Gln-tRNA-CUG-4-2 (36); Gln-tRNA-CUG-1-5 (36); RNY4 (27); RNY5 (26 or 29 or 30 or 31); RNY1 (32); RNY3 (32); vtRNA1-2 (36); SNORA45A also known as SNORA3A (78); 28S rRNA (4032), 18S rRNA or RNU6-1. An increase in overall RNase L cleavage products and/or one or more of the above markers may be indicative of an immunogenic reaction in the subject.

The data herein show that cleavage products of RNase L are increased in cells in response to an immune stimulus and that these cleavage products can be specifically detected by the qPCR method described herein. These results suggest that RNase L cleavage products are useful biomarkers for detecting on ongoing immune response in a subject and that screening of a sample from a subject to determine if the subject is suffering from an ongoing immune response, e.g., as a result of infection, cancer, an autoimmune disease, asthma, or a neurodegenerative disease, and can be helpful for diagnosis of an immune response in the subject, as well as helpful in determining efficacy of any anti-inflammatory therapy the subject is receiving.

Numerous modifications and variations in the disclosure as set forth in the above illustrative examples are expected to occur to those skilled in the art. Consequently only such limitations as appear in the appended claims should be placed on the disclosure.

What is claimed:

1. A method for detecting an RNase L cleavage product comprising,
   a) isolating total RNA or small RNAs from a sample;
   b) ligating a ligation adapter polynucleotide to the RNA from the sample cleaved by RNase L, wherein the ligation adapter polynucleotide specifically ligates to RNA that has been cleaved by RNaseL, wherein the ligation adapter polynucleotide has at its 5' end at least 1 nucleotide that is identical to a 3' end of a first primer;
   c) generating cDNA by reverse-transcription of the RNA-ligation adapter polynucleotide ligation product using a reverse transcription primer that is complementary to at least a portion of the ligated ligation adapter polynucleotide;
   d) contacting the cDNA with the first primer, having at its 3' end at least 1 nucleotide identical to the ligation adapter polynucleotide 5' end and further comprising nucleotides identical to at least a portion of the sequence of RNase L-cleaved RNA and having one or more bases identical to the ligation adapter polynucleotide but not to uncleaved isolated RNA, and a second primer that is identical to at least a portion of the reverse transcription primer;
   e) amplifying the cDNA encoding the RNA-ligation adapter polynucleotide product; and
   f) detecting the amplified product of (e) to detect a RNase L cleaved RNA product ("RNase L cleavage product").

2. The method of claim 1 optionally comprising a step of isolating the amplified product prior to the detecting step.

3. The method of claim 1 wherein step (b) can be carried out prior to step (a).

4. The method of claim 1, wherein the detecting is performed by a method selected from the group consisting of PCR, qPCR, sequencing and DNA gel electrophoresis.

5. The method of claim 1 wherein the small RNAs are less than 200 nucleotides.

6. The method of claim 1 where the first primer
   (i) has no bases complementary to the ligation adapter polynucleotide;
   (ii) has from 1 to 10 bases complementary to the ligation adapter polynucleotide, but not to the RNA cleaved by RNase L; or
   (iii) comprises 1, 2 or 3 nucleotides that are complementary to the ligation adapter polynucleotide sequence.

7. The method of claim 1 wherein the first and second primers consist of between 17 and 24 nucleotides each.

8. The method of claim 1 wherein the ligation adapter polynucleotide is ligated to the isolated RNA with RtcB RNA ligase.

9. The method of claim 1 wherein the ligation adapter polynucleotide has a 2', 3' cyclic phosphate or 3'-phosphate and is ligated to the 5'-OH-end of RNA cleaved by RNase L.

10. The method of claim 1 wherein the RNA cleaved by RNase L is labeled with a detectable label.

11. The method of claim 1 wherein the ligation adapter polynucleotide is RNA or an RNA/DNA mixed polynucleotide.

12. The method of claim 1 wherein the ligation adapter polynucleotide has the polynucleotide sequence 5'-GAUC-GUCGGACTGTAGAACTCTGAAC-3' (SEQ ID NO: 1), wherein the first 6 nucleotides are RNA and the remainder of the nucleotides are DNA.

13. The method of claim 1 wherein the RNase L cleavage product results from cleavage of RNA by RNase L between nucleotides that follow a U or a C RNA base, optionally wherein the sequence is UN^N or CN^N.

14. The method of claim 1 wherein the sample is isolated from a subject.

15. The method of claim 14 wherein the subject is suspected of suffering from or is suffering from inflammation or an ongoing immune response.

16. The method of claim 1 wherein the RNase L cleavage product is
(i) a tRNA, rRNA, Y-RNA, snoRNA or vtRNA;
(ii) tRNA-His, tRNA-Gln, tRNA-Glu, tRNA-Lys or tRNA-Pro;
(iii) RNY1, RNY3, RNY4 or RNY5;
(iv) VTRNA1 or VTRNA2; or
(v) RNU1, SNORA1, SNORD16, 28S RNA or 18S rRNA.

17. A method for determining efficacy of an anti-inflammatory treatment in a subject suffering from inflammation comprising detecting RNase L cleavage products in a subject according to the method of claim 1 before and after administration of an anti-inflammatory agent, wherein a decrease in RNase L cleavage products after administration indicates the anti-inflammatory agent is reducing inflammation in the subject.

* * * * *

```
                          SEQUENCE LISTING

<160> NUMBER OF SEQ ID NOS: 355

<210> SEQ ID NO 1
    <211> LENGTH: 26
    <212> TYPE: DNA
    <213> ORGANISM: Artificial Sequence
    <220> FEATURE:
    <223> OTHER INFORMATION: Synthetic polynucleotide

<400> SEQUENCE: 1
gaucgucgga ctgtagaact ctgaac                                       26

<210> SEQ ID NO 2
    <211> LENGTH: 75
    <212> TYPE: DNA
    <213> ORGANISM: Artificial Sequence
    <220> FEATURE:
    <223> OTHER INFORMATION: Synthetic polynucleotide

<400> SEQUENCE: 2
gccgugaucg uauagugguu aguacucugc guuguggccg cagcaaccuc gguucgaauc    60
cgagucacgg cacca                                                   75

<210> SEQ ID NO 3
    <211> LENGTH: 76
    <212> TYPE: DNA
    <213> ORGANISM: Artificial Sequence
    <220> FEATURE:
    <223> OTHER INFORMATION: Synthetic polynucleotide

<400> SEQUENCE: 3
ggccgugauc guauagugu uaguacucug cguuguggcc gcagcaaccu cgguucgaau    60
ccgagucacg gcacca                                                  76

<210> SEQ ID NO 4
    <211> LENGTH: 75
    <212> TYPE: DNA
    <213> ORGANISM: Artificial Sequence
    <220> FEATURE:
    <223> OTHER INFORMATION: Synthetic polynucleotide

<400> SEQUENCE: 4
ggcucguugg ucuaggggua ugauucucgc uuugggugcg agagguccccg gguucaaauc    60 ccggacgagc cccca                                                   75

<210> SEQ ID NO 5
    <211> LENGTH: 75
    <212> TYPE: DNA
    <213> ORGANISM: Artificial Sequence
    <220> FEATURE:
```

<223> OTHER INFORMATION: Synthetic polynucleotide

<400> SEQUENCE: 5

```
ggcucguugg ucuaggggua ugauucucgg uuuggguccg agagucccg gguucaaauc    60 ccggacgagc cccca                                                    75
```

<210> SEQ ID NO 6
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 6

```
ggcucguugg ucuaguggua ugauucucgc uuugggugcg agagucccg gguucaaauc    60 ccggacgagc cccca                                                    75
```

<210> SEQ ID NO 7
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 7

```
gccaugaucg uauagugguu aguacucugc gcuguggccg cagcaaccuc gguucgaauc    60
cgagucacgg cacca                                                    75
```

<210> SEQ ID NO 8
<211> LENGTH: 76
<212> TYPE: DNA
<213> ORGANISM: Artificial Sequence
<220> FEATURE:
<223> OTHER INFORMATION: Synthetic polynucleotide

<400> SEQUENCE: 8

```
ggccaugauc guauagguggu uaguacucug cgcuguggcc gcagcaaccu cgguucgaau   60
ccgagucacg gcacca                                                   76
```

<210> SEQ ID NO 9
<211> LENGTH: 76
<212> TYPE: DNA
<213> ORGANISM: Artificial Sequence
<220> FEATURE:
<223> OTHER INFORMATION: Synthetic polynucleotide

<400> SEQUENCE: 9

```
gccaggauag uucagguggu agagcaucag acuuuuaacc ugagggguuca ggguucaagu   60 cucguuugg gcgcca                                                    76
```

<210> SEQ ID NO 10
<211> LENGTH: 76
<212> TYPE: DNA
<213> ORGANISM: Artificial Sequence
<220> FEATURE:
<223> OTHER INFORMATION: Synthetic polynucleotide

<400> SEQUENCE: 10

```
gcccggauag cucagucggu agagcaucag acuuuuaauc ugaggguccca ggguucaagu   60 cccguucgg gcgcca                                                    76
```

```
<210> SEQ ID NO 11
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 11
ucccuggugg ucuagugguu aggauucggc gcucucaccg ccgcggcccg gguucgauuc    60
ccggucagga aacca                                                    75

<210> SEQ ID NO 12
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 12
ucccuggugg ucuaguggcu aggauucggc gcuuucaccg ccgcggcccg gguucgauuc    60
ccggucaggg aacca                                                    75

<210> SEQ ID NO 13
<211> LENGTH: 86
<212> TYPE: DNA
<213> ORGANISM: Artificial Sequence
<220> FEATURE:
<223> OTHER INFORMATION: Synthetic polynucleotide

<400> SEQUENCE: 13
accaggaugg ccgagugguu aaggcguugg acuuaagauc caauggacau auguccgcgu    60
ggguucgaac cccacuccug guacca                                        86

<210> SEQ ID NO 14
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 14
ggucccaugg uguaaugguu agcacucugg acuuugaauc cagcgauccg aguucaaauc    60 ucgguggggac cucca                                                   75

<210> SEQ ID NO 15
<211> LENGTH: 76
<212> TYPE: DNA
<213> ORGANISM: Artificial Sequence
<220> FEATURE:
<223> OTHER INFORMATION: Synthetic polynucleotide

<400> SEQUENCE: 15
ggcuccauag cucagugguu agagcacugg ucuuguaaac caggggucgc gaguucgauc    60
cucgcugggg ccucca                                                   76

<210> SEQ ID NO 16
<211> LENGTH: 73
<212> TYPE: DNA
<213> ORGANISM: Artificial Sequence
<220> FEATURE:
<223> OTHER INFORMATION: Synthetic polynucleotide

<400> SEQUENCE: 16
```

-continued

```
gguuccauag uguagugguu aucacgucug cuuuacacgc agaagguccu ggguucgagc    60
cccaguggaa cca                                                      73
```

<210> SEQ ID NO 17
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 17

```
ggucccaugg uguaaugguu agcacucugg acuuugaauc cagcgauccg aguucaaauc    60
ucggugggac cucca                                                    75
```

<210> SEQ ID NO 18
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 18

```
gguccaugg uguaauggua agcacucugg acucugaauc cagcgauccg aguucgaguc     60
ucgguggaac cucca                                                    75
```

<210> SEQ ID NO 19
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 19

```
gguccaugg uguaaugguu agcacucugg acucugaauc cagcgauccg aguucaaauc     60
ucgguggaac cucca                                                    75
```

<210> SEQ ID NO 20
<211> LENGTH: 96
<212> TYPE: DNA
<213> ORGANISM: Artificial Sequence
<220> FEATURE:
<223> OTHER INFORMATION: Synthetic polynucleotide

<400> SEQUENCE: 20

```
ggcugguccg augguagugg guuaucagaa cuuauuaaca uuagugucac uaaaguuggu    60 auacaaccccc ccacugcuaa auuugacugg cuuuuu                            96
```

<210> SEQ ID NO 21
<211> LENGTH: 84
<212> TYPE: DNA
<213> ORGANISM: Artificial Sequence
<220> FEATURE:
<223> OTHER INFORMATION: Synthetic polynucleotide

<400> SEQUENCE: 21

```
aguugguccg aguguugugg guuauuguua aguugauuua acauugucuc ccccacaac    60 cgcgcuugac uagcuugcug uuuu                                         84
```

<210> SEQ ID NO 22
<211> LENGTH: 113
<212> TYPE: DNA
<213> ORGANISM: Artificial Sequence

```
<220> FEATURE:
<223> OTHER INFORMATION: Synthetic polynucleotide

<400> SEQUENCE: 22
ggcugguccg aagguaguga guuaucucaa uugauuguuc acagucaguu acagaucgaa    60
cuccuuguuc uacucuuucc ccccuucuca cuacugcacu ugacuagucu uuu           113

<210> SEQ ID NO 23
<211> LENGTH: 102
<212> TYPE: DNA
<213> ORGANISM: Artificial Sequence
<220> FEATURE:
<223> OTHER INFORMATION: Synthetic polynucleotide

<400> SEQUENCE: 23
ggcugguccg agugcagugg uguuuacaac uaauugauca caaccaguua cagauuucuu    60
uguuccuucu ccacucccac ugcuucacuu gacuagccuu uu                      102

<210> SEQ ID NO 24
<211> LENGTH: 89
<212> TYPE: DNA
<213> ORGANISM: Artificial Sequence
<220> FEATURE:
<223> OTHER INFORMATION: Synthetic polynucleotide

<400> SEQUENCE: 24
gggcuggcuu uagcucagcg guuacuucga guacauugua accaccucuc uggguggcuuc   60 gagacccgcg ggugcuuucc agcucuuuu                                     89

<210> SEQ ID NO 25
<211> LENGTH: 130
<212> TYPE: DNA
<213> ORGANISM: Artificial Sequence
<220> FEATURE:
<223> OTHER INFORMATION: Synthetic polynucleotide

<400> SEQUENCE: 25
atcgaggcta gagtcacgct tgggtatcgg ctattgcctg agtgtgctag agtcctcgaa    60
gagtaactgc tgaccttatt cactggctgt gggccttatg gcacagtcag tcaccaggtt   120
agagacatgc                                                          130

<210> SEQ ID NO 26
<211> LENGTH: 106
<212> TYPE: DNA
<213> ORGANISM: Artificial Sequence
<220> FEATURE:
<223> OTHER INFORMATION: Synthetic polynucleotide

<400> SEQUENCE: 26
gtgctcgctt cggcagcaca tatactaaaa ttggaacgat acagagaaga ttagcatggc    60
ccctgcgcaa ggatgacacg caaattcgtg aagcgttcca tatttt                  106

<210> SEQ ID NO 27
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 27
gatggtagtg ggttatcaga t                                              21
```

<210> SEQ ID NO 28
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 28
gtgttgtggg ttattgttag                                              20

<210> SEQ ID NO 29
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 29
gtgttgtggg ttattgttag a                                            21

<210> SEQ ID NO 30
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 30
gtgttgtggg ttattgttag atc                                          23

<210> SEQ ID NO 31
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 31
gttagtactc tgcgttgtgg at                                           22

<210> SEQ ID NO 32
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 32
gttagtactc tgcgttgtga                                              20

<210> SEQ ID NO 33
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 33
ggccgtgatc gtatagtggg at                                           22

<210> SEQ ID NO 34
<211> LENGTH: 21
<212> TYPE: DNA
<213> ORGANISM: Artificial Sequence
<220> FEATURE:
<223> OTHER INFORMATION: Synthetic polynucleotide

```
<400> SEQUENCE: 34
ggccgtgatc gtatagtggg a                                              21

<210> SEQ ID NO 35
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 35
ggggtccgcc ggccctgga                                                 19

<210> SEQ ID NO 36
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 36
gcttcggcag cacatatact a                                              21

<210> SEQ ID NO 37
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 37
cgaatttgcg tgtcatcctt g                                              21

<210> SEQ ID NO 38
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 38
cgtgaagcgt tccatatttt ga                                             22

<210> SEQ ID NO 39
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 39
tccctatcag tgatagagag ttcagagttc tacagtccg                           39

<210> SEQ ID NO 40
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 40
tccctatcag tgatagagag                                                20

<210> SEQ ID NO 41
```

```
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 41
gttcagagtt ctacagtccg acgatc                                              26

<210> SEQ ID NO 42
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 42
tggaattctc gggtgccaag g                                                   21

<210> SEQ ID NO 43
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 43
atcgtatagt ggttagtact ctgcgttgtg                                          30

<210> SEQ ID NO 44
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 44
atcgtatagt ggtgagtact ctgcgttgtg                                          30

<210> SEQ ID NO 45
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 45
tggctggtcc gatggtagtg ggttatca                                            28

<210> SEQ ID NO 46
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 46 gtctagggt atgattctcg ctttg                                                25

<210> SEQ ID NO 47
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 47
```
tggccgtgat cgtatagtgg ttagtactct gcgttgtg                                    38

<210> SEQ ID NO 48
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 48
tagttggtcc gagtgttgtg ggtta                                                  25

<210> SEQ ID NO 49
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 49
gctggtccga tggtagtggg ttatca                                                 26

<210> SEQ ID NO 50
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 50
gtatagtggt gagtatcccc gcctgtctt                                              29

<210> SEQ ID NO 51
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 51
tcgatggtag tgggttatca                                                        20

<210> SEQ ID NO 52
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 52
gtctaggggt atgattctcg gtttg                                                  25

<210> SEQ ID NO 53
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 53
ggctggtccg atggtagtgg gttatca                                                27

<210> SEQ ID NO 54
<211> LENGTH: 66
<212> TYPE: DNA

<213> ORGANISM: Artificial Sequence
<220> FEATURE:
<223> OTHER INFORMATION: Synthetic polynucleotide

<400> SEQUENCE: 54
tcgcgaaggc cgcggcggg tgttgacgcg atgtgatttc tgcccagtgc tctgaatgtc    60
aaagtg    66

<210> SEQ ID NO 55
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 55
tagagtgttc aaagcaggcc cgagccgcct ggataccgca gctaggaata atggaata    58

<210> SEQ ID NO 56
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 56
atcgtatagt ggttagtact ctgcgctgtg    30

<210> SEQ ID NO 57
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 57
agtactctgc gttgtg    16

<210> SEQ ID NO 58
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 58
ttggtctagg ggtatgattc tcgctttg    28

<210> SEQ ID NO 59
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 59
gggccgtgat cgtatagtgg ttagtactct gcgttgtg    38

<210> SEQ ID NO 60
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 60

```
ttggtctagg ggtatgattc tcggtttg                                           28

<210> SEQ ID NO 61
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 61
ttgatcgtat agtggttagt actctgcgtt gtg                                     33

<210> SEQ ID NO 62
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 62
aagcgtttac tttgaaaaaa ttagagtgtt caaagcaggc ccga                         44

<210> SEQ ID NO 63
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 63
ccgatggtag tgggttatca                                                    20

<210> SEQ ID NO 64
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 64
tggctggtcc gatggtagtg ggtta                                              25

<210> SEQ ID NO 65
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 65
tcgtatagtg gttagtactc tgcgttgtg                                          29

<210> SEQ ID NO 66
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 66
tcggggccac gcgcgcgtcc cccgaa                                             26

<210> SEQ ID NO 67
<211> LENGTH: 36
<212> TYPE: DNA
```

```
<213> ORGANISM: Artificial Sequence
<220> FEATURE:
<223> OTHER INFORMATION: Synthetic polynucleotide

<400> SEQUENCE: 67
gccgtgatcg tatagtggtt agtactctgc gttgtg                                    36

<210> SEQ ID NO 68
<211> LENGTH: 13
<212> TYPE: DNA
<213> ORGANISM: Artificial Sequence
<220> FEATURE:
<223> OTHER INFORMATION: Synthetic polynucleotide

<400> SEQUENCE: 68
actctgcgtt gtg                                                             13

<210> SEQ ID NO 69
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 69
aggctggtcc gatggtagtg ggttatca                                             28

<210> SEQ ID NO 70
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 70
atatagctgc taagtgctgt gttgtcgttc cccctgctta aaataaagtt gtttctta            58

<210> SEQ ID NO 71
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 71
gcgtttactt tgaaaaaatt agagtgttca aagcaggccc gagccgcctg gataccg             57

<210> SEQ ID NO 72
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 72
gggcactgtt gatcatggtg tccaaaaata gttaatgtgg ctaaattgag acaggtta           58

<210> SEQ ID NO 73
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 73
tgatggtagt gggttatca                                                       19
```

<210> SEQ ID NO 74
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 74
ttagtactct gcgttgtg                                            18

<210> SEQ ID NO 75
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 75
agtgttgtgg gttattgtta                                          20

<210> SEQ ID NO 76
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 76
tgatcgtata gtggttagta ctctgcgttg tg                             32

<210> SEQ ID NO 77
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 77
gggtaaacgg cgggagtaac tatgactctc ttaaggtagc caaatgcctc gtcatcta    58

<210> SEQ ID NO 78
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 78
agttggtccg agtgttgtgg gttatt                                   26

<210> SEQ ID NO 79
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 79
gtctagtggt atgattctcg ctttg                                    25

<210> SEQ ID NO 80
<211> LENGTH: 16
<212> TYPE: DNA
<213> ORGANISM: Artificial Sequence
<220> FEATURE:

<223> OTHER INFORMATION: Synthetic polynucleotide

<400> SEQUENCE: 80
agtgttgtgg gttatt                                              16

<210> SEQ ID NO 81
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 81
atactctggt ttctcttcaa atcgta                                    26

<210> SEQ ID NO 82
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 82
agttggtccg agtgttgtgg gttattgtta                                30

<210> SEQ ID NO 83
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 83
atagtggtta gtactctgcg ttgtg                                     25

<210> SEQ ID NO 84
<211> LENGTH: 62
<212> TYPE: DNA
<213> ORGANISM: Artificial Sequence
<220> FEATURE:
<223> OTHER INFORMATION: Synthetic polynucleotide

<400> SEQUENCE: 84
ttgcaatgat gtcgtaattt gcgtcttact ctgttctcag cgacagttgc ctgctgtcag    60
ta                                                                   62

<210> SEQ ID NO 85
<211> LENGTH: 70
<212> TYPE: DNA
<213> ORGANISM: Artificial Sequence
<220> FEATURE:
<223> OTHER INFORMATION: Synthetic polynucleotide

<400> SEQUENCE: 85
agcaggacgg tggccatgga agtcggaatc cgctaaggag tgtgtaacaa ctcacctgcc    60
gaatcaacta                                                           70

<210> SEQ ID NO 86
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 86
agagcatcag actttt 16

<210> SEQ ID NO 87
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 87
ggccgtgatc gtatagtggt tagtactctg cgttgtg 37

<210> SEQ ID NO 88
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 88
tatagtggtt agtactctgc gttgtg 26

<210> SEQ ID NO 89
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 89
aaagcgcctg tttg 14

<210> SEQ ID NO 90
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 90
aagttggtcc gagtgttgtg ggttatt 27

<210> SEQ ID NO 91
<211> LENGTH: 62
<212> TYPE: DNA
<213> ORGANISM: Artificial Sequence
<220> FEATURE:
<223> OTHER INFORMATION: Synthetic polynucleotide

<400> SEQUENCE: 91
gcgggccgcc ggtgaaatac cactactctg atcgttttt cactgacccg gtgaggcggg 60
gg 62

<210> SEQ ID NO 92
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 92
tagtactctg cgttgtg 17

<210> SEQ ID NO 93

<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 93
gcccggctag ctcagtcggt agagcatggg actctt         36

<210> SEQ ID NO 94
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 94
gtgtaatggt tagcactctg gactctgca              29

<210> SEQ ID NO 95
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 95
tggtccgatg gtagtgggtt atca                 24

<210> SEQ ID NO 96
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 96
tctgtggcag atgatcaaaa ctgtctgaca caatttgagc ttgctatagc aagaaagtct    60
aaccta                                    66

<210> SEQ ID NO 97
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 97
cgatggtagt gggttatca                     19

<210> SEQ ID NO 98
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 98
aagttggtcc gagtgttgtg ggttattgtt a              31

<210> SEQ ID NO 99
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 99
gttggtccga gtgttgtggg ttatt					25

<210> SEQ ID NO 100
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 100
agtactctgc gctgtg					16

<210> SEQ ID NO 101
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 101
gagttggtcc gagtgttgtg ggttattgtt					30

<210> SEQ ID NO 102
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 102
agagcactgg tctt					14

<210> SEQ ID NO 103
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 103
gggctggtcc gatggtagtg ggttatca					28

<210> SEQ ID NO 104
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 104
gtgtaatggt tagcactctg gactctgta					29

<210> SEQ ID NO 105
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 105
ggccgtgatc gtatagtggt gagtactctg cgttgtg					37

<210> SEQ ID NO 106

<210> SEQ ID NO 106
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 106
gtaatggtta gcactctgga ctctg                                   25

<210> SEQ ID NO 107
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 107
attaacatta gtgtcactaa agttggta                                28

<210> SEQ ID NO 108
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 108
gttggtccga gtgttgtggg ttattgtt                                28

<210> SEQ ID NO 109
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 109
tcgcgaaggc ccgcggcggg tgttgacgcg atgtg                        35

<210> SEQ ID NO 110
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 110
agagcactgg tcttg                                              15

<210> SEQ ID NO 111
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 111
ataactcagt cggtagagca tcagactttt                              30

<210> SEQ ID NO 112
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 112
gaagtcggaa tccgctaagg agtgtgtaac aactcacctg ccgaatcaac tagccctg    58

<210> SEQ ID NO 113
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 113
atcgtatagt ggttaggact ctgcgttgtg    30

<210> SEQ ID NO 114
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 114
gcgggccgcc ggtgaaatac cactactctg atc    33

<210> SEQ ID NO 115
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 115
ttgcactgca tggta    15

<210> SEQ ID NO 116
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 116
gagttggtcc gagtgttgtg ggttattgtt a    31

<210> SEQ ID NO 117
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 117
tagttggtcc gagggttgtg ggttattgtt    30

<210> SEQ ID NO 118
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 118
ggacggtggc catggaagtc ggaatccgct aaggagtgtg taacaactca cctgccgaat    60
caacta    66

<210> SEQ ID NO 119

```
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 119
atcacgtctg cttta                                                          15

<210> SEQ ID NO 120
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 120
aagaaattca atgaagcgcg ggtaaacggc gggagtaact atgactctct ta                  52

<210> SEQ ID NO 121
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 121
atcgtatagt ggttagtact ctgcgttgtg tt                                       32

<210> SEQ ID NO 122
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 122
ctggtccgat ggtagtgggt tatca                                               25

<210> SEQ ID NO 123
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 123
atatactctg gtttctcttc aaatcgta                                            28

<210> SEQ ID NO 124
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 124
gcgttggtgg tatagtggta                                                     20

<210> SEQ ID NO 125
<211> LENGTH: 61
<212> TYPE: DNA
<213> ORGANISM: Artificial Sequence
<220> FEATURE:
<223> OTHER INFORMATION: Synthetic polynucleotide

<400> SEQUENCE: 125
```
cgggccgccg gtgaaatacc actactctga tcgttttttc actgacccgg tgaggcgggg    60
g                                                                    61

<210> SEQ ID NO 126
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 126
gttggtccga gtgttgtggg ttattgtta                                      29

<210> SEQ ID NO 127
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 127
atggttagca ctctggactc tg                                             22

<210> SEQ ID NO 128
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 128
taatggttag cactctggac tctg                                           24

<210> SEQ ID NO 129
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 129 tctagggta tgattctcgc tttg                                            24

<210> SEQ ID NO 130
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 130
atacttacct ggcaggggag ataccatgat ta                                  32

<210> SEQ ID NO 131
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 131
gtatagtggt tagtactctg cgttgtg                                        27

<210> SEQ ID NO 132

<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 132
tagttggatc ttgggagcgg gcgggcggtc cgccgcgagg cgagccaccg cccgtccccg    60
cccctt                                                              66

<210> SEQ ID NO 133
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 133
agcgtttact ttgaaaaaat tagagtgttc aaagcaggcc cga                     43

<210> SEQ ID NO 134
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 134
aagcgtttac tttgaaaaaa ttagagtgtt caaagcaggc ccg                     43

<210> SEQ ID NO 135
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 135
tagttggtcc gagtgttgtg ggttatt                                       27

<210> SEQ ID NO 136
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 136
ggtccgatgg tagtgggtta tca                                           23

<210> SEQ ID NO 137
<211> LENGTH: 70
<212> TYPE: DNA
<213> ORGANISM: Artificial Sequence
<220> FEATURE:
<223> OTHER INFORMATION: Synthetic polynucleotide

<400> SEQUENCE: 137
ataagtggga ggccccccggc gccccccgg tgtccccgcg aggggcccgg ggcggggtcc    60
gccggccctg                                                          70

<210> SEQ ID NO 138
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 138
aagcgtttac tttgaaaaaa ttagagtgtt caaagcaggc ccgagccgcc tggatacc        58

<210> SEQ ID NO 139
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 139
cgtatagtgg ttagtactct gcgttgtg                                         28

<210> SEQ ID NO 140
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 140
gtatagtggt gagtatcccc gcctgtt                                          27

<210> SEQ ID NO 141
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 141
tcgggccgcc ggtgaaatac cactactctg atc                                   33

<210> SEQ ID NO 142
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 142
tagttggtcc gagtgttgtg ggttattgtt a                                     31

<210> SEQ ID NO 143
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 143
tagttggtcc gagtgttgtg ggttattg                                         28

<210> SEQ ID NO 144
<211> LENGTH: 62
<212> TYPE: DNA
<213> ORGANISM: Artificial Sequence
<220> FEATURE:
<223> OTHER INFORMATION: Synthetic polynucleotide

<400> SEQUENCE: 144
agcaggacgg tggccatgga agtcggaatc cgctaaggag tgtgtaacaa ctcacctgcc       60

```
ga                                                                 62

<210> SEQ ID NO 145
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 145
ttggacttaa gatccaatgg acata                                        25

<210> SEQ ID NO 146
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 146
agcactctgg actttg                                                  16

<210> SEQ ID NO 147
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 147
gtgtaatggt tagcactctg gactctgga                                    29

<210> SEQ ID NO 148
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 148
tcgggccgcc ggtgaaatac cactactctg atcgtttttt cactgacccg gt          52

<210> SEQ ID NO 149
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 149
gaagcgttta ctttgaaaaa attagagtgt tcaaagcagg cccg                   44

<210> SEQ ID NO 150
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 150
tagttggtcc gagtgttgtg ggttattgtt                                   30

<210> SEQ ID NO 151
<211> LENGTH: 31
<212> TYPE: DNA
<213> ORGANISM: Artificial Sequence
```

```
<220> FEATURE:
<223> OTHER INFORMATION: Synthetic polynucleotide

<400> SEQUENCE: 151
aatcgtatag tggttagtac tctgcgttgt g                              31

<210> SEQ ID NO 152
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 152
atccaatgga ttcata                                               16

<210> SEQ ID NO 153
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 153
tttggtctag gggtatgatt ctcggtttg                                 29

<210> SEQ ID NO 154
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 154
gttagcactc tggactctg                                            19

<210> SEQ ID NO 155
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 155
aagcgtttac tttgaaaaaa ttagagtgtt caaagcaggc ccgagccgcc tggataccg  59

<210> SEQ ID NO 156
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 156
agttggtccg agggttgtgg gttatt                                    26

<210> SEQ ID NO 157
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 157
gtgtaatggt tagcactctg gactctgtg                                 29
```

<210> SEQ ID NO 158
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 158
tttggtctag gggtatgatt ctcgctttg                                29

<210> SEQ ID NO 159
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 159
agatctctgg tttctcttca ta                                       22

<210> SEQ ID NO 160
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 160
cggctggtcc gatggtagtg ggttatca                                 28

<210> SEQ ID NO 161
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 161
tagttggtcc gagtgttgtg ggttattgtt aagttg                        36

<210> SEQ ID NO 162
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 162
tagttggtcc gagtgttgtg ggttattgtt aagttgattt aacatt             46

<210> SEQ ID NO 163
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 163
ggctggtccg aaggtagtga gttatctcaa tt                            32

<210> SEQ ID NO 164
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 164
agcgcattcg gctgtt                                                    16

<210> SEQ ID NO 165
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 165
tcgaggccct gtaattggaa tgagtccact ttaaatcctt taacgaggat ccattggagg    60
gcaagt                                                               66

<210> SEQ ID NO 166
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 166
tcgcgaaggc ccgcggcggg tgttgacgcg atg                                 33

<210> SEQ ID NO 167
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 167
ttatagtggt tagtactctg cgttgtg                                        27

<210> SEQ ID NO 168
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 168
gtgtaatggt aagcactctg gactctg                                        27

<210> SEQ ID NO 169
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 169
cgtgcttggg tctgcggtga ccctatgcat tccttcagtg cttgctagaa cagttttgaa    60
acggtt                                                               66

<210> SEQ ID NO 170
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 170

```
ggtaacgcag gtgtccta                                                    18

<210> SEQ ID NO 171
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 171
attaaaacaa agcatcgcga aggcccgcgg cgggtgttga cgcgatgtga tt             52

<210> SEQ ID NO 172
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 172
gtgtaatggt tagcactctg gactctg                                          27

<210> SEQ ID NO 173
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 173
tggtccgagt gttgtgggtt att                                              23

<210> SEQ ID NO 174
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 174
gtgtaatggt tagcactctg gactttg                                          27

<210> SEQ ID NO 175
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 175
agttggtccg agtgttg                                                     17

<210> SEQ ID NO 176
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 176
tgtaatggtt agcactctgg actttg                                           26

<210> SEQ ID NO 177
<211> LENGTH: 30
<212> TYPE: DNA
<213> ORGANISM: Artificial Sequence
```

<220> FEATURE:
<223> OTHER INFORMATION: Synthetic polynucleotide

<400> SEQUENCE: 177
atagctcagt cggtagagca tcagactttt                                      30

<210> SEQ ID NO 178
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 178
cgggccgccg gtgaaatacc actactctga tc                                   32

<210> SEQ ID NO 179
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 179
agttggtccg agtgttgtgg gtta                                            24

<210> SEQ ID NO 180
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 180
tgggtatcgg ctattgcctg agtgtgctag agtcctcgaa gagtaactgc tgaccttta      58

<210> SEQ ID NO 181
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 181
tccctggtgg tctagtggct aggattcggc gctt                                 34

<210> SEQ ID NO 182
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 182
gtataaacta atacaccagt c                                               21

<210> SEQ ID NO 183
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 183
tagagcatca gactttt                                                    17

<210> SEQ ID NO 184
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 184
gtcccgcggg gcccgaagcg tttactttga aaaaattaga gtgttcaaag caggcccg       58

<210> SEQ ID NO 185
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 185
tgctaatgtg agacgaattt ttgagcgggt aaaggtcgcc ctcaaggtga cccgccta       58

<210> SEQ ID NO 186
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 186
tggcagggga gataccatga tcacgaaggt ggttttctca gggcgaggct tatccatt       58

<210> SEQ ID NO 187
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 187
agttggtccg agtgt                                                      15

<210> SEQ ID NO 188
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 188
tggttagtac tctgcgttgt g                                               21

<210> SEQ ID NO 189
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 189
tccgatggta gtgggttatc a                                               21

<210> SEQ ID NO 190
<211> LENGTH: 66
<212> TYPE: DNA
<213> ORGANISM: Artificial Sequence
<220> FEATURE:
<223> OTHER INFORMATION: Synthetic polynucleotide -continued

<400> SEQUENCE: 190
gctgagtgtc ccgcggggcc cgaagcgttt actttgaaaa aattagagtg ttcaaagcag    60
gcccga    66

<210> SEQ ID NO 191
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 191
tggtccgagt gttgtgggtt attgtt    26

<210> SEQ ID NO 192
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 192
tggtccgagt gttgtgggtt attgtta    27

<210> SEQ ID NO 193
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 193
ttggtccgat ggtagtgggt tatca    25

<210> SEQ ID NO 194
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 194
aagaaattca atgaagcgcg ggtaaacggc gggagtaact atgactctct t    51

<210> SEQ ID NO 195
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 195
agtgttgtgg gttattgtt    19

<210> SEQ ID NO 196
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 196
agttggtccg agtgtggtgg gttattgtt    29

<210> SEQ ID NO 197
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 197
agttggtccg agtgttgtgg gttatta                                27

<210> SEQ ID NO 198
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 198
attgaaacaa gcaacctgtc tgggttgttc gagacccgcg ggcgctctcc agtcctt    57

<210> SEQ ID NO 199
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 199
gagttggtcc gagtgttgtg ggtta                                  25

<210> SEQ ID NO 200
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 200
taatgtgaga cgaattttg agcgggtaaa ggtcgccctc aaggtgaccc gcctactt    58

<210> SEQ ID NO 201
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 201
attgaaacaa gcaacctgtc tgggttgttc gagacccgcg ggcgctctcc agtccttt   58

<210> SEQ ID NO 202
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 202
cgagtgttgt gggttattgt ta                                     22

<210> SEQ ID NO 203
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 203
aagaaattca atgaagcgcg ggtaaacggc gggagtaact a                41

<210> SEQ ID NO 204
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 204
atagaagccg gcgtaaaga                                         19

<210> SEQ ID NO 205
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 205
tggctggtcc gaaggtagtg agttatctca attg                        34

<210> SEQ ID NO 206
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 206
ttagcactct ggactttg                                          18

<210> SEQ ID NO 207
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 207
aatggttagc actctggact ctg                                    23

<210> SEQ ID NO 208
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 208
gctgagtgtc ccgcggggcc cgaagcgttt actttgaaa                   39

<210> SEQ ID NO 209
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 209
cagttggtcc gagtgttgtg ggttatt                                27

<210> SEQ ID NO 210

<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 210
tggctggtcc gaaggtagtg agtta                                        25

<210> SEQ ID NO 211
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 211
aaggtagcca aatgcctcgt catcta                                       26

<210> SEQ ID NO 212
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 212
aggtagccaa atgcctcgtc atcta                                        25

<210> SEQ ID NO 213
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 213
atacatgccg acgggcgctg accccttcg cgggggggat gcgtgcattt              50

<210> SEQ ID NO 214
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 214
atggctggtc cgatggtagt gggttatca                                    29

<210> SEQ ID NO 215
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 215
ggttagcact ctggactttg                                              20

<210> SEQ ID NO 216
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 216
tactctgcgt tgtg                                                      14

<210> SEQ ID NO 217
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 217
gtgttgtatg aaaggagaga aggtta                                         26

<210> SEQ ID NO 218
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 218
tcacatcctg acacaactct tgtcctggtg tgctagagta ctcgaagaga atctactggt    60
cttg                                                                 64

<210> SEQ ID NO 219
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 219
agctgctaag tgctgtgttg tcgttccccc tgcttaaaat aaagttgttt cttaacta      58

<210> SEQ ID NO 220
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 220
gcctcgttag cgcagta                                                   17

<210> SEQ ID NO 221
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 221
ggttagcact ctggactctg                                                20

<210> SEQ ID NO 222
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 222
gtctaggggt aggattctcg ctttg                                          25

<210> SEQ ID NO 223

<210> SEQ ID NO 223
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 223
tgaagcgttt actttgaaaa aattagagtg ttcaaagcag gcccg                45

<210> SEQ ID NO 224
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 224
tggctggtcc gaaggtagtg agttatctca att                             33

<210> SEQ ID NO 225
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 225
ttagagcatc agactttt                                              18

<210> SEQ ID NO 226
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 226
agagcactgg tattg                                                 15

<210> SEQ ID NO 227
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 227
ataagtggga ggcccccggc gccccccgg tgtccccgcg aggggcccgg ggcggggt    58

<210> SEQ ID NO 228
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 228
ctgagtgtcc cgcggggccc gaagcgttta ctttgaaa                        38

<210> SEQ ID NO 229
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 229
gcgatggtag tgggttatca                                              20

<210> SEQ ID NO 230
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 230
gtgtaatggt tagcactctg gactctgcg                                    29

<210> SEQ ID NO 231
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 231
tgccgtgatc gtatagtggt tagtactctg cgttgtg                           37

<210> SEQ ID NO 232
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 232
agttggtccg agtgttgtgg gttattgtt                                    29

<210> SEQ ID NO 233
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 233
aagcgtttac tttgaaa                                                 17

<210> SEQ ID NO 234
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 234
gtgtaatggt tagcactctg gactctgtt                                    29

<210> SEQ ID NO 235
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 235
tagagcactg gttttg                                                  16

<210> SEQ ID NO 236
<211> LENGTH: 31
<212> TYPE: DNA

<213> ORGANISM: Artificial Sequence
<220> FEATURE:
<223> OTHER INFORMATION: Synthetic polynucleotide

<400> SEQUENCE: 236
aagcgtttac tttgaaaaaa ttagagtgtt c                               31

<210> SEQ ID NO 237
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 237
ctttgaaaaa attagagtgt tcaaagcagg cccgagccgc ctggataccg cagctaggaa     60
taatgg                                                               66

<210> SEQ ID NO 238
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 238
ggtccgagtg ttgtgggtta ttgtta                                     26

<210> SEQ ID NO 239
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 239
gtataaacta ataccagt a                                            21

<210> SEQ ID NO 240
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 240
atcgtatagt ggtgagtact ctgcgctgtg                                 30

<210> SEQ ID NO 241
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 241
gcactccgga tgtgctgacc cctgcgattt ccccaaatgt gggaaactcg actgcatt       58

<210> SEQ ID NO 242
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 242
agtgtaatgg ttagcactct ggactttg                                28

<210> SEQ ID NO 243
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 243
cgagtgttgt gggttatt                                           18

<210> SEQ ID NO 244
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 244
ggctggtccg aaggtagtga gttatctcaa ttgattgttc acagtcagtt         50

<210> SEQ ID NO 245
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 245
tcacgtctgc ttta                                               14

<210> SEQ ID NO 246
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 246
ttggtccgag tgttgtgggt tattg                                   25

<210> SEQ ID NO 247
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 247
cagttggtcc gagtgttgtg ggttattgtt a                            31

<210> SEQ ID NO 248
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 248
ttagaccgtc gtgagacagg ttagtt                                  26

<210> SEQ ID NO 249
<211> LENGTH: 24
<212> TYPE: DNA

```
<213> ORGANISM: Artificial Sequence
<220> FEATURE:
<223> OTHER INFORMATION: Synthetic polynucleotide

<400> SEQUENCE: 249
ggctggtccg aaggtagtga gtta                                             24

<210> SEQ ID NO 250
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 250
atagggaacg tgagctgggt ttagaccgtc gtgagacagg ttagtt                     46

<210> SEQ ID NO 251
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 251
gagcttcctc gtggcgccgg gggtcaatct gcagcgctag agcatgtgct tgcgcata       58

<210> SEQ ID NO 252
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 252
gtataaacta ataccaccagt ta                                              22

<210> SEQ ID NO 253
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 253 tagggtatg attctcgctt tg                                                22

<210> SEQ ID NO 254
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 254
tgaagcgttt actttgaaaa aattagagtg ttcaaagcag gccc                       44

<210> SEQ ID NO 255
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 255
gagttggtcc gagtgttgtg ggttatt                                          27
```

<210> SEQ ID NO 256
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 256
gagtgttgtg ggttattgtt a                                            21

<210> SEQ ID NO 257
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 257
tcgatggtag tgggttatc                                               19

<210> SEQ ID NO 258
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 258
aaggtagtga gttatctcaa tt                                           22

<210> SEQ ID NO 259
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 259
agcaggaggt gtcagaaaag tt                                           22

<210> SEQ ID NO 260
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 260
ccgagtgttg tgggttatt                                               19

<210> SEQ ID NO 261
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 261
ccgtgatcgt atagtggtta gtactctgcg ttgtg                             35

<210> SEQ ID NO 262
<211> LENGTH: 66
<212> TYPE: DNA
<213> ORGANISM: Artificial Sequence
<220> FEATURE:

<223> OTHER INFORMATION: Synthetic polynucleotide

<400> SEQUENCE: 262
gccatggaag tcggaatccg ctaaggagtg tgtaacaact cacctgccga atcaactagc    60
cctgtt    66

<210> SEQ ID NO 263
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 263
ttggtccgag tgttgtgggt tatt    24

<210> SEQ ID NO 264
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 264
cgggccgccg gtgaaatacc actactctga tcgtttttc actgacccgg t    51

<210> SEQ ID NO 265
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 265
taaggtagtg agttatctca att    23

<210> SEQ ID NO 266
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 266
tatcagtgat gttgtaaaaa taaatgtctg aacata    36

<210> SEQ ID NO 267
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 267
agttggtccg agggttgtgg gttattgtt    29

<210> SEQ ID NO 268
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 268
acaatacagg actctttcga ggccctgtaa ttggaatgag tccactta    49

<210> SEQ ID NO 269
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 269
acgaacgaga ctctggcatg ctaacta                                27

<210> SEQ ID NO 270
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 270
atcgaggccc agcccgtgga cggtgtgagg ccggta                      36

<210> SEQ ID NO 271
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 271
gtataaacta ataccaccagt ct                                    22

<210> SEQ ID NO 272
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 272
gttggtccga gtgttgtggg ttattg                                 26

<210> SEQ ID NO 273
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 273
agttggtccg agtgttgtgg gttattgtta agttgattta acatt            45

<210> SEQ ID NO 274
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 274
agtgtaatgg ttagcactct ggactctg                               28

<210> SEQ ID NO 275
<211> LENGTH: 30
<212> TYPE: DNA
<213> ORGANISM: Artificial Sequence
<220> FEATURE:

<223> OTHER INFORMATION: Synthetic polynucleotide

<400> SEQUENCE: 275
aaatatgatg agtgtacaaa atcttgattt                                30

<210> SEQ ID NO 276
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 276
aagttggtcc gagtgttgtg ggttattg                                  28

<210> SEQ ID NO 277
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 277
aggggtatga ttctcggttt g                                         21

<210> SEQ ID NO 278
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 278
gcgtttactt tgaaaaaatt agagtgttca aagcaggccc gagccgcctg gataccgc  58

<210> SEQ ID NO 279
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 279
tgattctcgc tttg                                                 14

<210> SEQ ID NO 280
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 280
aaagcacctg tttg                                                 14

<210> SEQ ID NO 281
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 281
atactcgggt ttctcttcaa aacgcataaa tct                            33

<210> SEQ ID NO 282
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 282
atcgtatagt ggttagtact ctgcgttgtg ta                                32

<210> SEQ ID NO 283
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 283
atcgtatagt ggttagtact ctgcgttgtt                                   30

<210> SEQ ID NO 284
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 284
attaaaacaa agcatcgcga aggcccgcgg cgggtgtt                          38

<210> SEQ ID NO 285
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 285
gtgggaggcc cccggcgccc ccccggtgtc cccgcgaggg gcccggggcg gggtccgccg  60
gccctg                                                             66

<210> SEQ ID NO 286
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 286
acagatcgaa ctccttgttc tactctt                                      27

<210> SEQ ID NO 287
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 287
acgaacgaga ctctggcatg cta                                          23

<210> SEQ ID NO 288
<211> LENGTH: 17
<212> TYPE: DNA
<213> ORGANISM: Artificial Sequence
<220> FEATURE:

<223> OTHER INFORMATION: Synthetic polynucleotide

<400> SEQUENCE: 288
gagtgttgtg ggttatt                                                      17

<210> SEQ ID NO 289
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 289
gagttggtcc gagtgttgtg ggttattgtt aa                                     32

<210> SEQ ID NO 290
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 290
tagtggttag tactctgcgt tgtg                                              24

<210> SEQ ID NO 291
<211> LENGTH: 62
<212> TYPE: DNA
<213> ORGANISM: Artificial Sequence
<220> FEATURE:
<223> OTHER INFORMATION: Synthetic polynucleotide

<400> SEQUENCE: 291
tcgggccgcc ggtgaaatac cactactctg atcgtttttt cactgacccg gtgaggcggg       60
gg                                                                      62

<210> SEQ ID NO 292
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 292
tgcacctgac caggtctctg ttggctggtg caatccagtg gtgagctgat agtaaacccc       60
agctta                                                                  66

<210> SEQ ID NO 293
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 293
tgccgtgatc gtatagtggt ta                                                22

<210> SEQ ID NO 294
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 294
tttggtggtt cagtggtaga a                                              21

<210> SEQ ID NO 295
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 295
atgattctcg ctttg                                                     15

<210> SEQ ID NO 296
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 296
acgggtgacg gggaa                                                     15

<210> SEQ ID NO 297
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 297
ataccgcagc taggaataat ggaata                                         26

<210> SEQ ID NO 298
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 298
cacgcgcgcg tcccccgaag aggggacgg cggagcgagc gcacggggtc ggcggcga      58

<210> SEQ ID NO 299
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 299
ggttccatag tgtagcggtt atcacgtctg cttta                               35

<210> SEQ ID NO 300
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 300
gtgtaatggt tagcactctg gactttgta                                      29

<210> SEQ ID NO 301
<211> LENGTH: 39
<212> TYPE: DNA

<213> ORGANISM: Artificial Sequence
<220> FEATURE:
<223> OTHER INFORMATION: Synthetic polynucleotide

<400> SEQUENCE: 301
tagttggtcc gagtgttgtg ggttattgtt aagttgatt                                    39

<210> SEQ ID NO 302
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 302
tttgaaaaaa ttagagtgtt caaagcaggc ccgagccgcc tggataccgc agctaggaat            60
aatgga                                                                        66

<210> SEQ ID NO 303
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 303
agttggtccg agtgttgtgg gttattg                                                 27

<210> SEQ ID NO 304
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 304
acaaagcatc gcgaaggccc gcggcgggtg ttgacgcgat gtgatt                            46

<210> SEQ ID NO 305
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 305
agttggtccg agtgttgtgg gttattgtta agttgattta acat                              44

<210> SEQ ID NO 306
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 306
gggctggctt tagctcagcg gttacttcga gta                                          33

<210> SEQ ID NO 307
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 307

```
gggctggtcc gatggtagtg ggtta                                          25

<210> SEQ ID NO 308
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 308
gtcttgtttg tagcttcacg ggccaagcaa cagtgctaga gcataacgac ttgttata    58

<210> SEQ ID NO 309
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 309
tatgattctc gctttg                                                    16

<210> SEQ ID NO 310
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 310
aaaacaaagc atcgcgaagg cccgcggcgg gtgttgacgc gatgtgatt               49

<210> SEQ ID NO 311
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 311
aagcgtttac tttgaaaaaa ttagagtgtt caaagca                             37

<210> SEQ ID NO 312
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 312
agcaggaggt gtcagaaaag ttaccacagg gata                                34

<210> SEQ ID NO 313
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 313
agttggtccg agtgttgtgg gttattt                                        27

<210> SEQ ID NO 314
<211> LENGTH: 32
<212> TYPE: DNA
```

```
<213> ORGANISM: Artificial Sequence
<220> FEATURE:
<223> OTHER INFORMATION: Synthetic polynucleotide

<400> SEQUENCE: 314
atagttggtc cgagtgttgt gggttattgt ta                                32

<210> SEQ ID NO 315
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 315
attgtgaagc agaattcacc aagcgttgga ttgttcaccc acta                   44

<210> SEQ ID NO 316
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 316
gagttggtcc gagtgttgtg ggttattg                                     28

<210> SEQ ID NO 317
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 317
tggatgtgag gcgatctgg ctgcgacatc tgtcacccca ttgatcgcca gggttg       56

<210> SEQ ID NO 318
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 318
ccgagtgttg tgggttattg tt                                           22

<210> SEQ ID NO 319
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 319 ctagggtat gattctcggt ttg                                           23

<210> SEQ ID NO 320
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 320
gaagcgttta ctttgaaaaa attagagtgt tcaaagcagg cccga                  45
```

<210> SEQ ID NO 321
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 321
ttagcactct ggactctg                                                18

<210> SEQ ID NO 322
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 322
cagttggtcc gagtgttgtg ggttattgtt                                   30

<210> SEQ ID NO 323
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 323
agttggtccg agtgttgtgg gttattgtta agttgattta acattg                 46

<210> SEQ ID NO 324
<211> LENGTH: 70
<212> TYPE: DNA
<213> ORGANISM: Artificial Sequence
<220> FEATURE:
<223> OTHER INFORMATION: Synthetic polynucleotide

<400> SEQUENCE: 324
aataagtggg aggcccccgg cgccccccg gtgtccccgc gaggggcccg gggcggggtc   60
cgccggccct                                                         70

<210> SEQ ID NO 325
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 325
agttggtccg agtgttgtgg gttattgtta agttgatt                          38

<210> SEQ ID NO 326
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 326 ctagggtat gattctcgct ttg                                           23

<210> SEQ ID NO 327
<211> LENGTH: 58
<212> TYPE: DNA

<213> ORGANISM: Artificial Sequence
<220> FEATURE:
<223> OTHER INFORMATION: Synthetic polynucleotide

<400> SEQUENCE: 327
gctttctttt atgtgagtag tgttatttct tatgtgctat acaaataatt gaaggcta        58

<210> SEQ ID NO 328
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 328
gttagtactc tgcgttgtg                                                   19

<210> SEQ ID NO 329
<211> LENGTH: 63
<212> TYPE: DNA
<213> ORGANISM: Artificial Sequence
<220> FEATURE:
<223> OTHER INFORMATION: Synthetic polynucleotide

<400> SEQUENCE: 329
tagcaggacg gtggccatgg aagtcggaat ccgctaagga gtgtgtaaca actcacctgc       60
cga                                                                    63

<210> SEQ ID NO 330
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 330
aagaaattca atgaagcgcg ggta                                             24

<210> SEQ ID NO 331
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 331
acgtgcgcga gtcgggggct cgcacgaaag ccgccgtggc gcaatg                     46

<210> SEQ ID NO 332
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 332
gtatagtggt gagtatcccc gcctgtcta                                        29

<210> SEQ ID NO 333
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 333
gtccgatggt agtgggttat ca    22

<210> SEQ ID NO 334
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 334
tagccaaatg cctcgtcatc ta    22

<210> SEQ ID NO 335
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 335
tcagatcaaa accaacccgg tcagcccctc tccggccccg gccgggggc gggcgccggc    60 ggcttt    66

<210> SEQ ID NO 336
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 336
tcattgtgaa gcagaattca ccaagcgttg gattgttcac ccacta    46

<210> SEQ ID NO 337
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 337
tggctggtcc gaaggtagtg agtt    24

<210> SEQ ID NO 338
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 338
gttagcactc tggactttg    19

<210> SEQ ID NO 339
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 339
aagcgtttac tttgaaaaaa ttagag    26

<210> SEQ ID NO 340

```
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 340
acgagactct ggcatgcta                                                    19

<210> SEQ ID NO 341
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 341
agtgcggtaa cgcgaccgat cccggagaag ccggcgggag ccccggggag agttctcttt        60
tctt                                                                    64

<210> SEQ ID NO 342
<211> LENGTH: 5070
<212> TYPE: DNA
<213> ORGANISM: Artificial Sequence
<220> FEATURE:
<223> OTHER INFORMATION: Synthetic polynucleotide

<400> SEQUENCE: 342
cgcgacctca gatcagacgt ggcgacccgc tgaatttaag catattagtc agcggaggag        60
aagaaactaa ccaggattcc ctcagtaacg gcgagtgaac agggaagagc ccagcgccga       120
atccccgccc cgcggcgggg cgcgggacat gtggcgtacg aagacccgc tccccggcgc        180 cgctcgtggg gggcccaagt ccttctgatc gaggcccagc ccgtgacgg tgtgaggccg        240 gtagcggccc ccggcgcgcc gggcccgggt cttcccggag tcgggttgct tgggaatgca       300
gcccaaagcg ggtggtaaac tccatctaag gctaaatacc ggcacgagac cgatagtcaa       360
caagtaccgt aagggaaagt tgaaaagaac tttgaagaga gagttcaaga gggcgtgaaa       420
ccgttaagag gtaaacgggt ggggtccgcg cagtccgccc ggaggattca acccggcggc       480
gggtccggcc gtgtcggcgg cccggcggat ctttcccgcc ccccgttcct cccgacccct       540
ccacccgccc tccttccccc cgccgcccct cctcctcctc ccggaggggg cgggctccg        600 gcgggtgcgg gggtgggcgg gcggggccgg gggtggggtc ggcgggggac cgtcccccga       660
ccggcgaccg gccgccgccg ggcgcatttc caccgcggcg gtgcgccgcg accggctccg       720
ggacggctgg gaaggcccgg cggggaaggt ggctcggggg gccccgtccg tccgtccgtc       780
cgtcctcctc ctcccccgtc tccgcccccc ggccccgcgt cctccctcgg gagggcgcgc       840
gggtcggggc ggcggcggcg gcggcggtgg cggcggcggc ggcggcggcg ggaccgaaac       900 ccccccccgag tgttacagcc cccccggcag cagcactcgc cgaatccggg gccgaggga       960 gcgagacccg tcgccgcgct ctcccccctc ccggcgccca ccccgcgggg gaatccccg      1020 cgaggggggt ctccccgcg ggggcgcgcc ggcgtctcct cgtgggggg ccgggccacc       1080 cctcccacgg cgcgaccgct ctcccacccc tcctcccgc gccccgccc cggcgacggg       1140 gggggtgccg cgcgcgggtc gggggcggg gcggactgtc cccagtgcgc cccgggcggg       1200
tcgcgccgtc gggccggggg gaggttctct cggggccacg cgcgcgtccc cgaagaggg      1260 ggacggcgga gcgagcgcac ggggtcggcg gcgacgtcgg ctacccaccc gacccgtctt      1320
gaaacacgga ccaaggagtc taacacgtgc gcgagtcggg ggctcgcacg aaagccgccg      1380
```

```
tggcgcaatg aaggtgaagg ccggcgcgct cgccggccga ggtgggatcc cgaggcctct    1440
ccagtccgcc gagggcgcac caccggcccg tctcgcccgc cgcgccgggg aggtggagca    1500
cgagcgcacg tgttaggacc cgaaagatgg tgaactatgc ctgggcaggg cgaagccaga    1560
ggaaactctg gtggaggtcc gtagcggtcc tgacgtgcaa atcggtcgtc cgacctgggt    1620
ataggggcga agactaatc gaaccatcta gtagctggtt ccctccgaag tttccctcag     1680
gatagctggc gctctcgcag acccgacgca ccccgccac gcagttttat ccggtaaagc     1740
gaatgattag aggtcttggg gccgaaacga tctcaaccta ttctcaaact ttaaatgggt    1800
aagaagcccg gctcgctggc gtggagccgg gcgtggaatg cgagtgccta gtgggccact    1860
tttggtaagc agaactggcg ctgcgggatg aaccgaacgc cgggttaagg cgcccgatgc    1920
cgacgctcat cagaccccag aaaaggtgtt ggttgatata gacagcagga cggtggccat    1980
ggaagtcgga atccgctaag gagtgtgtaa caactcacct gccgaatcaa ctagccctga    2040
aaatggatgg cgctggagcg tcgggcccat accggccgt cgccggcagt cgagagtgga     2100
cgggagcggc ggggggcggcg cgcgcgcgcg cgcgtgtggt gtgcgtcgga gggcggcggc    2160
ggcggcggcg gcggggtgt gggtccttc ccccgccccc ccccccacgc ctcctcccct      2220
cctcccgccc acgccccgct ccccgccccc ggagcccgc ggacgctacg ccgcgacgag     2280
taggagggcc gctgcggtga gccttgaagc ctagggcgcg ggcccgggtg gagccgccgc    2340
aggtgcagat cttggtggta gtagcaaata ttcaaacgag aactttgaag gccgaagtgg    2400
agaagggttc catgtgaaca gcagttgaac atgggtcagt cggtcctgag agatgggcga    2460
gcgccgttcc gaagggacgg gcgatggcct ccgttgccct cggccgatcg aaagggagtc    2520
gggttcagat ccccgaatcc ggagtggcgg agatgggcgc cgcgaggcgt ccagtgcggt    2580
aacgcgaccg atcccggaga agccggcggg agccccgggg agagttctct tttctttgtg    2640
aagggcaggg cgccctggaa tgggttcgcc ccgagagagg ggcccgtgcc ttggaaagcg    2700
tcgcggttcc ggcggcgtcc ggtgagctct cgctggccct tgaaaatccg ggggagaggg    2760
tgtaaatctc gcgccgggcc gtacccatat ccgcagcagg tctccaaggt gaacagcctc    2820
tggcatgttg gaacaatgta ggtaagggaa gtcggcaagc cggatccgta acttcgggat    2880
aaggattggc tctaagggct gggtcggtcg ggctggggcg cgaagcgggg ctgggcgcgc    2940
gccgcggctg gacgaggcgc cgccgccccc ccacgcccg gggcacccccc ctcgcggccc    3000 tccccgcccc caccccgcgc gcgccgctcg ctccctcccc gccccgcgcc ctctctctct    3060
ctctctcccc cgctccccgt cctcccccct ccccggggga gcgccgcgtg ggggcggcgg    3120 cgggggaga agggtcgggg cggcaggggc cggcggcggc ccgccgcggg gccccggcgg    3180 cggggcacg gtccccgcg aggggggccc gggcacccgg ggggcggcg gcggcggcga      3240 ctctggacgc gagccgggcc cttcccgtgg atcgcccccag ctgcggcggg cgtcgcggcc   3300 gccccgggg agcccggcgg ggcgcggcgc gccccccccc ccaccccacg tctcgtcgcg    3360
cgcgcgtccg ctggggcgg ggagcggtcg ggcggcggcg gtcggcgggc ggcggggcgg    3420
ggcggttcgt ccccccgccc tacccccccg gcccgtccg ccccccgttc ccccctcctc    3480
ctcggcgcgc ggcggcggcg gcggcaggcg cggaggggc cgcgggccgg tccccccgc     3540 cgggtccgcc cccggggccg cggttccgcg cggcgcctcg cctcggccgg cgcctagcag    3600
ccgacttaga actggtgcgg accaggggaa tccgactgtt taattaaaac aaagcatcgc    3660
gaaggcccgc ggcgggtgtt gacgcgatgt gatttctgcc cagtgctctg aatgtcaaag    3720
```

-continued

```
tgaagaaatt caatgaagcg cgggtaaacg gcgggagtaa ctatgactct cttaaggtag    3780
ccaaatgcct cgtcatctaa ttagtgacgc gcatgaatgg atgaacgaga ttcccactgt    3840
ccctacctac tatccagcga aaccacagcc aagggaacgg gcttggcgga atcagcgggg    3900
aaagaagacc ctgttgagct tgactctagt ctggcacggt gaagagacat gagaggtgta    3960
gaataagtgg gaggcccccg cgcccccccc ggtgtccccg cgaggggccc ggggcggggt    4020
ccgccggccc tgcgggccgc cggtgaaata ccactactct gatcgttttt tcactgaccc    4080
ggtgaggcgg gggggcgagc cccgagggc tctcgcttct ggcgccaagc gcccggccgc     4140
gcgccggccg ggcgcgaccc gctccgggga cagtgccagg tggggagttt gactggggcg    4200
gtacacctgt caaacggtaa cgcaggtgtc ctaaggcgag ctcagggagg acagaaacct    4260
cccgtggagc agaagggcaa aagctcgctt gatcttgatt ttcagtacga atacagaccg    4320
tgaaagcggg gcctcacgat ccttctgacc ttttgggttt taagcaggag gtgtcagaaa    4380
agttaccaca gggataactg gcttgtggcg gccaagcgtt catagcgacg tcgcttttg     4440 atccttcgat gtcggctctt cctatcattg tgaagcagaa ttcaccaagc gttggattgt    4500
tcacccacta atagggaacg tgagctgggt ttagaccgtc gtgagacagg ttagttttac    4560
cctactgatg atgtgttgtt gccatggtaa tcctgctcag tacgagagga accgcaggtt    4620
cagacatttg gtgtatgtgc ttggctgagg agccaatggg gcgaagctac catctgtggg    4680
attatgactg aacgcctcta agtcagaatc ccgcccaggc ggaacgatac ggcagcgccg    4740
cggagcctcg gttggcctcg gatagccggt ccccgcctg tccccgccgg cgggccgccc     4800 ccccctcca cgcgccccgc gcgcgcggga gggcgcgtgc cccgccgcgc gccgggaccg    4860
gggtccggtg cggagtgccc ttcgtcctgg gaaacggggc gcggccggag aggcggccgc    4920 ccctcgccc gtcacgcacc gcacgttcgt ggggaacctg gcgctaaacc attcgtagac     4980
gacctgcttc tgggtcgggg tttcgtacgt agcagagcag ctccctcgct gcgatctatt    5040
gaaagtcagc cctcgacaca agggtttgtc                                    5070
```

<210> SEQ ID NO 343
<211> LENGTH: 12
<212> TYPE: RNA
<213> ORGANISM: Artificial Sequence
<220> FEATURE:
<223> OTHER INFORMATION: Synthetic

<400> SEQUENCE: 343
cguuguggcc gc                                                       12

<210> SEQ ID NO 344
<211> LENGTH: 12
<212> TYPE: RNA
<213> ORGANISM: Artificial Sequence
<220> FEATURE:
<223> OTHER INFORMATION: Synthetic

<400> SEQUENCE: 344
uucaauugau ug                                                       12

<210> SEQ ID NO 345
<211> LENGTH: 12
<212> TYPE: RNA
<213> ORGANISM: Artificial Sequence
<220> FEATURE:
<223> OTHER INFORMATION: Synthetic

<400> SEQUENCE: 345
acaacuuauu ua                                           12

<210> SEQ ID NO 346
<211> LENGTH: 21
<212> TYPE: RNA
<213> ORGANISM: Artificial Sequence
<220> FEATURE:
<223> OTHER INFORMATION: Synthetic

<400> SEQUENCE: 346
aguggguuau cagaacuuau u                                 21

<210> SEQ ID NO 347
<211> LENGTH: 12
<212> TYPE: RNA
<213> ORGANISM: Artificial Sequence
<220> FEATURE:
<223> OTHER INFORMATION: Synthetic

<400> SEQUENCE: 347
guuaucagaa cu                                           12

<210> SEQ ID NO 348
<211> LENGTH: 12
<212> TYPE: RNA
<213> ORGANISM: Artificial Sequence
<220> FEATURE:
<223> OTHER INFORMATION: Synthetic

<400> SEQUENCE: 348
guuuuuuauu uu                                           12

<210> SEQ ID NO 349
<211> LENGTH: 12
<212> TYPE: RNA
<213> ORGANISM: Artificial Sequence
<220> FEATURE:
<223> OTHER INFORMATION: Synthetic

<400> SEQUENCE: 349
guuauuucau uu                                           12

<210> SEQ ID NO 350
<211> LENGTH: 12
<212> TYPE: RNA
<213> ORGANISM: Artificial Sequence
<220> FEATURE:
<223> OTHER INFORMATION: Synthetic

<400> SEQUENCE: 350
acaauuuauu ua                                           12

<210> SEQ ID NO 351
<211> LENGTH: 12
<212> TYPE: RNA
<213> ORGANISM: Artificial Sequence
<220> FEATURE:
<223> OTHER INFORMATION: Synthetic

<400> SEQUENCE: 351
auuuuuuagu uu                                           12

<210> SEQ ID NO 352
<211> LENGTH: 12
<212> TYPE: RNA

```
<213> ORGANISM: Artificial Sequence
<220> FEATURE:
<223> OTHER INFORMATION: Synthetic

<400> SEQUENCE: 352
cguuguggcc gc                                                        12

<210> SEQ ID NO 353
<211> LENGTH: 12
<212> TYPE: RNA
<213> ORGANISM: Artificial Sequence
<220> FEATURE:
<223> OTHER INFORMATION: Synthetic

<400> SEQUENCE: 353
uguguuaucu ca                                                        12

<210> SEQ ID NO 354
<211> LENGTH: 12
<212> TYPE: RNA
<213> ORGANISM: Artificial Sequence
<220> FEATURE:
<223> OTHER INFORMATION: Synthetic

<400> SEQUENCE: 354
acuuuuuuuu uu                                                        12

<210> SEQ ID NO 355
<211> LENGTH: 12
<212> TYPE: RNA
<213> ORGANISM: Artificial Sequence
<220> FEATURE:
<223> OTHER INFORMATION: Synthetic

<400> SEQUENCE: 355 cccccccuugu uu                                                       12
```